United States Patent
Nissenbaum et al.

(10) Patent No.: US 11,554,187 B2
(45) Date of Patent: Jan. 17, 2023

(54) REMOTE PATHOGEN ERADICATION

(71) Applicants: Israel Nissenbaum, Brooklyn, NY (US); Mitchell J. Bogart, New Haven, CT (US); Asher Baum, Brooklyn, NY (US)

(72) Inventors: Israel Nissenbaum, Brooklyn, NY (US); Mitchell J. Bogart, New Haven, CT (US); Asher Baum, Brooklyn, NY (US)

(*) Notice: Subject to any disclaimer, the term of this patent is extended or adjusted under 35 U.S.C. 154(b) by 0 days.

(21) Appl. No.: 17/244,860

(22) Filed: Apr. 29, 2021

(65) Prior Publication Data

US 2021/0338854 A1    Nov. 4, 2021

Related U.S. Application Data

(60) Provisional application No. 63/017,407, filed on Apr. 29, 2020, provisional application No. 63/044,641, (Continued)

(51) Int. Cl.
*A61L 2/00* (2006.01)
*A61B 18/18* (2006.01)
(Continued)

(52) U.S. Cl.
CPC ........ *A61L 2/0047* (2013.01); *A61B 1/00117* (2013.01); *A61B 1/126* (2013.01);
(Continued)

(58) Field of Classification Search
CPC .......... A61L 2/00; A61L 2/0047; B29C 35/00
(Continued)

(56) References Cited

U.S. PATENT DOCUMENTS

| 4,761,047 A | 8/1988 | Mori |
| 9,023,092 B2 | 5/2015 | Natale |

(Continued)

FOREIGN PATENT DOCUMENTS

WO    WO 2019/143647 A1    7/2019

OTHER PUBLICATIONS

Asheesh Gupta et al., Ultraviolet Radiation in Wound Care: Sterilization and Stimulation; Advances in Wound Care, Oct. 2, 2013(8): 422-437 (US).

(Continued)

*Primary Examiner* — Monzer R Chorbaji
(74) *Attorney, Agent, or Firm* — Israel Nissenbaum; Yitay Nissenbaum

(57) ABSTRACT

A method and device for the remote eradication of pathogens comprising a light source for emitting UV light in the pathogen killing wave length range, and a tangible transmission medium, which is at least initially resistant to degradation by the UV light. An optical interface between the UV light source and the tangible transmission medium is provided whereby the emitted UV light is collected from the light source and transmitted through the tangible transmission medium, whereby UV light emitted from the tangible transmission medium and directed against a pathogen in proximity thereto is at a power level sufficient to substantially effectively kill the pathogen within a reasonable period of time. The device is used for sanitization of biopsy channels of endoscopes and for treating of pathogens within humans and animals.

18 Claims, 29 Drawing Sheets

Related U.S. Application Data filed on Jun. 26, 2020, provisional application No. 63/077,003, filed on Sep. 11, 2020, provisional application No. 63/118,638, filed on Nov. 25, 2020, provisional application No. 63/139,294, filed on Jan. 19, 2021, provisional application No. 63/149,611, filed on Feb. 15, 2021.

(51) Int. Cl.
- *G01N 21/00* (2006.01)
- *A61B 1/12* (2006.01)
- *A61B 1/00* (2006.01)
- *A61B 90/70* (2016.01)

(52) U.S. Cl.
CPC ........ *A61B 90/70* (2016.02); *A61B 2090/701* (2016.02); *A61B 2217/005* (2013.01); *A61L 2202/22* (2013.01); *A61L 2202/24* (2013.01)

(58) Field of Classification Search
USPC ............ 422/24; 250/453.11, 454.11, 455.11, 250/492.1; 606/9; 607/94
See application file for complete search history.

(56) References Cited

U.S. PATENT DOCUMENTS

| | | | |
|---|---|---|---|
| 10,010,634 B2 | 7/2018 | Bonutti | |
| 2002/0127224 A1* | 9/2002 | Chen | A61K 39/44 424/130.1 |
| 2003/0017073 A1* | 1/2003 | Eckhardt | A61L 2/10 422/24 |
| 2003/0018373 A1* | 1/2003 | Eckhardt | A61N 5/0624 607/94 |
| 2006/0195165 A1 | 8/2006 | Gertner | |
| 2014/0128943 A1* | 5/2014 | Rogers | A61N 5/0603 607/92 |
| 2016/0114185 A1 | 4/2016 | Mankin | |
| 2017/0182194 A1 | 6/2017 | Shin | |
| 2019/0175938 A1 | 6/2019 | Rezaie et al. | |

OTHER PUBLICATIONS

Samuel K. Moore, Ultraviolet-LED Maker Demonstrates 30-second Coronavirus Kill; Tech Talk/Semiconductors/Optoelectronics Apr. 16, 2020.

Thorlabs Catalog pp. 1-6 Fiber-Coupled LEDs copyright 1999-2022.

UV Dose Required to Achieve Incremental Log Inactivation of Bacteria, Protozoa and Viruses Gabriel Chevrefils, B.Ing, and Éric Caron, B.Sc. Tables 1-4 2006 pp. 1-6.

Potential Applications of ultraviolet light phototherapy for wound care and skin disorders Table 1, p. 431 unknown date 1 page.

IEEE of Tech Talk Semiconductors Optoelectronics on Apr. 16, 2020, entitled Ultraviolet-LED Maker Demonstrates 30 Second Coronavirus Kill Samuel K. Moore pp. 1-6.

1 page graph (Figure 3 herein) Expert Rev Anti Infect Ther. Feb. 2012; 10(2): 185-195. Ultraviolet C irradiation: an alternative antimicrobial approach to localized infections?

* cited by examiner

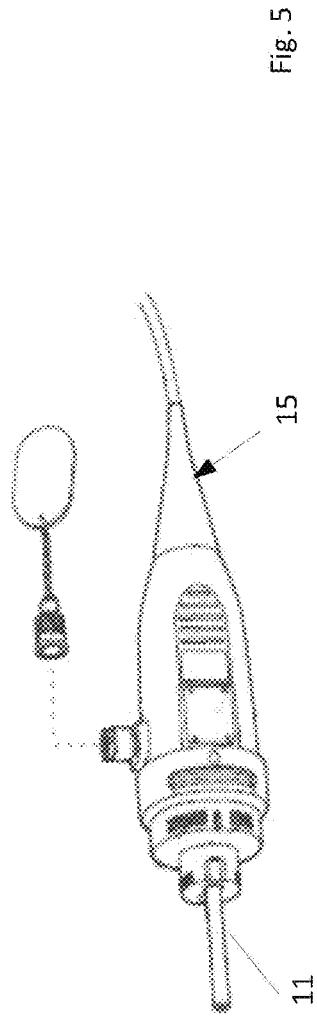
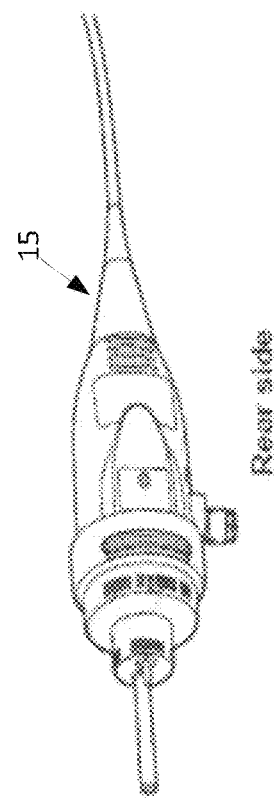
Fig. 5

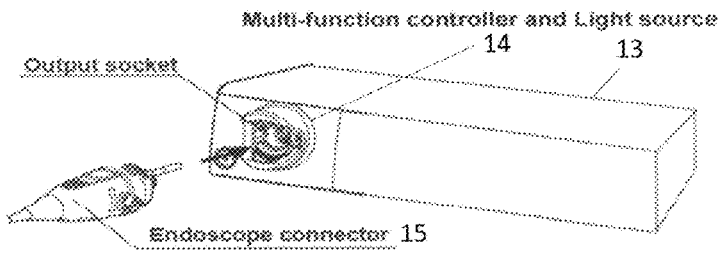
Fig. 6
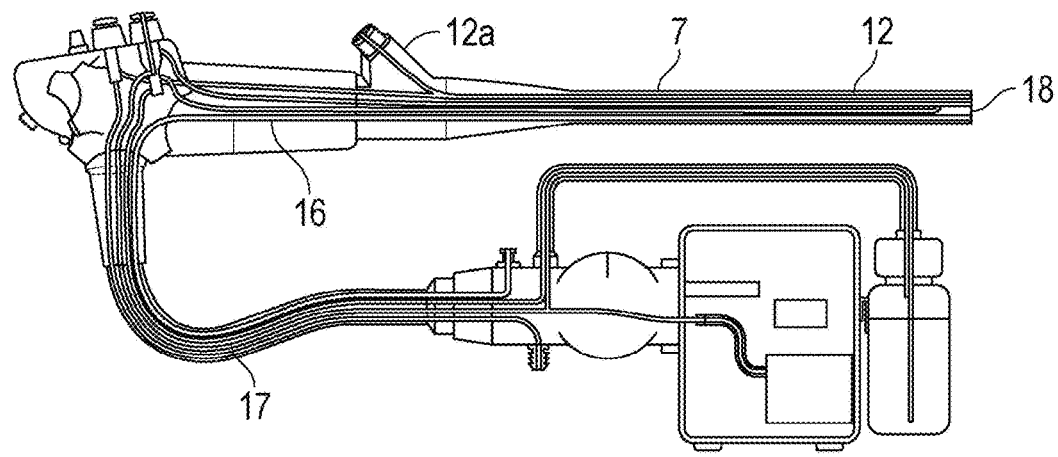
Fig. 7
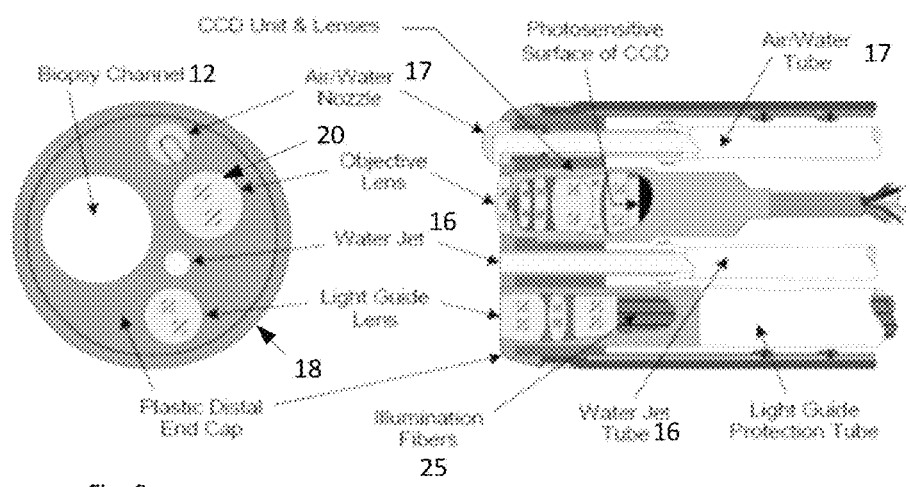
Fig. 8
Fig. 9

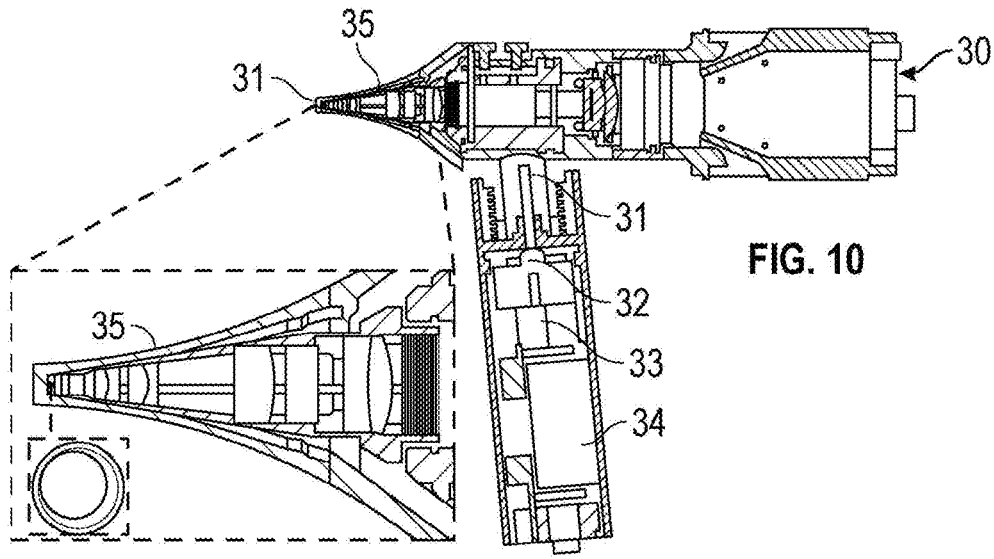

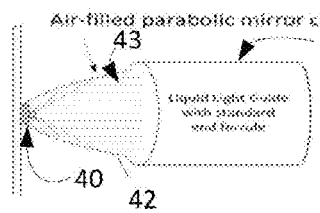

Air-filled parabolic mirror collimator (free-space coupled, as previously described)

Fig. 11a

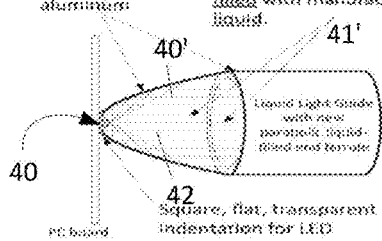

Combined aluminum parabolic mirror/light guide endcap, custom made and filled with manufacturer's light guide liquid.

Square, flat, transparent indentation for LED

The silica or glass end within its aluminum end tube of the light guide is removed. A round-ended parabolic mirror with aluminum housing is joined with the aluminum end tube to make a combined single aluminum end cap with the liquids of mirror and light guide merged to become one liquid volume.

Transmittance is increased and concentric alignment is factory assured.

At the tip of the parabola the mirror is flattened and a square, flat, transparent silica or glass indentation is made to further accommodate positioning over the LED.

Parabolic mirror collimator as a new Liquid Light Guide endcap option

Layout of cables and light flow

Schematic of LED coupling and Sanitizing cable
(TIR lens converging lens)

Schematic of LED coupling and Sanitizing cable
(Parabolic collimator and Fresnel focusing lens)

UVC-3939-265-30P – High Power UV-C LED

Physical/Electrical properties:

| Parameter | Value |
|---|---|
| Emission spectrum at 90% | 260-270 nm |
| Dimensions | 3.9mm x 3.9mm x 3.4mm (L x W x H) |
| Viewing angle 2θ | 30° |
| Power output | 40mw – 45 mw |
| Spectrum width at 50% maximum | 12 nm |
| Maximum Forward current | 450ma |
| Recommended Forward current | 350ma |
| Forward voltage | 5.0 – 8.0 volts |
| Thermal Resistance | ~18 °C/W |

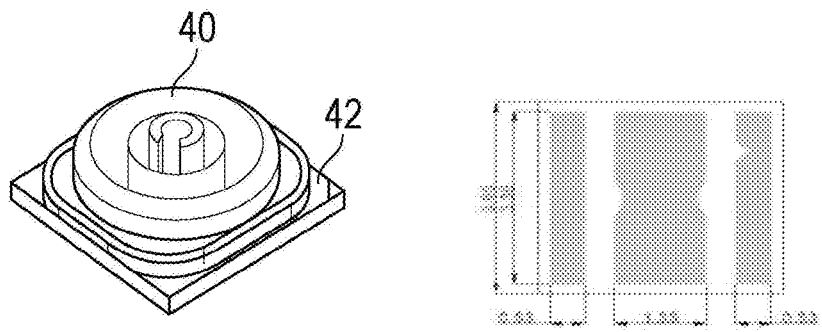

Fig. 26

Electrical/Optical characteristics:

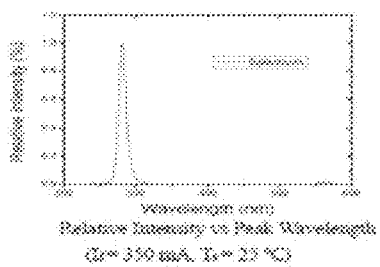

Relative Intensity vs Peak Wavelength
(I$_F$ = 350 mA, T$_a$ = 25 °C)

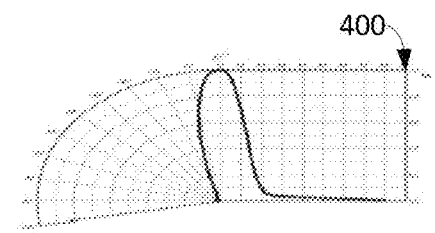

Radiation Pattern
(I$_F$ = 350 mA, T$_a$ = 25 °C)

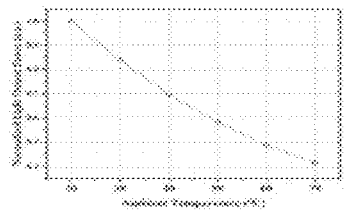

Normalized Light Output Power vs
Ambient Temperature (I$_F$ = 350 mA)

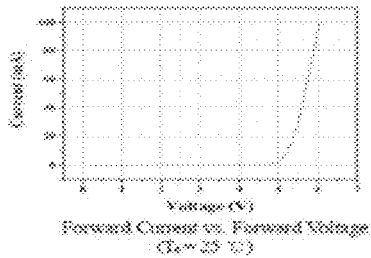

Forward Current vs. Forward Voltage
(T$_a$ = 25 °C)

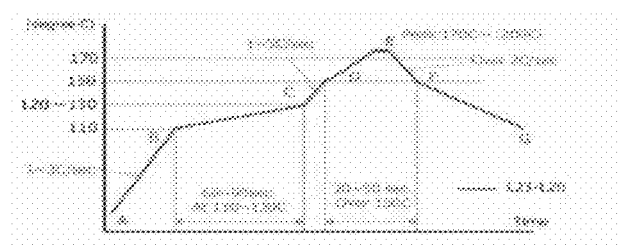

Recommended Dip Soldering Conditions

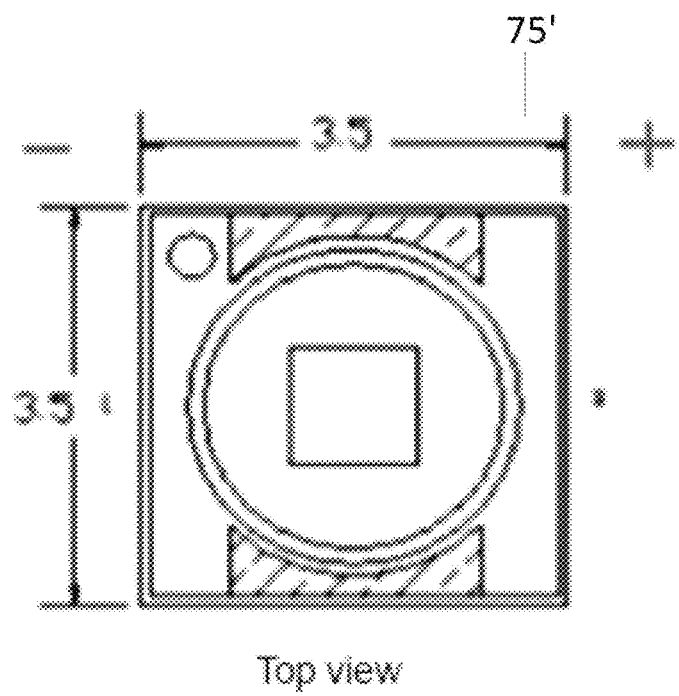
Top view
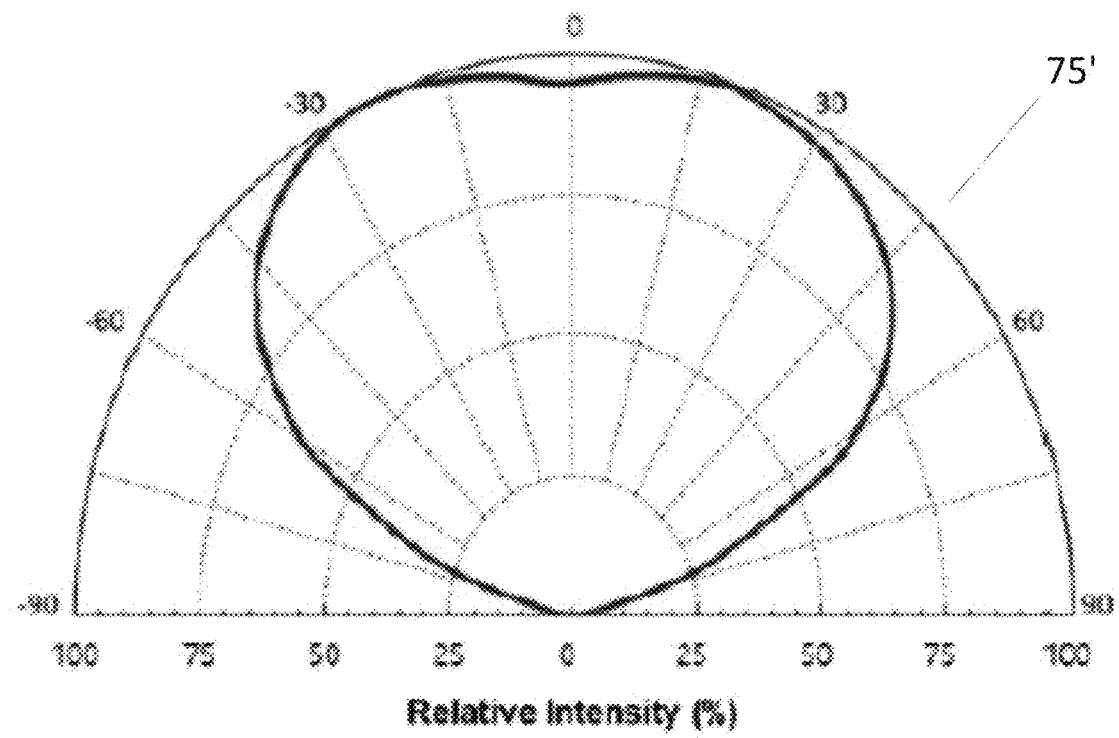
Fig. 27

37 1000um core fibers, a single solid core, fused cores, or whatever is needed to reach 6000um of core diameter Single core version

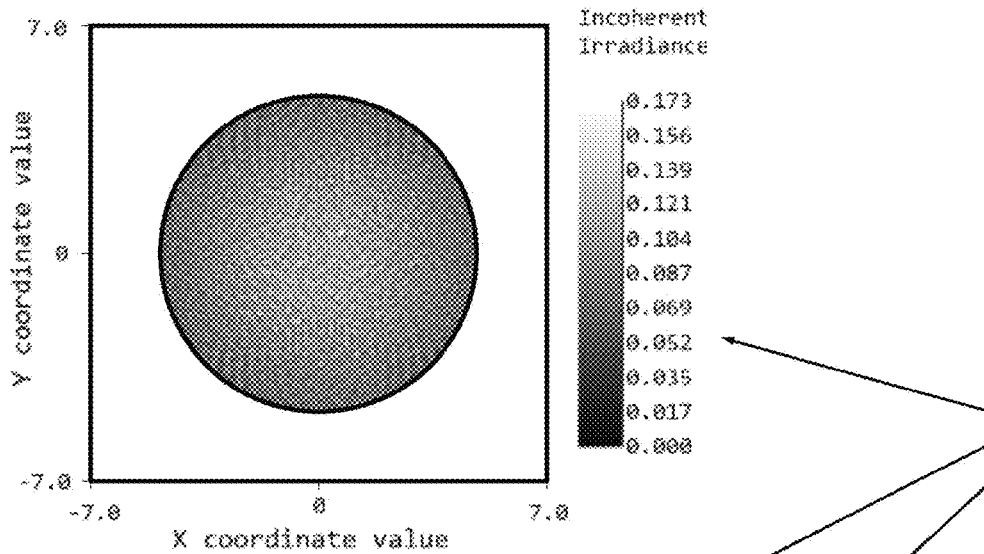
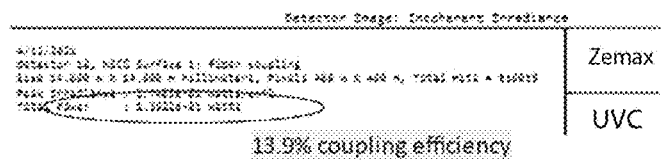
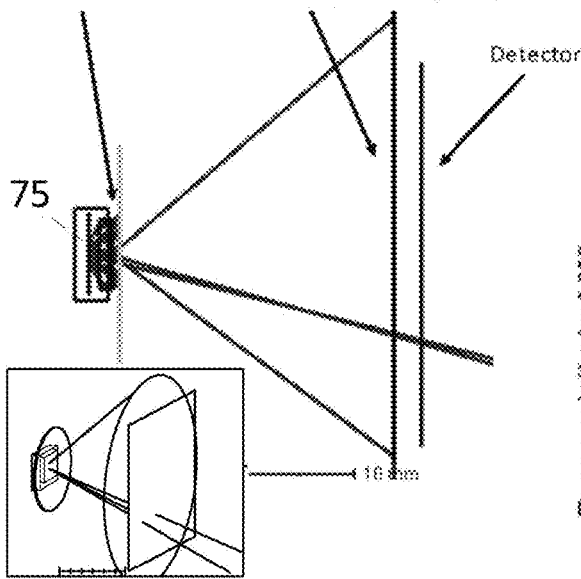
Fig. 38
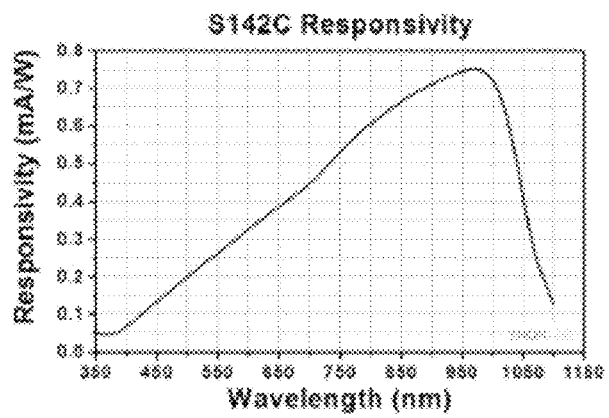
Fig. 40

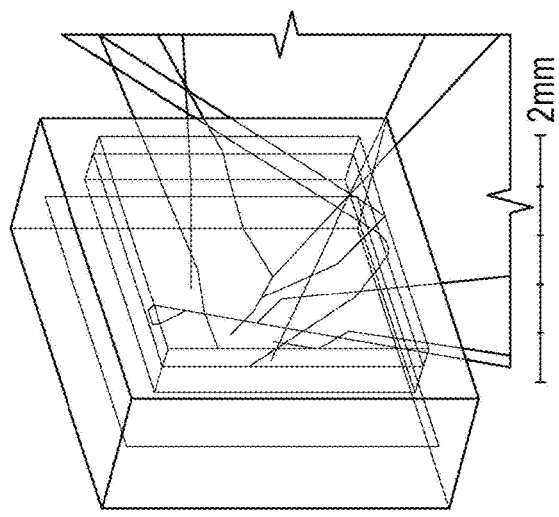
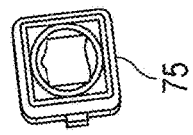
Fig. 39

Figs. 41a-d

Butt coupling SMT LED to fiber optic cable [bundle]

REMOTE PATHOGEN ERADICATION

This application takes priority from provisional patent applications: 63/017,407, filed Apr. 29, 2020; 63/044,641, filed Jun. 26, 2020; 63/077,003, filed Sep. 11, 2020; 63/118,638, filed Nov. 25, 2020; 63/139,294, filed Jan. 19, 2021; and 63/149,611, filed Feb. 15, 2021, the disclosures of which are entirely incorporated herein by reference thereto.

FIELD OF THE INVENTION

This invention relates to the remote destruction or eradication of pathogens such as viruses, bacteria, cancer and the like, where direct destruction is difficult or totally impeded, and in particular relates to pathogen eradicators such as radiation which is brought from outside a body into direct eradicating contact with pathogens within the body. The term eradicating as used herein is equivalent to inactivating and does not necessarily mean full destruction. In particular, this invention relates to the transmission of ultraviolet (UV) light, in the DNA/RNA disruption wave-length range, through a tangible transmission medium, with sufficient power for the effective killing of normally not accessible pathogens thereby and particularly to such transmission into human bodies for the killing of pathogens in vivo, and for the killing of pathogens in sanitization procedures of inaccessible or difficult to access infected sites or in applications requiring tightly controlled and focused application. This invention relates to maximizing the intensity of transmission of light from a widespread angle light source such as an LED through a transmitting media, such as a fiber optics cable, to an illumination target and in particular the maximizing of the power intensity of transmission of deep UV (UV-C to UV-B range) light with minimized attenuation and with maximized transmittable UV light power.

BACKGROUND

Pathogens such as viruses, when out in the open such as on surfaces are readily eradicated by various means such as by use of soap and water which disrupts the protective envelope of the viruses, or by alcohol at sufficient strength (generally above 70%) as in common hand sanitizers. UV light, particularly in the deep UV range of UV-C (effective wave lengths of from 200-280 nm) has been known for over a hundred years to be a very effective pathogen eradicator and a plethora of products utilize UV light for sanitization. A common feature for effectiveness of such pathogen eradicators is however the need for direct proximity. Once the pathogen is able to "hide" and become partially or completely inaccessible, effectiveness is greatly reduced and becomes a function of the degree the pathogen eradicator can safely be brought into the requisite direct proximity. UV light in the UV-B (280-315 nm) and part of the UV-A ranges 315-340 of the 315-400 range) also show pathogen eradication effectiveness but to a much lower extent.

Pathogens such as viruses, bacteria and even cancer generally have a safe haven within a body or host organism to replicate and do considerable damage including death of the host organism unless internally disrupted by chemical and biological moieties (e.g., drugs), excision of pathogen infected areas (surgery), or by radiation treatment.

UV disinfection with direct application (though often attenuated by distance) is in wide and recognized use such as with short wave ultraviolet lamps used effectively in settings such as hospitals. However, transmission of disinfecting UV light or even use thereof in humans has recently been widely derided.

US Patent Pub. No. 2016/0114185 (Lacey Mankin)

There is a plethora of literature and patent literature dealing with the use of UV light to treat various viral and bacterial infections within animal or human bodies, particularly in orifices and cavities within the bodies. A vast majority of such literature describes the introduction of UV light sources such as LEDs directly within the body. A US Patent Application with Pub. No. 2006/0195165 dated Aug. 31, 2006 by Michael Gertner (subsequently abandoned) exemplifies such treatment expedients. None of the literature, as far as is known, exemplifies an actual working device or remote positioning of actual existing UV light sources (of pathogen killing wavelength) outside a body and actual successful transmission of effectively treating UV light, especially in highly restricted or inaccessible sites.

A US patent application (subsequently abandoned), Pub. No. 2016/0114185, published on Apr. 28, 2016 by Lacey Mankin, describes the use of UV light to kill viral pathogens in a human or animal body by means of transmission of the UV light through the optical fibers of an endoscope. However, there is no teaching or any examples of an actual light UV light gathering from a UV light source or transmission and application of the UV light to a viral or bacterial target or of any structure or method of being able to transmit such UV light through the fibers with any degree of power to effectively kill pathogens in a single application or within a reasonable time period which would overcome any propensity of the pathogen to propagate faster than being eliminated by a minimal UV application. Optical fibers as used in endoscopes are generally highly susceptible to being degraded by deep UV by a process called "solarization" which effectively prevents any deep UV from being transmitted therethrough. Instead, the deep UV is totally absorbed by the fiber. In addition, though the patent application makes reference to UV light effectiveness in killing pathogens at levels of about 1.2 $mW/cm^2$ this is when the UV is applied directly without transmission, whereas transmission entails enormous if not entire loss of any UV light which may be output by a UV light source often even if the fiber is not solarized.

Despite the suggestion by Lacey Mankin in said abandoned patent application, it is the currently generally accepted belief, even among optical engineers, that it is not possible to successfully transmit deep UV light through a transmission medium such as fiber optic cables with any useful pathogenic treatment power output. Prior art studies have in fact experimentally shown that the amount of UV power necessary to disrupt or kill pathogens such as viruses and bacteria is much greater than the power and application method alluded to in said patent application even without the major power losses encountered with UV light transmission. The following are descriptions, and tables of prior art requirements for direct viral and bacterial UV treatment and in particular with exposed wound treatment (for purposes of this application, $mW/cm^2$ is essentially equivalent to mJoule or $mJ/cm^2$):

UV Light Treatment of Wounds, Pathogens with Power Requirements:

TABLE 1

Potential applications of ultraviolet phototherapy for wound care and skin disorders

| UV Phototherapy | UV Spectrum/Dosage | Types of Wounds/Skin Pathologies | Setting | Study Findings | Ref. |
|---|---|---|---|---|---|
| UVC | 254 nm; single radiant exposure of 2.59 J/cm$^2$ | Partial-thickness skin abrasion infected with *Pseudomonas aeruginosa* and *Staphylococcus aureus* | In vivo | Significantly reduced bacterial burden in the infected mouse wounds by 10-fold in comparison to untreated wounds; increased the survival rate of mice infected with highly virulent bacteria, and increased the wound-healing rate | 53 |
| UVC | 254 nm; single radiant exposure either with 2.92 or 6.48 J/cm$^2$ | Third-degree dermal burn wound infected with *Candida albicans* | In vivo | Significantly reduced fungal burden of infected burns by 96%-99%; superior to a topical antifungal drug, nystatin cream | 54 |
| UVC | 254 nm; a single 180 s treatment of UVC lamp, irradiation 15.64 mW/cm$^2$, placed 1 inch from the wound bed | 22 patients with chronic ulcers infected and critically colonized with bacteria | Clinical | UVC can kill bacteria such as *P. aeruginosa*, *S. aureus*, and methicillin-resistant *S. aureus* present in superficial layers of chronic wounds | 56 |
| UVC | 254 nm; treatment daily for 3 successive days with 15 or 60 mJ/cm$^2$ irradiation | Full-thickness dermal wounds | In vivo | At early stage of healing UVC treatment, at certain radiant exposure parameters promoted expression of TGF-β and bFGF in granulation tissues; beneficial for accelerating wound healing | 69, 70 |
| Combination of UVA, UVB, and UVC | UV light treatment two times per week | 16 patients suffering from superficial pressure sores; a randomized placebo-controlled trial | Clinical | UV-treated group, mean time to healing was 6.3 weeks vs. 8.4 weeks for placebo group | 76 |
| UVC | UV irradiation three times per week for 6 weeks | Exudative decubitus ulcers | Clinical | Significant reduction in the amount of exudates produced by the decubitus ulcers; and improvement in their appearance and depth | 77 |
| A combination of US and UVC treatment | US (3 MHz, 0.2 W/cm$^2$)/UVC (95% emission at 250 nm); applied five treatments weekly | Pressure ulcers in patients with spinal cord injury | Clinical | Combined US and UVC treatment was more effective on wound healing than nursing care alone or laser light therapy | 57 |
| Multimodel phototherapy combining LILT and UVC irradiation | LILT (820 nm, 140 mW/cm$^2$, 2 J/cm$^2$ and 660 nm, 120 mW/cm$^2$ and 4 J/cm$^2$) and UVC irradiation (95% emission at 250 nm, E1 dose for 15 s; and E3 dose for 90 s | Infected postoperative diabetic foot ulcer | Clinical | Infected wound healed completely, in 3-month follow-up period, there was no recurrence of the ulcer | 78 |
| UVA1 | 340-400 nm; medium dose = 40-80 J/cm$^2$; 15 exposures | Atopic dermatitis; randomized controlled trials | Clinical | Immunomodulatory effects, including apoptosis of infiltrating T-cells, suppression of cytokine levels, and reduction in Langerhans cell numbers | 79, 80 |
| UVA1 | 340-400 nm; medium dose = 40-80 J/cm$^2$ and/or high dose = 80-130 J/cm$^2$; 20-40 exposures | Localized scleroderma (morphea); randomized controlled trials | Clinical | Efficacy through increased production of MMP-1 and IFN-γ, and to a lesser extent by decreasing TGF-β and collagen production | 79, 81, 83 |
| NB UVB | 308 nm XeCl excimer laser and the 308 nm XeCl excimer lamp; lesions were treated twice weekly with the same dose; 24 sessions | Vitiligo; randomized monocentric study | Clinical | Two treatments showed similar results in terms of efficacy for a repigmentation of at least 50%; lamp induced more erythema than the laser | 86 |
| PUVA (8-methoxypsoralen plus UVA) and both NB and BB UVB | medium dose = 40-80 J/cm$^2$ and/or high dose = 80-130 J/cm$^2$; 20-40 exposures | Mycosis fungoides (cutaneous T-cell lymphoma); open studies | Clinical | Safe and effective treatment options for early stages of the disease | 87 |
| 308 nm XeCl laser treatment, PUVA, and combined UVA-UVB | Combined low-dose UVB, low-dose UVA, and visible light; intranasal phototherapy; randomized, double-blind study | Allergic rhinitis | Clinical | Effective in reducing symptom scores for sneezing, rhinorrhea, nasal itching, and the total nasal score in ragweed allergic patients, mechanism of action, it reduces the antigen presenting capacity of dendritic cells, induces apoptosis of immune cells, and inhibits synthesis and release of proinflammatory mediator from several cell types | 85 |

UV, ultraviolet; TGF, transforming growth factor; bFGF, basic fibroblast growth factor; LILT, low-intensity laser therapy; MMP-1, matrix metalloproteinase 1; IFN-γ, interferon gamma; NB, narrow band; XeCl, xenon chloride; BB, broad band.

gUV Dose Required to Achieve Incremental Log Inactivation of Bacteria, Protozoa and Viruses Revised and Expanded by: Gabriel Chevrefils, B. Ing, and Éric Caron, B. Sc. With earlier (1999) Contributions by: Harold Wright3 and Gail Sakamoto3 And with Peer Review by: Pierre Payment, Benoit Barbeau and Bill Cairns provides tables with UV dose effectives against specific bacteria and viruses with low (LP) and medium pressure (MP) mercury arc lamps, as indicated:

Notes:
Table 2—*Escherichia Coli* C LP (Low Pressure Mercury Lamp)
This most common bacteria is extremely sensitive to UV dose. A change in UV dose from 2 mJ/cm$^2$ to 10.7 mJ/cm$^2$, which is an 8 mJ increase in UV dose is all that is needed to produce a reduction in bacteria concentration from 1 Log to 7 Log, a change of 6 log. This is 1,000,000 times fewer *E. Coli!*
Table 4—Rotovirus with LP
This virus is much tougher. 20 mJ/cm$^2$ achieved the first 10× reduction.
Then to reduce that a further 1,000 times (3 log) took an additional 180 mJ/cm$^2$.

TABLE 1

UV Doses for Multiple Log Reductions for Various Spores

| Spore | Lamp Type | \multicolumn{7}{c}{UV Dose (Fluence) (mJ/cm$^2$) for a given Log Reduction without photo-reactivation} | Reference |
|---|---|---|---|---|---|---|---|---|---|
| | | 1 | 2 | 3 | 4 | 5 | 6 | 7 | |
| *Bacillus subtilis* ATCC6633 | N/A | 36 | 48.6 | 61 | 78 | | | | Chang et al. 1985 |
| *Bacillus subtilis* ATCC6633 | LP | 24 | 35 | 47 | 79 | | | | Mamane-Gravetz and Linden 2004 |
| *Bacillus subtilis* ATCC6633 | LP | 22 | 38 | >50 | | | | | Sommer et al. 1998 |
| *Bacillus subtilis* ATCC6633 | LP | 20 | 39 | 60 | 81 | | | | Sommer et al. 1999 |
| *Bacillus subtilis* WN626 | LP | 0.4 | 0.9 | 1.3 | 2 | | | | Marshall et al., 2003 |

TABLE 2

UV Doses for Multiple Log Reductions for Various Bacteria

| Bacterium | Lamp Type | 1 | 2 | 3 | 4 | 5 | 6 | 7 | Reference |
|---|---|---|---|---|---|---|---|---|---|
| *Aeromonas hydrophila* ATCC7966 | LP | 1.1 | 2.6 | 3.9 | 5 | 6.7 | 8.6 | | Wilson et al. 1992 |
| *Aeromonas salmonicida* | LP | 1.5 | 2.7 | 3.1 | 5.9 | | | | Liltved and Landfald 1996 |
| *Campylobacter jejuni* ATCC 43429 | LP | 1.6 | 3.4 | 4 | 4.6 | 5.9 | | | Wilson et al. 1992 |
| *Citrobacter diversus* | LP | 5 | 7 | 9 | 11.5 | 13 | | | Giese and Darby 2000 |
| *Citrobacter freundii* | LP | 5 | 9 | 13 | | | | | Giese and Darby 2000 |
| *Escherichia coli* ATCC 11229 | N/A | 2.5 | 3 | 3.5 | 5 | 10 | 15 | | Harris et al. 1987 |
| *Escherichia coli* ATCC 11229 | N/A | 3 | 4.8 | 6.7 | 8.4 | 10.5 | | | Chang et al. 1985 |
| *Escherichia coli* ATCC 11229 | LP | <5 | 5.5 | 6.5 | 7.7 | 10 | | | Zimmer et al. 2002 |
| *Escherichia coli* ATCC 11229 | MP | <3 | <3 | <3 | <3 | 8 | | | Zimmer et al. 2002 |
| *Escherichia coli* ATCC 11229 | LP | 7 | 8 | 9 | 11 | 12 | | | Hoyer 1998 |
| *Escherichia coli* ATCC 11229 | LP | 3.6 | 4.7 | 5.5 | 6.5 | 7.5 | 9.6 | | Sommer et al. 2000 |
| *Escherichia coli* ATCC 11229 | LP | 6 | 6.5 | 7 | 8 | 9 | 10 | | Sommer et al. 1998 |
| *Escherichia coli* ATCC 11303 | LP | 4 | 6 | 9 | 10 | 13 | 15 | 19 | Wu et al. 2005 |
| *Escherichia coli* ATCC 25922 | LP | 6 | 6.5 | 7 | 8 | 9 | 10 | | Sommer et al. 1998 |
| *Escherichia coli* C | LP | 2 | 3 | 4 | 5.6 | 6.5 | 8 | 10.7 | Otaki et al. 2003 |
| *Escherichia coli* O157:H7 | LP | 1.5 | 3 | 4.5 | 6 | | | | Tosa and Hirata 1999 |
| *Escherichia coli* O157:H7 | LP | <2 | <2 | 2.5 | 4 | 8 | 17 | | Yaun et al. 2003 |
| *Escherichia coli* O157:H7 CCUG 29193 | LP | 3.5 | 4.7 | 5.5 | 7 | | | | Sommer et al. 2000 |
| *Escherichia coli* O157:H7 CCUG 29197 | LP | 2.5 | 3 | 4.6 | 5 | 5.5 | | | Sommer et al. 2000 |
| *Escherichia coli* O157:H7 CCUG 29199 | LP | 0.4 | 0.7 | 1 | 1.1 | 1.3 | 1.4 | | Sommer et al. 2000 |
| *Escherichia coli* O157:H7 ATCC 43894 | LP | 1.5 | 2.8 | 4.1 | 5.6 | 6.8 | | | Wilson et al. 1992 |
| *Escherichia coli* O25:K98:NM | LP | 5 | 7.5 | 9 | 10 | 11.5 | | | Sommer et al. 2000 |
| *Escherichia coli* O26 | LP | 5.4 | 8 | 10.5 | 12.8 | | | | Tosa and Hirata 1999 |
| *Escherichia coli* O50:H7 | LP | 2.5 | 3 | 3.5 | 4.5 | 5 | 6 | | Sommer et al. 2000 |
| *Escherichia coli* O78:H11 | LP | 4 | 5 | 5.5 | 6 | 7 | | | Sommer et al. 2000 |
| *Escherichia coli* K-12 IFO3301 | LP & MP | 2 | 4 | 6 | 7 | 8.5 | | | Oguma et al. 2002 |
| *Escherichia coli* K-12 IFO3301 | LP & MP | 2.2 | 4.4 | 6.7 | 8.9 | 11.0 | | | Oguma et al. 2004 |
| *Escherichia coli* K-12 IFO3301 | LP | 1.5 | 2 | 3.5 | 4.2 | 5.5 | 6.2 | | Otaki et al. 2003 |
| *Escherichia coli* Wild type | LP | 4.4 | 6.2 | 7.3 | 8.1 | 9.2 | | | Sommer et al. 1998 |
| *Halobacterium elongata* ATCC33173 | LP | 0.4 | 0.7 | 1 | | | | | Martin et al. 2000 |
| *Halobacterium salinarum* ATCC43214 | LP | 12 | 15 | 17.5 | 20 | | | | Martin et al. 2000 |
| *Klebsiella pneumoniae* | LP | 12 | 15 | 17.5 | 20 | | | | Giese and Darby 2000 |

TABLE 2-continued

UV Doses for Multiple Log Reductions for Various Bacteria

| Bacterium | Lamp Type | \multicolumn{7}{c}{UV Dose (Fluence) (mJ/cm$^2$) for a given Log Reduction without photo-reactivation} | Reference |
|---|---|---|---|---|---|---|---|---|---|
| | | 1 | 2 | 3 | 4 | 5 | 6 | 7 | |
| *Klebsiella terrigena* ATCC33257 | LP | 4.6 | 6.7 | 8.9 | 11 | | | | Wilson et al. 1992 |
| *Legionella pneumophila* ATCC 43660 | LP | 3.1 | 5 | 6.9 | 9.4 | | | | Wilson et al. 1992 |
| *Legionella pneumophila* ATCC33152 | LP | 1.6 | 3.2 | 4.8 | 6.4 | 8.0 | | | Oguma et al. 2004 |
| *Legionella pneumophila* ATCC33152 | MP | 1.9 | 3.8 | 5.8 | 7.7 | 9.6 | | | Oguma et al. 2004 |
| *Pseudomonas stutzeri* | UVB | 100 | 150 | 195 | 230 | | | | Joux et al. 1999 |
| RB2256 | UVB | 175 | >300 | | | | | | Joux et al. 1999 |
| *Salmonella* spp. | LP | <2 | 2 | 3.5 | 7 | 14 | 29 | | Yaun et al. 2003 |
| *Salmonella anatum* (from human feces) | N/A | 7.5 | 12 | 15 | | | | | Tosa and Hirata 1998 |
| *Salmonella derby* (from human feces) | N/A | 3.5 | 7.5 | | | | | | Tosa and Hirata 1998 |
| *Salmonella enteritidis* (from human feces) | N/A | 5 | 7 | 9 | 10 | | | | Tosa and Hirata 1998 |
| *Salmonella infantis* (from human feces) | N/A | 2 | 4 | 6 | | | | | Tosa and Hirata 1998 |
| *Salmonella typhi* ATCC 19430 | LP | 1.8 | 4.8 | 6.4 | 8.2 | | | | Wilson et al. 1992 |
| *Salmonella typhi* ATCC 6539 | N/A | 2.7 | 4.1 | 5.5 | 7.1 | 8.5 | | | Chang et al. 1985 |
| *Salmonella typhimurium* (from human feces) | N/A | 2 | 3.5 | 5 | 9 | | | | Tosa and Hirata 1998 |
| *Salmonella typhimurium* (from human feces) | N/A | 2 | 3.5 | 5 | 9 | | | | Tosa and Hirata 1998 |
| *Salmonella typhimurium* (in act sludge) | LP | 3 | 11.5 | 22 | 50 | | | | Maya et al. 2003 |
| *Salmonella typhimurium* | UVB | 50 | 100 | 175 | 210 | 250 | | | Joux et al. 1999 |
| *Shigella dysenteriae* ATCC29027 | LP | 0.5 | 1.2 | 2 | 3 | 4 | 5.1 | | Wilson et al. 1992 |
| *Shigella sonnei* ATCC9290 | N/A | 3.2 | 4.9 | 6.5 | 8.2 | | | | Chang et al. 1985 |
| *Staphylococcus aureus* ATCC25923 | N/A | 3.9 | 5.4 | 6.5 | 10.4 | | | | Chang et al. 1985 |
| *Streptococcus faecalis* ATCC29212 | N/A | 6.6 | 8.8 | 9.9 | 11.2 | | | | Chang et al. 1985 |
| *Streptococcus faecalis* (secondary effluent) | N/A | 5.5 | 6.5 | 8 | 9 | 12 | | | Harris et al. 1987 |
| *Vibrio anguillarum* | LP | 0.5 | 1.2 | 1.5 | 2 | | | | Liltved and Landfald 1996 |
| *Vibrio cholerae* ATCC25872 | LP | 0.8 | 1.4 | 2.2 | 2.9 | 3.6 | 4.3 | | Wilson et al. 1992 |
| *Vibrio natriegens* | UVB | 37.5 | 75 | 100 | 130 | 150 | | | Joux et al. 1999 |
| *Yersinia enterocolitica* ATCC27729 | LP | 1.7 | 2.8 | 3.7 | 4.6 | | | | Wilson et al. 1992 |
| *Yersinia ruckeri* | LP | 1 | 2 | 3 | 5 | | | | Liltved and Landfald 1996 |

TABLE 3

UV Doses for Multiple Log Reductions for Various Protozoa

| Protozoan | Lamp Type | \multicolumn{7}{c}{UV Dose (Fluence) (mJ/cm$^2$) for a given Log Reduction without photo-reactivation} | Reference |
|---|---|---|---|---|---|---|---|---|---|
| | | 1 | 2 | 3 | 4 | 5 | 6 | 7 | |
| *Cryptosporidium hominis* | LP & MP | 3 | 5.8 | | | | | | Johnson et al. 2005 |
| *Cryptosporidium parvum*, oocysts, tissue culture assay | N/A | 1.3 | 2.3 | 3.2 | | | | | Shin et al. 2000 |
| *Cryptosporidium parvum* | LP & MP | 2.4 | <5 | 5.2 | 9.5 | | | | Craik et al. 2001 |
| *Cryptosporidium parvum* | MP | <5 | <5 | <5 | −6 | | | | Amoah et al. 2005 |
| *Cryptosporidium parvum* | MP | <10 | <10 | <10 | | | | | Belosevic et al. 2001 |
| *Cryptosporidium parvum* | LP | 1 | 2 | <5 | | | | | Shin et al. 2001 |
| *Cryptosporidium parvum* | MP | 1 | 2 | 2.9 | 4 | | | | Bukhari et al. 2004 |
| *Cryptosporidium parvum* | LP | <2 | <2 | <2 | <4 | <10 | | | Clancy et al. 2004 |
| *Cryptosporidium parvum* | MP | <3 | <3 | 3-9 | <11 | | | | Clancy et al. 2000 |
| *Cryptosporidium parvum* | LP | <3 | <3 | 3-6 | <16 | | | | Clancy et al. 2000 |
| *Cryptosporidium parvum* | LP | 0.5 | 1 | 1.4 | 2.2 | | | | Morita et al. 2002 |
| *Cryptosporidium parvum* | LP | 2 | <3 | <3 | | | | | Zimmer et al. 2003 |
| *Cryptosporidium parvum* | MP | <1 | <1 | <1 | | | | | Zimmer et al. 2003 |
| *Encephalitozoon cuniculi*, microsporidia | LP | 4 | 9 | 13 | | | | | Marshall et al. 2003 |
| *Encephalitozoon hellem*, microsporidia | LP | 8 | 12 | 18 | | | | | Marshall et al. 2003 |

TABLE 3-continued

UV Doses for Multiple Log Reductions for Various Protozoa

| Protozoan | Lamp Type | UV Dose (Fluence) (mJ/cm$^2$) for a given Log Reduction without photo-reactivation | | | | | | | Reference |
|---|---|---|---|---|---|---|---|---|---|
| | | 1 | 2 | 3 | 4 | 5 | 6 | 7 | |
| *Encephalitozoon intestinalis*, microsporidia | LP & MP | <3 | 3 | <6 | 6 | | | | Huffman et al. 2002 |
| *Encephalitozoon intestinalis*, microsporidia | LP | 3 | 5 | 6 | | | | | Marshall et al. 2003 |
| *Giardia lamblia*, gerbil infectivity assay | LP | <0.5 | <0.5 | <0.5 | <1 | | | | Linden et al. 2002b |
| *Giardia lamblia* | LP | <10 | -10 | <20 | | | | | Campbell et al. 2002 |
| *Giardia lamblia* | LP | <2 | <2 | <4 | | | | | Mofidi et al. 2002 |
| *Giardia lamblia*, excystation assay | N/A | >63 | | | | | | | Rice and Hoff 1981 |
| *Giardia lamblia*, excystation assay | N/A | 40 | 180 | | | | | | Karanis et al. 1992 |
| *Giardia muris*, excystation assay | N/A | 77 | 110 | | | | | | Carlson et al. 1985 |
| *G. muris*, cysts, mouse infectivity assay | N/A | <2 | <6 | | 10 + tailing | | | | Craik et al. 2000 |
| *Giardia muris* | MP | 1 | 4.5 | | 28 + tailing | | | | Craik et al. 2000 |
| *Giardia muris* | MP | <10 | <10 | <25 | -60 | | | | Belosevic et al. 2001 |
| *Giardia muris* | LP | <1.9 | <1.9 | -2 | -2.3 | | | | Hayes et al. 2003 |
| *Giardia muris* | LP | <2 | <2 | <4 | | | | | Mofidi et al. 2002 |
| *G. muris*, cysts | MP | <5 | <5 | 5 | | | | | Amoah et al. 2005 |

TABLE 4

UV Doses for Multiple Log Reductions for Various Viruses

| Virus | Host | Lamp Type | UV Dose (Fluence) (mJ/cm$^2$) per Log Reduction | | | | | | Reference |
|---|---|---|---|---|---|---|---|---|---|
| | | | 1 | 2 | 3 | 4 | 5 | 6 | |
| PRD-1 (Phage) | *S. typhimurium* Lt2 | N/A | 9.9 | 17.2 | 23.5 | 30.1 | | | Meng and Gerba 1996 |
| B40-8 (Phage) | *B. Fragilis* | LP | 11 | 17 | 23 | 29 | 35 | 41 | Sommer et al. 2001 |
| B40-8 (Phage) | *B. fragilis* HSP-40 | LP | 12 | 18 | 23 | 28 | | | Sommer et al. 1998 |
| MS2 (Phage) | *Salmonella typhimurium* WG49 | N/A | 16.3 | 35 | 57 | 83 | 114 | 152 | Nieuwstad and Havelaar 1994 |
| MS2 DSM 5694 (Phage) | *E. coli* NCIB 9481 | N/A | 4 | 16 | 38 | 68 | 110 | | Wiedenmann et al. 1993 |
| MS2 ATCC 15977-B1 (Phage) | *E. coli* ATCC 15977-B1 | LP | 15.9 | 34 | 52 | 71 | 90 | 109 | Wilson et al. 1992 |
| MS2 NCIMB 10108 (Phage) | *Salmonella typhimurium* WG49 | N/A | 12.1 | 30.1 | | | | | Tree et al. 1997 |
| MS2 (Phage) | *E. coli* K-12 Hfr | LP | 21 | 36 | | | | | Sommer et al. 1998 |
| MS2 (Phage) | *E. coli* CR63 | N/A | 16.9 | 33.8 | | | | | Rauth 1965 |
| MS2 (Phage) | *E. coli* 15977 | N/A | 13.4 | 28.6 | 44.8 | 61.9 | 80.1 | | Meng and Gerba 1996 |
| MS2 (Phage) | *E. coli* C3000 | N/A | 35 | | | | | | Battigelli et al. 1993 |
| MS2 (Phage) | *E. coli* ATCC 15597 | N/A | 19 | 40 | 61 | | | | Oppenheimer et al. 1993 |
| MS2 (Phage) | *E. coli* C3000 | LP | 20 | 42 | 69 | 92 | | | Batch et al. 2004 |
| MS2 (Phage) | *E. coli* ATCC 15597 | LP | 20 | 42 | 70 | 98 | 133 | | Lazarova and Savoye 2004 |
| MS2 (Phage) | *E. coli* ATCC 15977 | LP | 20 | 50 | 85 | 120 | | | Thurston-Enriquez et al., 2003 |
| MS2 (Phage) | *E. coli* HS(pFamp)R | LP | | 45 | 75 | 100 | 125 | 155 | Thompson et al. 2003 |
| MS2 (Phage) | *E. coli* C3000 | LP | 20 | 42 | 68 | 90 | | | Linden et al. 2002a |
| MS2 (Phage) | *E. coli* K-12 | LP | 18.5 | 36 | 55 | | | | Sommer et al. 2001 |
| MS2 (Phage) | *E. coli* NCIMB 9481 | N/A | 14 | | | | | | Tree et al. 2005 |
| PHI X 174 (Phage) | *E. coli* WG5 | LP | 2.2 | 5.3 | 7.3 | 10.5 | | | Sommer et al. 1998 |
| PHI X 174 (Phage) | *E. coli* C3000 | N/A | 2.1 | 4.2 | 6.4 | 8.5 | 10.6 | 12.7 | Battigelli et al. 1993 |
| PHI X 174 (Phage) | *E. coli* ATCC15597 | N/A | 4 | 8 | 12 | | | | Oppenheimer et al. 1993 |
| PHI X 174 (Phage) | *E. coli* WG 5 | LP | 3 | 5 | 7.5 | 10 | 12.5 | 15 | Sommer et al. 2001 |
| PHI X 174 (Phage) | *E. coli* ATCC 13706 | LP | 2 | 3.5 | 5 | 7 | | | Giese and Darby 2000 |
| *Staphylococcus aureus* phage A 994 (Phage) | *Staphylococcus aureus* 994 | LP | 8 | 17 | 25 | 36 | 47 | | Sommer et al. 1989 |
| Calicivirus canine | MOCK cell line | LP | 7 | 15 | 22 | 30 | 36 | | Husman et al. 2004 |
| Calicivirus feline | CRFK cell line | LP | 7 | 16 | 25 | | | | Husman et al. 2004 |
| Calicivirus feline | CRFK cell line | N/A | 4 | 9 | 14 | | | | Tree et al. 2005 |
| Calicivirus feline | CRFK cell line | LP | 5 | 15 | 23 | 30 | 39 | | Thurston-Enriquez et al. 2003 |
| Adenovirus type 2 | A549 cell line | LP | 20 | 45 | 80 | 110 | | | Shin et al. 2005 |
| Adenovirus type 2 | Human lung cell line | LP | 35 | 55 | 75 | 100 | | | Ballester and Malley 2004 |
| Adenovirus type 2 | PLC/PRF/5 cell line | LP | 40 | 78 | 119 | 160 | 195 | 235 | Gerba et al. 2002 |

TABLE 4-continued

UV Doses for Multiple Log Reductions for Various Viruses

| | | Lamp | UV Dose (Fluence) (mJ/cm$^2$) per Log Reduction | | | | | | |
|---|---|---|---|---|---|---|---|---|---|
| Virus | Host | Type | 1 | 2 | 3 | 4 | 5 | 6 | Reference |
| Adenovirus type 15 | A549 cell line (ATCC CCL-185) | LP | 40 | 80 | 122 | 165 | 210 | | Thompson et al. 2003 |
| Adenovirus type 40 | PLC/PRF/5 cell line | LP | 55 | 105 | 155 | | | | Thurston-Enriquez et al. 2003 |
| Adenovirus type 40 | PLC/PRF/5 cell line | LP | 30 | ND | ND | 124 | | | Meng and Gerba 1996 |
| Adenovirus type 41 | PLC/PRF/5 cell line | LP | 23.6 | ND | ND | 111.8 | | | Meng and Gerba 1996 |
| Poliovirus Type 1 ATCC Mahoney | N/A | N/A | 6 | 14 | 23 | 30 | | | Harris et al. 1987 |
| Poliovirus Type 1 LSc2ab ( ) | MA104 cell | N/A | 5.6 | 11 | 16.5 | 21.5 | | | Chang et al. 1985 |
| Poliovirus Type 1 LSc2ab | BGM cell | LP | 5.7 | 11 | 17.6 | 23.3 | 32 | 41 | Wilson et al. 1992 |
| Poliovirus 1 | BGM cell line | N/A | 5 | 11 | 18 | 27 | | | Tree et al. 2005 |
| Poliovirus 1 | CaCo2 cell-line (ATCC HTB37) | LP | 7 | 17 | 28 | 37 | | | Thompson et al. 2003 |
| Poliovirus 1 | BGM cell line | LP | 8 | 15.5 | 23 | 31 | | | Gerba et al. 2002 |
| Poliovirus Type Mahoney | Monkey kidney cell line Vero | LP | 3 | 7 | 14 | 40 | | | Sommer et al. 1989 |
| Coxsackievirus B5 | Buffalo Green Monkey cell line | N/A | 6.9 | 13.7 | 20.6 | | | | Battigelli et al. 1993 |
| Coxsackievirus B3 | BGM cell line | LP | 8 | 16 | 24.5 | 32.5 | | | Gerba et al. 2002 |
| Coxsackievirus B5 | BGM cell line | LP | 9.5 | 18 | 27 | 36 | | | Gerba et al. 2002 |
| Reovirus-3 | Mouse L-60 | N/A | 11.2 | 22.4 | | | | | Rauth 1965 |
| Reovirus Type 1 Lang strain | N/A | N/A | 16 | 36 | | | | | Harris et al. 1987 |
| Rotavirus SA-11 | Monkey kidney cell line MA 104 | LP | 8 | 15 | 27 | 38 | | | Sommer et al. 1989 |
| Rotavirus SA-11 | MA-104 cell line | N/A | 7.6 | 15.3 | 23 | | | | Battigelli et al. 1993 |
| Rotavirus SA-11 | MA-104 cell line | N/A | 7.1 | 14.8 | 25 | | | | Chang et al. 1985 |
| Rotavirus SA-11 | MA-104 cell line | LP | 9.1 | 19 | 26 | 36 | 48 | | Wilson et al. 1992 |
| Rotavirus | MA104 cells | LP | 20 | 80 | 140 | 200 | | | Caballero et al. 2004 |
| Hepatitis A HM175 | FRhK-4 cell | LP | 5.1 | 13.7 | 22 | 29.6 | | | Wilson et al. 1992 |
| Hepatitis A | HAV/HFS/GBM | N/A | 5.5 | 9.8 | 15 | 21 | | | Wiedenmann et al. 1993 |
| Hepatitis A HM175 | FRhK-4 cell | N/A | 4.1 | 8.2 | 12.3 | 16.4 | | | Battigelli et al. 1993 |
| Echovirus I | BGM cell line | LP | 8 | 16.5 | 25 | 33 | | | Gerba et al. 2002 |
| Echovirus II | BGM cell line | LP | 7 | 14 | 20.5 | 28 | | | Gerba et al. 2002 |

Thus, the overwhelming problem with effective application of transmitted UV light is being able to apply sufficiently highly powered, and more specifically UV-C light to kill pathogens at a meaningful rate and within a reasonable time. Deep UV light in the DNA/RNA disruption range is highly susceptible to attenuation during transmission and will seek every opportunity to become absorbed in transmission media or to otherwise be severely restricted in uptake for transmission. Transmission losses for applications as disclosed in said patent application would likely be on the order of more than 95% of light which makes it into optical fibers of the endoscope (significantly less that the amount of light emitted from a light source as will be described) and even complete loss, with a distal power output from existing UV light sources measurable in low microwatts per cm$^2$, if any at all. This is a generally ineffective application of UV light against a pathogen in a reasonable time period, as evidenced by the above tables, and probably less than the rate at which a human body (even with an overwhelmed immune response) is able to kill pathogens.

UV-C light is normally attenuated out of effective use with directed transmission and, in fact, will often corrosively attack the very media through which it is transmitted and even the normally used fiber optics of endoscopes in the destructive process known as solarization. To make matters even more untenable for utilizing UV-C light for disinfection such as in a human body, sources for pure emitted UV-C light in the desired and optimal 265 nm range for DNA/RNA disruption, have been confined to pulsed xenon and mercury bulbs (with overall UV power outputs at specific wave lengths being on the order of no more than about 4 mW/cm$^2$). Even currently produced UV emitting LEDs and lasers have inherent very low efficiencies and very low direct output power, measured in the low milliwatt ranges.

It is thus very difficult to provide UV-C light with enough transmitted power (with pathogen killing application power being measured in millijoules rather than microjoules or microwatts per cm$^2$ of area), especially when further attenuated by transmission losses, to effectively kill pathogens, except after extended periods of exposure time (if at all), often measured in hours and even days (depending on various common factors such as the extent of area to be disinfected). This is very problematic in applications requiring limited time parameters such as in vivo treatments such as endoscopies and where immediate effective treatment is vital.

An additional problem of UV light transmission is the initial need for efficient collection of the UV light from the generating sources (often widely scattered) into a transmission medium and then into a proper acceptance angle which allows for transmission rather than absorption into the walls or cladding of the transmission medium. A still further problem is that inaccessible or difficult to access sites are often of minimal dimension requiring that widely collected light be focused down into such minimal dimensions. However, light and particularly UV light is not amenable to compression and further power losses are inevitably sustained prior to any light emission application.

It should also be understood that UV light sources such as LEDs and certainly xenon and mercury lamp sources are of dimensions generally too large to be effectively brought into direct proximity with the inaccessible or difficult to access sites or areas such as within the human body. Much of the literature and patent literature accordingly entails the direct insertion of the UV light sources into the body and has thus been restricted to accessible orifices and relatively large cavities within the body.

Furthermore, UV light sources are very highly inefficient (e.g., currently available 265 nm LEDs have no more than a 1.5% maximum efficiency). Accordingly, they generate high amounts of heat which can be quite detrimental to surrounding biological or other delicate materials adjacent thereto. Some literature recognizes this problem and makes provision for heat removal. However, effective heat sinks only add increased bulk making such UV light sources even less amenable to direct placement adjacent infected sites particularly of restricted access and small dimensions.

Xenon arc lamps and mercury bulbs, traditionally used as a UV-C source, are not confined to a single spectrum but emit light over a wide spectrum range with the actual power for each part of the light spectrum, in a pathogen killing range, such as at 265 nm, being just as low or lower than that of single spectrum LEDs and lasers. Available power output for newly available LEDs (with efficiencies in the 1-1.5% range) do not normally effectively exceed the 40 mW range with a 4-watt input, with lasers having even lower power output, with much larger and more costly devices. Standard light transmitting media such as optical fibers, often, even if formulated to be resistant to environmental UV degradation, depending on length, can lose 95% or more of output power in 1-2 meter lengths (as a minimum required for endoscopic transmission) as an immediate power loss. Sufficient power is thus generally unavailable for UV light treatment of internally situated pathogens in a reasonable period of time (measured in seconds or even under a minute and a maximum of several minutes to a half hour/exposure site, to avoid extreme patient discomfiture or possible UV-C cell damage). Effective reasonable time for pathogen treatment, as is evident from prior art studies, generally requires an effective minimum of about 2-20 mW per square centimeter, at a distance of at most 35-50 mm for most viral pathogens.

A recent study and presentation of the effect of deep UV light on pathogens by the IEEE of Tech Talk Semiconductors Optoelectronics on 16 Apr. 2020, entitled *Ultraviolet-LED Maker Demonstrates* 30 *Second Coronavirus Kill* presented by Seoul Viosys and authored by Samuel K. Moore, provides a rough basis for determining the parameters of UV light (wave-length, application distance, applied power and duration) needed to have a disruptive effect on pathogens. The study provided the results of the direct (not transmitted) output of a non-optimal 275 nm LED on viral cells (coronavirus) with the conclusion that the virus was effectively killed in 30 seconds, with an output power of about 20 mW/cm$^2$ at a distance of 1.5 cm. As a result of the inverse square rule, closer distances will dramatically increase applied power.

It is also noted that 275 nm UV light is about 25% less effective as compared to 265 nm UV light in killing viral pathogens. Furthermore, it is actual pathogen applied power rather than initially generated power which is the controlling factor in virus or other pathogen disruption and often these differ widely, as a result of losses in the transmission.
US Patent Publication No. 2019/0175938 (Cedar Sinai)

In view of such deficiencies, and the need for extended exposure periods, the trend, such as described in current published research also includes use of UV-A light being introduced into patients via fixed in place catheter devices containing UV emitting LEDs (without UV light being transmitted through a transmission medium) for extended periods of time to safely kill viruses in the patients. Cedar Sinai Hospital, is using such emplaced devices for killing internal pathogens, with light sources in the higher end of the UV scale such as in the UVB (280 nm-315 nm) and UV-A (315 nm-400 nm—with wavelengths above 340 nm having effectively little or no pathogen killing effect) ranges which generally are considered to be less harmful to healthy cells. These light sources, though possibly having greater output power, are, however, much less efficient in pathogen disruption with unacceptably long exposure times often being required and, contrary to be belief, may actually be more harmful because of greater tissue penetration. The Cedar Sinai treatments require multiple dose sessions over days for extended dose time per session with complete and continuous anesthetization of patients.

The system involving the use of UV-A and UV-B light with internal in vivo delivery via a tube (catheter) supplied with a string of UV emitting LEDs is described in US Patent Publication No. 2019/0175938 assigned to Cedar-Sinai Hospital. The internal placement of electrical components such as electrically powered LEDs is however not desirable and the UV-A and UV-B lights, while relatively safer than UV-C lights, are much less effective in pathogen eradication, requiring extensive application time periods.

UV in vitro treatment of infected blood has also been used to kill bacteria but with treatment outside of patients, with the disinfected blood returned to human patients.

UV Light Scatter, Absorption and Collection:

Except for laser light which is highly coherent and focused, most visible light sources emit light in a conical penumbra of about 120-130° (LEDs) or in a greater than 180° emission ranges (light bulbs). In areas requiring greater areal illumination, the latter are desired. For more focused use such as flashlights, a lighting element bulb is situated in a generally conical reflective mirrored surface which roughly collimates light in a narrower angular emission range. Specialized lenses serve to refract or focus light, as desired. Such lighting manipulation is readily possible with visible light. If powered focused light is required for specific purposes, coherent visible laser light is readily available with significant power output. Even with the common collimation methods, a significant amount of the white light is lost when the light is transmitted through a light transmission medium such as fiber optics which have specific angles at which they are able to accept only a portion of the light being introduced into the fiber ends. This disadvantage is generally overcome to some degree by increasing the lumen output from the light source so that the eventual output provides sufficient illumination despite severe losses from the input light.

Non-visible light, particularly in the UV spectrum range, and more specifically in the UV-C and UV-B range (deep UV), are not so easily controllable in terms of emission range and power output and input power is not easily raised. Such light is widely scattered, substantially more than white visible light and is further highly prone to absorption with even more significant losses in transmission. To exacerbate problems with deep UV light transmission, light sources for deep UV light are currently available only in low microwatt and low milliwatt power levels. Even laser diode light sources provide no more than milliwatt outputs with bulky and costly equipment. Mercury lamps and xenon bulbs, with broad spectrum emissions, the common sources for deep UV light, need to be pulsed for such use and provide similar low power levels at specific UV wave lengths. UV LEDs are currently available but with outputs in the low milliwatt range (generally no more than about 40 mW).

Since deep UV is invisible, its useful applications are generally confined to power applications, such as direct areal disinfections, and with respect to instrument spectroscopic detections. Transmission of UV light through transmission media has inevitably resulted in initial almost complete if not complete loss in effective capture of emitted UV light and then in attenuation transmission losses caused by the transmission media and/or by collimating or focusing lenses and reflectors and by minimal light uptake angles into the transmitting media. Emitted power losses on the order of 95 percent or more have rendered medium-transmitted deep UV light, already at low input power levels, to be relatively useless for disinfection purposes, which require higher output power levels for practical utilization. Though low UV attenuation fiber cables are available, their practical use has been retarded by the practical inability of their UV uptake limiting angle to initially accept sufficient UV light from a power source. Fiber cables with relatively high UV light uptake are however composed of materials which rapidly degrade with exposure to deep UV light and either degrade immediately or have very short useful lifetimes, with high attenuation. As far as is known, deep UV light in the DNA/RNA wavelength region has never been effectively done with any usefully emitted UV with effective power levels. Accordingly, UV light disinfection applications have almost entirely involved direct application of disinfecting UV light to air, water and other materials and surfaces. Transmission of UV light for non-disinfecting purposes such as with borescopes has only been of readily transmittable non-deep UV-A light wavelengths having little or no power requirements.

Pathogen Sterilization:

In an application of sterilization and removal of pathogens, medical equipment absolutely requires stringent sanitation and sterilization to prevent dangerous infections with repeated use of the medical equipment with stringent FDA requirements. Common methods of sterilization include autoclaving with hot steam, and the use of sterilization liquids, often of a harsh and toxic nature. Each of these methods entail significant drawbacks. Studies have shown, that, except in very limited applications, UV based sterilization is highly detrimental to common polymeric medical equipment and in particular endoscopes.

Autoclaving with steam is very time consuming and restricts the time during which medical instruments are available for continuous use and is usually confined to use with UV resistant metal instruments. Common UV sterilization in a sterilization chamber bathed in UV light is restricted by material compatibility with UV rays and with inability of the light to access interior sites. Sterilization liquids, while effective, require rigorous and lengthy procedures and are often unable to reliably access interior sites highly prone to infectious materials such as biopsy and suction channels of endoscopes and further require fastidious full removal of the liquid chemicals since even slight residues can produce toxic effects.

A common instrument requiring stringent sterilization is a flexible endoscope such as a bronchoscope used for pulmonary examination. Endoscopes, which actually enter the body, can be primary sources of infection with inadequate sterilization having recently been the source of a series of infectious outbreaks resulting from inadequately removed resistant organisms.

Autoclaving, aside from limiting use time (sterilization times are often in excess of 30 minutes), may, with generated heat and steam, affect the polymers which comprise the structure of endoscopes, with possible device deformation and degradation. These same polymers are also susceptible to UV damage with yellowing and brittleness. Accordingly, endoscopes are most often sterilized with a disinfecting chemical such as ethylene oxide or series of chemical treatments. While the chemicals are easily effectively removed from the exterior of the endoscope in baths, after completion of disinfection, interior sections of the endoscope often present a challenge for complete sterilization and chemical removal. As a result, toxic residue may inadvertently remain, and resistant organisms may linger in interior areas of the endoscopes.

A primary internal area of an endoscope with restricted access and with high susceptibility to containment of microorganisms is the biopsy/suction or instrument channel through which biopsy samples are drawn during endoscopic procedures. Typical dimensions of a biopsy/suction or instrument insertion channel of an endoscope are about 2.2-3.7 mm ID by 500 mm length. The very narrow cross section and relatively long length present unique sterilization challenges exacerbated by surface tension resistance for cleaning liquids with restriction of liquid access, possible areas of air occlusion and the like with real possibilities of incomplete sterilization and cleaning chemical liquid removal. Other restricted access areas in an endoscope also include water and air introduction channels which have even narrower ID diameters, on the order of about 1 mm ID.

Implanted medical devices such as pacemakers and medication infusers and the like must be surgically removed for disinfection and then reimplanted with attendant medical complications and expense.

In a related non-medical aspect, certain non-medical applications such as with fluid carrying pipes and conduits, cracks and crevices, particularly in moist environments such as bathrooms, various noxious growth and pathogens flourish. However, because of inaccessibility of the areas having the growths and pathogens (this is often the very reason for the growths being prevalent) cleaning is often carried out, if at all, with mechanical propelled pigs (with cleaning elements) of sized insertion dimensions in pipes and with thin tools such as brushes but without any real disinfection. Use of flushing sanitizing chemicals in sufficient sanitizing quantities in large areas is generally very expensive, and the chemicals are difficult to completely remove especially from lengthy pipes or conduits.

SUMMARY

It is an object of the invention to provide a method and device which enables pathogen-killing UV light and particularly UV-C light to be transmitted through a controllably positionable transmission medium with a power output sufficient to kill pathogens in an inaccessible or difficult to access area or with highly direct focus, within a reasonable (depending on the application) time period.

It is a further object of the invention to provide a method and device for collecting UV light from a UV light emitting source coupled with collimating and focusing elements to provide a transmitted UV light of sufficient output power to kill pathogens within the reasonable time period.

It is yet another object of the invention to provide such emitted pathogen killing UV for sanitization of medical devices such as endoscopes.

It is another object of the invention to provide a method and device for the transmission of pathogen killing UV light for use in elimination of mold and mildew or other noxious biological organisms.

It is still yet another object of the invention to provide a method and device which directs pathogen killing UV light through controllably positionable tangible transmission elements such as optical fibers carried via standard endoscopes, EBUS or similar aspiration needles such as EUS, or other medically acceptable body insertion devices capable of carrying and directing the transmission elements as UV light transmission carriers into close proximity with and even within pathogen infected sites and to safely transmit UV light directly into organs or pathogen infected areas of a human body with sufficient power to kill pathogens including viruses, bacteria and cancer cells. Implanted medical devices, if resistant to UV light degradation, can also be sterilized in situ.

It is yet a further object to provide a method and device, for safe positioning and transmission of the pathogen killing UV light into the nose, ears, throat and genitalia of humans for treatment of pathogens contained therein.

It is an additional object to provide a method and device for sanitization or disinfection of air and water by transmission of UV light therethrough such as in swimming pools or enclosed vehicles.

In several co-pending applications, and, as described hereinafter, various structures, devices and methods are described for the bringing of UV light and particularly in the UV-C light wavelength region and most particularly in the 265 nm (260-270 nm) wavelength range, which is the most efficacious for destroying DNA/RNA of pathogens, such as viruses, bacteria, cancer and the like, safely and directly into human bodies, i.e., in vivo in close direct proximity to pathogen infected (or possibly infected) areas. Other co-pending applications describe the bringing of UV light into inaccessible or difficult to access sites or areas for killing of pathogens for sanitization purposes. Pathogens, as defined for the present application, encompasses all DNA/RNA containing unhealthy items including viruses, bacteria, cancer, mold, mildew and the like, susceptible to UV light disruption, with areas containing such pathogens being referred to herein as infected sites or areas.

It is an additional object of the present invention to provide a light transmission method and device structure which significantly minimizes light power losses, particularly for white LED light with a wide angle of emission and more particularly to LEDs emitting in the deep UV wavelength range.

It is a further object of the invention to provide a method and device which significantly increases deep UV angular uptake from a UV emitting LED into a UV light transmitting medium with increased UV power output with useful UV light disinfecting capability particularly in normally non readily accessible UV treatment areas.

The "reasonable time" parameter is generally dependent on exigent circumstances such as life-threatening severe infections, patient and medical personnel inconvenience as well as need for rapid turnover and need for re-use of medical equipment and reduction of incidents of incomplete disinfection. Generally, reasonable time for specific application is ideally within seconds and no more than several minutes to about a half hour per UV light application site for applications requiring treatment in multiple areas. For applications, entailing fixed positioning, factors of anesthetic effect duration, degree of infection, available application power and distance and the like are factors in determining medically justified reasonable time. Except in severe instances, the application time (or repeated procedures) should not exceed times which result in healthy cell damage greater than justified by pathogen removal.

Generally, in embodiments of the invention a method and device for effecting the method comprises the collection and effective transmission of pathogen killing UV light from a UV light source, such as a high powered 75 mW or more LED, through a tangible transmission medium, such as a low UV attenuation fiber cable (with db losses of no more than about 3 per meter length), which is at least initially resistant to degradation by the UV light. An interface between the UV light source and the tangible transmission medium is sufficiently efficient whereby collected and transmitted UV light is of an initially sufficiently high power level such that with attenuation and losses, UV light emitted from the transmission medium remains at power levels sufficient to substantially effectively kill pathogens in proximity to the output of the transmission medium, within a reasonable period of time. Different target pathogens require different power levels with bacteria requiring the least power for killing and cancer cells requiring the most power for killing. With efficiencies of collection and transmission, UV light sources with lesser power emission may also be effectively utilized.

Depending on the application and pathogen site accessibility, the transmission medium may be operationally positionable with or without a steerable carrier. For example, a carrying steering device, such as an endoscope or a hollow EBUS needle such as with video or other correlated mapped steering for viewable positioning, is used for positioning within human or animal organs whereas sterilization procedures may be effected with simple manual manipulation of the transmission medium without a separate carrier or positioning steering controls.

Disinfection:

Generally, an embodiment of the present invention comprises a method and device for the rapid disinfection of structural elements and devices from pathogens including interior and normally inaccessible areas, with no chemicals and attendant residues of any generated heat.

The method requires that the areas of the structural elements and the devices being disinfected are generally inert ("inert" being defined herein as operationally minimally or unaffected or not degradable by UV light) to UV light, with the method comprising the steps of:

a) Providing an elongated light transmission member, such as a fiber optics cable with a UV light input at a first end thereof and a UV light output at a second end thereof. The cross-sectional dimension of the elongated light transmission member is such that the light transmission member is capable (generally without necessity of a carrier or steering control) of being inserted into the area of the structural element or device, to an extent that light transmitted through the transmission member is able to effectively reach a major portion or all or substantially all of possibly pathogen containing sections of the area. The UV light output is of a wavelength and power intensity sufficient to disinfect the pathogen containing areas of the structural elements and devices at a desired distance and within a desired reasonable time period. (UV-C light output is more desired because of its greater speed and disinfecting effect on growths and pathogens, however, UVB and UV-A light of effective pathogen killing wavelength may be similarly utilized with compensation for the increased time and lesser efficiency of disinfection procedures). With insertion and close proximity of light output and infected area, power requirements are lessened as a result of the very short distances and the inverse square law as applied to the disinfecting output;

b) Inserting the light transmission member into or adjacent the possibly pathogen infected UV inert areas of the structural elements or devices whereby the light transmission member is capable of being proximately moved adjacent the UV inert areas within the desired distance; and c) Moving the light transmission member and UV inert areas relative to each other while disinfecting UV light is transmitted through the light transmission member whereby the UV light impinges on the UV inert area to be disinfected at a desired distance and for the desired time sufficient to acceptably disinfect the UV inert area.

A device suitable for effecting the disinfecting method comprises an optical fiber cable of a cross sectional dimension suitable for insertion within the area to be disinfected and with sufficient flexibility to conform to non-linear sections of the area and for relative disinfection movement of the method. A UV light source of sufficient power to effect the disinfection is provided at the light input first end of the optical fiber cable and optically attached thereto such as by common LED to fiber optic cable, butt coupling or optical lenses. The optical fiber cable is of sufficiently low UV attenuation (generally 3 db/meter or less) such that the power of the UV light emitted from the second end output is sufficient to kill pathogens to an extent considered to be appropriate disinfection in a desired reasonable time period. Details of suitable power, UV LED power output and attenuation and UV output sufficient to kill pathogens are readily apparent from prior art studies such as those appearing above. UV application time at a single site is ideally less than a second and may be several seconds or even minutes but should not exceed times needed for common but less reliable sterilization procedures.

In an embodiment, the normally opaque cladding (the term "cladding, as used herein includes both protective and optical layers on optical fibers such as buffers and light retention materials) of a fiber optic cable is rendered UV transmissive, such as by being removed or replaced with a transparent or light diffusion section, for at least a section length thereof, generally of the order of about 1 centimeter (as a non-limiting parameter). Disinfecting UV light is thereby radially transmitted to the proximal area of the structural element or instrument to be disinfected with the relative movement. In another embodiment or in a combined embodiment, the distal transmitting end transmits the disinfecting UV light in a trailing or forward directed cone which impinges on the peripheral area to be disinfected, during the relative movement.

The biopsy/suction or instrument channel in a typical endoscope is one of the most difficult portions of the endoscope to sterilize or disinfect because of its small diameter (generally with an ID of about 2.2 to 3.7 mm and a length of about 500 to 600 mm) and relative inaccessibility. The most common method of sterilization is with the use of sterilizing chemicals in a sterilization bath. This is however, fraught with problems since failure to completely remove the chemicals can result in toxic residues. In addition, it is difficult to ensure that the full reach of the chemicals or that the chemicals have had sufficient time or reach to completely effect disinfection. Other cleaning expedients such as the use of brushes are not satisfactory in terms of use and ability to ensure complete disinfection. Other small dimension diameter areas of an endoscope include water and air introduction channels of about 1 mm ID which present additional challenges to effective disinfection.

In accordance with an effective disinfection method, a low UV attenuation fiber optic cable of about 2 mm OD diameter (greater diameter cables are similarly utilizable with greater diameter channels), optically attached to an LED UV light source, is inserted into the biopsy/suction or instrument channel of an endoscope with standard diameters ranging from 2.2 to 3.7 mm. UV light transmitted through the fiber optic cable, once inserted in the channel, impinges on pathogen infected sites and kills pathogens within a determined time, dependent on UV wave-length, transmitted power, and distance from the transmission. Generally, because of the very close proximity between infected sites and applied UV light and dependent on output power, disinfection time may be under a second, several seconds or even minutes. Longer time protocols may be appropriate to ensure full disinfection. The impinging light is either forward of the distal fiber end or laterally or radially with extraction or insertion of the fiber cable out of or into the channel and with the end of the optical fiber cable having been rendered laterally UV transmissive or diffusive. Optical fiber cables may be provided with distal diffusors and the like (generally of about 10 mm in length). Similarly, properly dimensioned fiber optic cables can be inserted into other endoscope channels such as of water and air for the UV disinfection thereof.

Such UV treatment optical fiber can, either, as part of an endoscopic treatment through the biopsy channel, as described therein, or as a separate tool, be used to reliably, swiftly, completely and safely effect a full sterilization or disinfection of a biopsy or instrument channel of an endoscope, ideally at a rate equal to or less than the time needed for a normal extraction or insertion. If used as part of an endoscopic procedure, UV light is kept on during removal of the fiber optic cable from the biopsy channel to effect disinfection. Rate of removal of the fiber optic cable is at a rate enabling full peripheral impingement of the UV light on adjacent walls of the biopsy channel. The close distance between the fiber optic cable and the inner walls of the biopsy channel ensures the effectiveness of the UV disinfection literally within fractions of a second even with a small mW UV output from an optically connected UV LED. As a double check of disinfection of a biopsy channel prior to a procedure, the UV light can be turned on prior to and remain on during insertion of the fiber optic cable into the biopsy channel. Alternatively, the device is provided with a pressure contact switch (on a forward or distal end of the cable) which maintains UV light emission during the entire time the fiber optic cable is within the biopsy channel. Other controls include sensors which monitor the presence of the fiber optic cable in the biopsy channel for control of UV light output. Since there is no untoward effect resulting from continued UV application to the instrument there are no maximum times, except for convenience, for the continued UV application.

As a separate disinfection tool for normally inaccessible parts of medical instruments (with UV resistant inner walls of the inaccessible parts), the UV carrying fiber optic cable can be easily inserted into such inaccessible parts and the UV can be turned on either on insertion or removal. For best disinfection results the UV light is turned on for both insertion and removal. UV light on removal alone is more desirable than on insertion alone since it also effects sanitization of any pathogens initially carried in by the initial insertion of the fiber optic cable. For protection of workers carrying out such disinfections, open ends of the biopsy channel may be capped to prevent external UV light leakage.

The biopsy/suction channel is uniquely adapted to such disinfection since its interior surface requires chemical inertness and reduced friction. Accordingly, materials such as polytetrafluoroethylene (PTFE) or Teflon® are used to completely or substantially line the inner surface of the biopsy channel. Such materials are also inert to degradation by UV light and integrity of the endoscope is not compromised with use of UV light disinfection, as described. Other endoscope channels are also generally lined with inert materials such as Teflon® and can similarly be rapidly and easily disinfected.

Because the other accessible or exterior parts of an endoscope are susceptible to degradation with UV light a disinfection of the endoscope comprises disinfection with a chemical bath for disinfecting the easily accessible exterior parts of the endoscope and a separate disinfection of inaccessible portions of the endoscope and specifically the biopsy/suction channel, as described above, with highly disinfecting UV light.

Implanted medical devices such as pacemakers, medical infusion devices and the like, may be similarly disinfected in situ with the UV application light such as with optical cable ends being brought into position by simple skin incisions such as with a laparoscopic procedure and the disinfecting UV light being appropriately applied.

Devices such as borescopes, with fiber optic cables, are similarly used for inspection or other operations in structural elements such as metal, concrete, clay and other types of materials which are also resistant to UV damage. Accordingly, normally inaccessible mildew, mold, fungal and pathogenic growth can be eradicated with an inserted UV carrying fiber optic cable. Because of minimized size constraints and lack of UV/human contact issues, in these applications, the UV light source such as electrically powered UV LEDs (properly environmentally protected) can be directly inserted into the structural elements for disinfection either as a single LED or as a projecting array with the latter being more desirable in larger diameter areas and greater distance of UV emission light travel. In such applications the light is not actually transmitted but may be carried with the elongated member with transmission of powering electricity. A simple cable with UV LED structure can serve as an insertable household cleaning tool to remove the noxious growth from inaccessible areas such as ceiling or tile cracks not normally amenable to disinfectant preparations.

In a further embodiment, the UV transmitting fiber optic cable is provided with a distal focusing element such as a lens whereby emitted UV light is focused on a pathogen or growth such as mold to ensure that the pathogen or growth is completely eradicated with prevention of any return growth. In this embodiment with focused UV light, the UV transmitting fiber optic cable can be used for both inaccessible and accessible growths.

With the development of high power UV LEDs at 265 nm (peak disinfection) such as of 40 mW, 75 mW; 95 mW and 400 mw, it is possible to provide sterilization boxes with one or more of the high power LEDs for use directly during surgery with the capability of instant and full disinfection of surgical tools resistant to UV light, such as metal instruments, without the need for waiting the half hour necessary for autoclaving disinfection. The box is provided with a switch which is activated when closed and shuts off when opened, to protect against emitted UV light. Even the most resistant virus or bacteria is instantly eradicated with UV light at such levels and short distance application.

In Vivo Pathogenic Treatment:

Another disinfection embodiment for killing pathogens but within a host such as a human or animal comprises a method and device for the transmission of pathogen killing UV light from a UV light source outside the human or animal and through a UV resistant transmission medium. The transmission medium is operationally attached to a body insertion device such as an endoscope or insertion needle and guided or steered (if necessary) into and through the human and animal into very close proximate position relative to pathogens for the application of pathogen killing light thereto.

The device comprises a light source which emits UV light in the DNA/RNA disruption range and in most useful embodiments in the UV-C range between about 250 to 280 nm range with a peak at 265 nm. The light source, ideally, a single high powered UV-C LED, is optically connected to a UV resistant, low attenuation light transmission medium such as a fiber optic cable having a distal operational end with an OD suitable for insertion into a carrying instrument such as an endoscope and in further embodiments of being insertably positionable within ducts and passages of organs for positioning of a distal UV emission application end within, at most, several centimeters from pathogen infected sites. For example, with utilization of carrying bronchoscopes, the OD is generally from 2 to 3.7 mm and is less than 1 mm in embodiments used in reaching small, infected bronchia and bronchioles in a lung. Even with proximity rather than insertion such as in very narrow bronchioles, emitted light can enter these small areas for disinfection of pathogens contained therein. Colonoscopes, because of physiological dimension permit for larger diameters. Other types of endoscopes are accordingly sized according to utilization and accessibility parameters.

Specific parameters with a method and device in effectively and safely utilizing UV in vivo treatment of pathogenic cancer cells and tumors in all embodiments include the very proximate direct application of UV light to cancer cells and tumors with highly controlled, focused and diffused UV and particularly UV-C LED light of normally deleterious intensity but with controlled time and other parameters. As an adjunct, bacterial and viral pathogens can be similarly treated at a lower level of time, power and optionally with some deviation from optimal wave lengths.

It is understood that the reference to humans is for convenience and that corresponding devices and methods are similarly applicable to animals suffering from pathogen infection.

The light source device provides deep UV light in the DNA/RNA disruption range and particularly UV-C light generating elements, particularly UV emitting LEDs with effective power output. Other optional and desirable supplementing light generation elements such as white lights (for normal endoscope operation), indicator lights, ablating lights for removal of deactivated pathogens and the like may be optionally provided as well to provide aid in positioning and viewing of infected sites or as operational feedback for the normally invisible UV application (other types of haptic feedback may be similarly included). Ablation light such as UV-A may be included if needed or desired for removal of killed pathogens and the like. IR spectra light may also be included as providing Raman Spectra feedback related to pathogen presence and degree of removal.

Because of the possible toxic effects of the internally applied UV-C light (though minimal, as a result of minimal penetration), either or both the light source and endoscope are optionally provided with controls to limit the extent (i.e., applied power) of UV-C light application. These controls, for example, limit duration, intensity such as the number of activated LEDs, power applied to a single LED, general power application and the like with calculated application distances, specific wavelength of the applied UV-C light, focus, degree of pathogen infection (whether visible or just indicated and presumed presence), and the like.

Existing commonly obtainable UV generating LEDs operating in the wave lengths having the greatest RNA/DNA disrupting capability (265 nm) have essentially had power output (20 mW or less, with difficult to obtain LEDs being on the order of about 40 mW) rendering them inadequate for other than directly combating pathogens such as viruses, fungi, or bacteria on surfaces or open wounds. Transmission of UV light through transmission media such as optical fibers is believed to totally or almost totally reduce output power to negligible and ineffective pathogenic fighting levels.

Ostensibly, high powered mercury arc and xenon bulb UV generating light have been used for direct application UV disinfection purposes. However, such sources emit a broad spectrum of wavelengths requiring constant pulsing and specific wavelengths (as filtered) and have even lower specific power than single wavelength LEDs. The aforementioned Mankin patent application discloses a direct available power output of 1.2 mW. This generally renders them unsuitable, in unmodified form, for transmitted in vivo use in deactivating pathogens with losses of more than 95% or even complete loss.

LEDs which emit UV in the UV-A and UV-B wavelength ranges have been utilized (e.g., as in the aforementioned patent application by Cedar Sinai Hospital) but at the cost of vastly reduced efficiency in disrupting the RNA/DNA of pathogens and vastly increased treatment times. As a complicating factor, UV-C, because of its effectiveness against pathogens with sufficient power, is believed to be fraught with possible dangers of the UV-C engendering adverse and/or toxic effect with respect to healthy tissue, cells and blood vessels. Control of UV-C light is therefore believed to be important.

UV LEDs developed for applicants, with increasing power levels embody the requisite characteristics of DNA/RNA disrupting capability at most efficient wavelength levels (generally between 260 to 270 nm with a peak at 265 nm which is the center of the RNA/DNA sweet spot for disruption) coupled with power intensities on the order of at least 40 milliwatts per LED for enhanced disruption. Other, effective long-lasting UV-C LEDs, with emission power of about 75 mW, 90 mW and 360 mW have also been specifically developed for the purposes of this application and are generally available from applicants. These LEDs in the 265 nm range have been developed for this invention with high stability, despite enhanced thermal problems, with judicious combinations of housing and die expanded sizes (with improved heat sinking) and thermally resistant materials and glues used in the construction of the higher powered 265 nm UV-C LEDs.

Treatment of blood for pathogen removal, normally currently effected by ex vivo removal and treatment of the blood and return may be effected by simple placement of a section of the distal end of the optical fiber into a blood vessel and emission of the pathogen killing UV into the circulating blood stream without necessity for blood removal.

UV Light Source:

The UV LEDs are described and utilized in the invention of the present application, and it is their available characteristics of specifically defined UV emission wavelength and controllability which are desirable. Other newer alternative UV light sources (such as LED based lasers or coherent light emitting LEDs) are being developed which may replace LEDs as UV light sources, in accordance with the invention and are included herein.

A next generation UV light generating device was thought to be OLEDs (Organic Light Emitting Diodes) but the original UV LEDs kept up and still lead in current applicability. New generation UV light sources may be described as "solid state light emitting devices", which include but are not limited to LEDs, OLEDs, pLEDs (Polymer Light Emitting Diodes), and the latest ones, Quantum dots. Quantum Dots actually give off UV-B light and could presumably easily soon evolve to include high power UV-C (265 nm). As with diodes, use of component materials other than silicon results in widely differing properties, some of which probably will be smaller wavelengths. (Including Lasers)

Future devices may not be diodes, but rather conduct more evenly in both directions. "solid state light emitting devices" would cover them all but may not include forms of vacuum tubes, particle accelerators, or radioactive isotopes.

Though single LEDs with acceptable power outputs are most desirable for simplicity and control, as well being most amenable to UV light collection, LED arrays with optical transmission combination are also possible to enhance power output and possibly provide other desirable characteristics as will be defined herein. Light collection and transmission as well as focusing from a light array may however be problematic and difficult to control for effective output.

Spreading UV-C light internally will not cause cancers but will de-activate quickly growing cancer with DNA-exposed tumor DNA in mitosis. The conclusion is that internal UV-C should be as high powered as possible, with the desirability of increasing power increasing cancer cell penetration, without scalding of normal tissue like X-rays may cause. In addition, the ability of healthy cells to repair the low to moderate DNA damage they may receive from UV-C light may be quite strong, especially when compared to the negligible repair capability of cancer cells.

The LEDs in an array embodiment may also include UV-A, and UV-B LEDs, though fewer in number because these LEDs may actually have higher power and are primarily utilized for ablation purposes. Each LED type array may have its own In/Out switch and pulse generator and timer set (like UV-C) with their integrated Duty Cycle and Exposure Time controls. A microcontroller version doesn't need to (but can) have the physical switches to enable combinations of UV A, B, and or C. Red light emitting LEDs or any other color or shade are optionally included in any LED array and are operatively linked to the UV-C light generation as a clear real time visual indicator of UV-C light generation.

Relatively safe but with greater penetration ability UV-A light, which normally would not be effective even for moderate exposure, may be rendered effective by very close proximity to the UV light source, for only several seconds. Endoscopes of similar nature may be utilized in the same modified form in treatment of different organs or body sites attacked by bacterial, cancerous, or viral pathogens. UV-C emitting LED diode devices with highly focusable coherent light output, similar to laser light, with higher output power levels are currently being developed by applicants.

Operation Feedback:

In further embodiments, the endoscopes or, for example, bronchoscopes may be provided with light detectors which detect specifically fluoresced pathogens, for more efficient direction of the UV light. Fluorescing of cancer cells is often utilized with similar applicability to other pathogens. In addition, in other embodiments, the endoscopes or bronchoscopes are provided with DNA debris detectors, in order to ascertain degree and extent of UV treatment on disruption of pathogen. When living entities are growing and replicating their DNA, their DNA is more exposed and is especially vulnerable to external radiation. Thus, it is quite possible that this selective effect, that is, the faster detrimental effect on the multiplying viral DNA within a virally infected cell compared to a lung cell, could be used to increase the differential effect of close UV destruction of viruses and viral cells over non virally overtaken ones.

White light illumination from regular LEDs and red or other color light aiming light from colored LEDs may be combined or bundled with the UV-C light in the single beam. Criteria for the effectiveness of the UV-C light include sufficient power and optimized wave length and for safety, control of the power with any or all of timed release or bursts and control of the number of activated LED and their power emissions. LEDs or various power and wave lengths may be combined and appropriately controlled as needed for effectiveness while minimizing peripheral damage to healthy tissue.

IR or Raman spectroscopy (with IR radiation being applied with a portion of the inserted fibers) may be utilized to identify signature peak position of existing viruses with peak height being indicative of extent of infection.

Treatment with UV Light Collection and Transmission:

Regarding UV delivery in vivo, this is primarily a therapy, not a cure, one that works together with others or initially on its own, prior to blitzing the human tissue with unforgivably blunt and more powerful X rays. Hundreds of billions of dollars have been expended in cancer research, therapies and treatments. The present treatment device and protocol can essentially destroy localized tissue infected with bacteria and viruses (i.e., by disrupting RNA structure to eliminate replication of virus or bacterial pathogens on tissues), as well as selectively killing cancer and tumor cells (also DNA disruption) with minimal effect on adjacent healthy cell tissue.

An effective transmission medium for therapeutic UV light introduction into a body and particularly as carried by existing endoscope generally requires the following criteria for optimal performance:
 a) A UV light source having a UV light output in the DNA/RNA disrupting wave length and most desirably at or near the 265 nm wavelength have greatest DNA/RNA disruption effect.
 b) To compensate for inevitable power losses inherent with UV light transmittal emissions from the UV light source, power output is desirably greater than 20 mW and ideally at or above 75 mW with the greater the output the more flexibility is inherent in the system.
 c) An optical interface between the UV light source and the transmission medium should be as complete as possible with the transmission medium end such as an optical cable end being able to completely cover the light emitting source such as a die of an LED for a physical butt connection (with proper alignment such as with an x-y plane alignment device) or with an intervening light directing interface which collects light from the light source, collimates it and focuses it into the transmission medium proximal end.
 d) The emitted UV light should be maximally collectable with minimized scatter and with maximum transmission by a transmission medium. For a UV compatible optical fiber transmission cable this is a transmission into an end of the fiber optic cable of less than about the uptake acceptance angle of about 20 to 27 degrees (light above the acceptance angle is absorbed and turned into heat).
 e) Transmission media are required which are resistant to the effects of UV light, which are flexible, as required, and are of dimensions to collect light and to transmit light with appropriate cladding, diffusers, a dimensional parameters for collecting light and fitting into operational area and channels. Fibers with flexibility, particularly if of low UV attenuation composition, are of very small diameter generally of less than 600 micron diameter whereas if the fiber is to efficiently accept LED should be of larger diameter of generally several millimeters or of bundles of fibers with large interstitial spacing with loss of light intake. Fused end fibers provide good intake with minimized interstitial losses and are still flexible with distal operation part of the fiber being of separated fiber bundles and requisite flexibility.
 f) Light collection is optimal with large diameter transmission media capable of greater light acceptance whereas light output transmission media require minimal diameter for flexibility capability (generally on the order of a 1 cm bending radius for bronchoscope applications) and small diameters (1 mm or less) to enable the transmission media or such as fiber optics to be insertable in small diameter channels in a bronchoscope or an EBUS or EUS aspiration needle and for entry into small organ areas such as bronchia of a lung. Optical transmission down-focusing media such as lenses or tapered fiber sections are utilizable but with major losses in UV transmission and power.
 g) After all losses of power from the UV light sources are factored including attenuation losses of the transmission media, failure to completely capture light or properly transmit it and transition losses, output light power should be at least 2 mW/cm$^2$ and more preferably at least 20 mW/cm$^2$ should be emitted from the distal end of the transmission medium onto the pathogen for effective and reasonably timed pathogen eradication. Power losses of greater than 95% are not unexpected.

The following is illustrative of structures and methods of effective UV light transmission which ameliorate light transmission power levels to effective values.

Use of DNA/RNA disrupting UV light is similar to and possibly even better than the also non-systemic therapeutic assist to a struggling body of localized traditional X-ray radiation therapy. Another embodiment comprises an efficient light transmitting device and method of light transmission for purposes of focused light applications and for practical UV disinfection in difficult to reach areas such as within a body or within narrow channels such as in endoscopes.

An embodiment of the method comprises the steps of:
 a. emitting light from a widely scattering non-coherent light source such as an LED;
 b. collimating the emitted light to a diameter effective to capture and collimate substantially all of the non-coherent light emitted by the light source;
 c. introducing the substantially all of the collimated light into a low attenuation light transmitting medium of a diameter at least substantially equal to that of the collimated light (it is understood that the collimation need not be complete but may be sufficient to introduce light at less than an angular uptake angle);

d. focusing the collimated light to a focal point into a smaller diameter transmitting medium of desired size; and e. emitting light from the smaller diameter transmitting medium with enhanced power and intensity.

Alternatively, steps b), c) and d) may be combined with a single or combined element which effects both collimation and focusing together with the use of the transmitting medium of substantially equal diameter.

In a specific embodiment, a device for effecting the method comprises a light source such as an LED, which is surrounded by a reflective collimating member such as a cone or parabola (symmetric or asymmetric or off axis) with a base section permitting entry of the light source allowing collimating reflection of substantially all (or at least a major portion) of the light emitted from the light source. The device further comprises a short transitional light collection and transmission element with a relatively high angle of light acceptance and a diameter matched to the open end of the collimating member for maximum collection of collimated light. The short transitional light collection and transmission element is in turn coupled to a short first fiber optic cable of similar diameter with a low attenuating coupler and with maximum light transfer to the fiber optic cable. The similar diameter first fiber optic cable is then coupled to a longer second fiber optic cable of reduced diameter with a low attenuation focusing input lens, with the second fiber optic cable being utilized for distal end output of the light with insertion of the longer second fiber optic cable into difficult to reach areas requiring the light output.

Components utilizable with the output of a deep UV emitting LED, include the light collection and transmission element which is either an available light pipe or a liquid light guide and which have more than double the UV light acceptance angle, as compared to available low attenuation UV fiber optic cables. The light pipe and liquid light guide are on a par with UV degradable plastic fiber optic cable with respect to uptake angle, but without degradation. Further reduction of UV light loss is obtainable with removal of attenuating air (specifically the nitrogen component of the air) from the reflective collimating member such as by drawing a vacuum or partial vacuum therein or by integrating the reflective collimating member with the short liquid light guide and filling it with the same liquid.

Another embodiment of a method of maximizing distal deep UV light output in a UV light transmission system comprises the steps of:

1. Collimating all of the UV light output by integrating the UV light source with a collimating member having an output diameter greater than that of the UV light source and at least that of the collimated light;

2. Collecting substantially all of the collimated UV light with a light collector and transmitter element having a low UV light attenuation transmission with the light collector and transmitter having a diameter optically matched to the output diameter of the collimating member; and 3. Transmitting and focusing the collected collimated light to a UV light transmission cable with a distal end output.

Modifications of the above described structure, include coupling the short light pipe or liquid light guide directly to the long fiber optic cable via a lens focusing coupler, utilization of light pipes or liquid light guides of varying diameters with appropriate collimating or focusing lens couplers.

LEDs, having a unique 120° or more hemispherical emission are difficult to focus using normal optics. A parabolic mirror reflector is a good match to the LED since it collimates (reflects to parallel rays) such widely diverging light. Such larger collimated beams are traditionally then focused to a point or smaller region, usually by lenses. However, in accordance with the invention, a transitional element may be used to enhance collection of light normally lost by limited light uptake (particularly UV light). The transitional element comprises Liquid Light Guides which are filled with a higher index of refraction substance. They have a larger numeric aperture as well as being able to be made with larger core diameters and thus are a good match for coupling. Moving light exiting the transitional liquid light guide to small or difficult places to access is effected by a coupling of a section of similar sized fiber optic cable via the known methods of coupling two fiber cables and matching numeric apertures. For interconnection to smaller diameters of fiber optic cable, again a fiber to fiber coupler may be used. The above processes are more critical for smaller wavelengths than longer ones. Thus, for ultraviolet use, especially the smaller UV-C wavelengths, this sequence of components can be especially helpful, enabling much larger overall transmission efficiencies than possible without using these initial optical mirrors and light guides. Liquid light guides, as opposed to light fibers, however present difficulties with flexibility and are generally more effective with endoscopic or other applications which require little or no flexibility.

To further aid in light collection, in an embodiment, a UV light emitting diode is provided with an integrated lens which, though entailing some losses, reduces the normal 120° emission output angle to more closely match the uptake angle of the connected fiber such as 27° to thereby increase the amount of light which is directed into the fiber for transmission. It is understood that this and any other lens used in the coupling or UV light transmission must be resistant to UV degradation. Generally, quartz is an ideal resistant material though it is more difficult to handle and produce and more expensive than plastic lenses.

In another embodiment, the collimation into a liquid light guide is replaced with a lens system such as a TIR (total illumination retention) lens which is configured to both collimate light collected from a light source such as an LED and to thereafter focus the collimated light to a focal area or plane equal to or less than that of an optical fiber diameter.

Aspherical lenses, particularly when used in pairs, provide a similar collimating function with focusing into narrow diameter fibers.

Emitted light from a light source fitted into a base indentation of the lens is collimated by a parabolic section of the lens and the collimated light is then immediately focused by a concave section of the lens into a first fiber bundle at the focal area or plane, shown as being 11 mm from the distal end of the lens. The diameter of the first fiber bundle is, for example, 8 to 12 mm and this fiber bundle is an intermediate to transmission to a second smaller fiber bundle (1 to 2 mm) via a second reduction focusing element between the first and second fiber bundles. It is desirable, to avoid light loss to configure the TIR lens to focus the collimated light to fit within the diameter of the smaller fiber bundle.

A typical example of a utilizable TIR lens has a diameter of about 20 mm with an inserted 3.9×3.9 LED having a light emitting die of about 1.2×1.2 mm and wherein the focusing distance is about 16 mm.

An aluminum ferrule end of a fiber optic cable holds the fiber optic cable into position relative to a TIR lens focusing light into the 2 mm fiber cable end positioned at the focal point of the lens. The fiber optic cable may be readily removed and replaced, by releasing the ferrule clamp, as needed, for sanitization purposes or wear.

In order to reduce the total distance to the focal point, which for UV light is a light loss factor, another embodiment has a separate parabolic collimating element linked to a focusing convex lens, such as a Fresnel type lens having a collapsed and significantly smaller thickness, but similar focal length.

Matching different Numeric Apertures with a spherical lens provides for better coupling. One of the ways to match optical components with differing sizes of entry and exit light cones is to use a spherical (ball) lens. An example is a coupling into a lower entry angle fiber optic cable of light from a larger angle emitter such as an LED. A side-emitting LED has smaller emission angles than top emitting LEDs but still larger than the fiber optic cable.

In further embodiments, the focusing distance volume is enclosed and the air containing volume (including the parabolic collimator) is either provided with a partial vacuum or an inert gas. With the former, the parabolic structure is re-enforced against air pressure collapse.

It is noted that commercially available TIR and Fresnel lenses are comprised of plastics such as polycarbonates which are susceptible to UV light degradation. Accordingly, for use in collimating and focusing, the lenses are comprised of UV inert materials such as quartz with the same or similarly effective configurations and structures. Degradable lenses, however, are utilizable with disposable elements and may be used for a number of times before unacceptable performance ensues due to degradation. Other lenses include aspherical lenses for selective focusing, as required.

The present application entails a similar utilization as in current radiation treatments, except that relatively weaker, UV-C light is used instead of X-rays, and it is delivered directly inside a person's body, very close (generally not more than 25 mm) to the regions needed as opposed to normally external radiation treatment. X-rays used in radiation treatment are essentially a similar type of light, or more correctly electromagnetic radiation, but at a much higher frequency and therefore energy level. The peak of RNA/DNA sensitivity, common to bacteria, viruses, and tumors, is 254 nm-275 nm, i.e. that of UV-C light with a maximum peak at about 265 nm.

Borescopes used for transmitting UV light are entirely configured for the transmission of UV light in the visible wavelength spectrum such as in the range of 365 nm which has little if any effect on pathogens or their disruption. The borescope UV transmission is for mechanical effects such as detection of metal fatigue or defects, curing of glues, etc. These devices and utilizations, with UV light outside of the pathogen affecting wavelengths, are accordingly outside the scope of the present application.

Safety Issues:

As described above, recent actual developments in UV pathogen treatment (almost exclusively that of viral and bacterial treatment requiring less aggressive treatment than cancer) have exclusively focused on UV-A light because of safety issues despite lowered effectiveness and the requirement of much longer exposure.

Even with lower power relative to X-rays, UV-C light may be too powerful and possibly harmful to healthy tissue, or blood vessels, though this has not been clinically proven or even explored to any valid extent. To avoid even such unproven harmful extent, precisely focused or with wider focus and controlled emission with controllable UV emitting LEDs with precise wavelength, pulsing circuit and precise short duration exposures, are provided and adjusted so that proper exposure is generally only a few seconds and at most, several minutes. Precise emission distances are generally obtained with physiological factors and experience medical personnel or even with assistance with LIDAR or similar type circuit distance feedback.

Stretching out an exposure with pauses in between stronger UV pulses has equivalent total energy. It is believed that this strongly decreases harm to normal cells generally attributable to normal cells having better working DNA repair mechanisms, which can correct DNA damage, if given sufficient time, as compared to pathogen-infected cells.

Operation parameters of the light source with respect to pathogen deactivation levels and levels at which healthy cells and tissue become adversely affected are measured with UV-C light power levels actually reaching the pathogen or healthy cells or tissue. These are conventionally measured on the basis of area being affected and are in units of milliJoules/square centimeter ($mJ/cm^2$ and dimensional variations thereof). Baseline measurements are calibrated to a UV-C application of 265 nm (the ideal wave-length for RNA/DNA disruption) with variables being generated power levels, application time and generation distance from the application site with variations in focusing. Operational tables with the variables and deactivation effects determine appropriate, effective and safe UV-C light application. Deactivation of pathogens such as viruses and bacteria, takes on the order of seconds or at most minutes with direct UV-C light application to the pathogen at milliwatt power levels.

Tuberculosis, pneumonia and bronchitis are all pathogens (bacteria and virus) entering the body via the respiratory system and eventually entering the lungs. They are accordingly surface initiated pathogens which burrow down into the lung tissue. There are no penetration issues with respect to UV-C light application for these surface-initiated pathogens. A full bronchoscopy lasts about 30 to 60 minutes to view the various bronchi and air passages with about 20 main sites for a typical lung. Accordingly, a full lung treatment takes just a little bit longer, Since the above pathogens are more susceptible to being disrupted than human tissue, determining the differential between the respective disruptions, as defined above, provides a basis for selecting a targeting power level to be used.

Effects of UV light and particularly UV-C have been studied with numerous base line pathogen disruptions having been determined in terms of power levels at disruptive wave lengths (with an ideal 26 nm wavelength) generally of $mJ/cm^2$. These have been exemplified in the tables reproduced above for the specified pathogens.

An issue with respect to detecting pathogens (i.e., viruses and bacteria) is that the only real basis for locating bacteria and virus sites is the location of visible physical damage effected by the pathogen.

Accordingly, an endoscope such as a bronchoscope is used to target damaged sites with UV-C light, with higher values of the determined differential and with more focused UV-C light since the virus or bacteria is certainly present and has taken over cells. The entire remaining lung may be blanketed with lower power of UV-C light as a prophylactic against possible virus or bacteria presence. In this latter respect it may be useful to utilize a wider focal spread. Depending on the minimum time per site, as determined, normal bronchoscopy procedure time should be appropriately adjusted.

As known, distance has a strong effect on effective intensity and energy delivery, with an inverse squared relationship. Accordingly, a specific distance is included in the definition for settings of various distances. The peak DNA sensitivity curve is wide enough to safely use a wavelength range of 10 nm, since known LED UV-C devices have 90% of their power within the 265 nm+/−5 nm. Thus, the utilizable power is a UV-C device with 90% of its emitted power being in the 265 nm ideal range.

In addition to classical bronchoscopes, the UV light described herein is utilizable with all types of endoscopes, such as used specifically with different organs whether inserted into body orifices or into small incisions. These include endoscopy, used for investigating many systems within the human body such as:

Gastrointestinal tract: esophagus, stomach, and duodenum (esophagogastroduodenoscopy), small intestine (enteroscopy), large intestine/colon (colonoscopy, sigmoidoscopy), bile duct, rectum (rectoscopy), and anus (anoscopy).

Respiratory tract: Nose (rhinoscopy), lower respiratory tract (bronchoscopy).

Ear: Otoscopy

Urinary tract: Cystoscopy

Female reproductive tract (gynoscopy): Cervix (colposcopy), uterus (hysteroscopy), fallopian tubes (falloposcopy).

Through a small incision: Abdominal or pelvic cavity (laparoscopy), interior of a joint (arthroscopy), organs of the chest (thoracoscopy and mediastinoscopy).

Capsule endoscopes, having no physical connection to outside controls, but are instead controlled (internal body movement and operation) or charged with magnetism, RF, Bluetooth and the like, as well as disposable endoscopes are also included herein. It is understood that while organ treatment is a primary consideration, other body parts such as blood and bones of the skeletal structure are also amenable to similar treatment of leukemia or other pathogenic based blood or skeletal afflictions.

As used in this application "endoscope" includes any structure which is insertable into a human or animal body and which is capable of carrying and transmitting UV light into the human or animal body either through its own light transmission elements or via a carried light transmission element. The endoscope, as classically defined, is further expanded as not requiring viewing capability but only that it be used in conjunction with a positioning directing means such as a computer linked X-ray guidance map or even with experienced manual handling.

The UV light source, as described herein, is positioned outside of the human or animal body and only the UV light emitted therefrom is transmitted into the body. In classic endoscope devices, an external light box contains visible light emitting elements which are transmitted through the endoscope for illumination and viewing of internal body parts such as organs. Bronchoscope endoscopes, for example, are used for visible examination of lung sites for detection of anomalies as previously referred to. In disposable endoscopes such as those sold under the trademark GlideScope, the light source or "box" is in the grip control of the endoscope.

Battery packs, especially if in cartridge form and swappable may be used to make endoscopes completely portable with configurations such as with the aforementioned disposable endoscopes.

There already is an illumination cancer therapy using electromagnetic radiation at far higher frequencies (smaller wavelengths) than UV-C and even Far UV. X-rays used in radiation therapy, are usually delivered from outside and have a wavelength of 0.01-10 nm. X-rays. These are of high-frequency, and thus high-energy, electromagnetic radiation. They have wavelengths ranging from 0.01 to 10 nanometers, and thus frequencies from $3\times10^{19}$ to $3\times10^{16}$ Hz. Higher frequency is more energy (Planck's law). If UV-C degrades RNA and DNA links, X-rays obliterate them! It is tolerated for Brachytherapy for radiation treatment because the alternative is more lethal. Use of precisely delivered UV-C is much less deadly than X-rays, and it is delivered much more locally, internally, and with more precision and guidance.

There are several characteristics of cancer cells which can be utilized in more efficiently "zapping". Cancer cells are easily tagged such as with fluorescing dyes which make them very easy to separately identify from healthy normal cells. With such visible tagging, a UV-C device may be programmed to detect the cancer cells and with AI evaluations determine when to trigger UV light treatment at an optimal focused distance with an optimal pulsed or timed UV intensity while avoiding UV impingement on adjacent health normal cells. As a result of such fine-tuned treatment, stage 4 cancer patients, with metastasized cancer sites, are more effectively treatable. Normally therapies, with broad application, as required to treat metastasized cancer tend to also affect normal cells to a great extent with concomitant lethal effect. Highly focused UV may obviate this lethal effect by minimizing the extent of normal healthy cells being treated together with the cancer cells.

A factor in determining requisite UV light intensity is the determining of effects of the light penetrating thick layers of tissue and if the cancer cells are blocking deeper pockets of more cancer cells. Specifically, with high power, LED with wavelengths all in the DNA/RNA peak sensitivity zone, it is possible to obtain maximum effectiveness and shortest exposure times.

There is a clear differential between normal cells and viruses and bacteria. This differential can readily be exploited for safe UV treatment. With respect to cancer cells versus healthy cells a differential is established with respect to UV effect on cancer cells relative to healthy cells.

DNA of rapidly dividing (duplicating, as in mitosis) cells involves frequent and prolonged unraveling of their DNA so that they can be duplicated, translated and used to manufacture proteins with which to make another cell. Harmfully cancerous cells are by definition growing much faster than the body can handle and much faster than normal cells. Normal cell DNA is much better protected from DNA smashing UV-C photons than the DNA of quickly growing, neoplastic tumor cells frequently and regularly exposing themselves to radiation.

A second relative weakness of cancerous cells is that they do not have a functioning DNA error repair system the way healthy normal cells do. Normal cells have enzymes that correct single letter errors and open links. This synergizes with the first mechanism. Not only are cancerous cells more vulnerable to radiation-based DNA destruction, such destruction doesn't get quickly repaired as with normal cells.

A third and other differences between normal and tumorous cells is that such rapid growth of cancer cells needs more and rapidly available energy. Cancers have modified the ATP→ADP cycle (which release usable energy). The modifications those cells make and their ability to operate in low oxygen environments (hypoxia). Prior art literature provides evidence that such hypoxia can render tumor cells "resistant to radiation and chemotherapy". If so, it is further synergistic with UV-C radiation therapy wherein the treatment protocol for viruses results in significant RNA debris which the body interprets as foreign bodies. This results in antibody generation but without a remaining pathogen. This could result in a powerful mechanism for prevention of pathogen re-infection. This is similar to vaccine protocols using weakened viruses.

When it is desired to have extended externally transmitted UV radiation for cancer therapy, such as at night for even hours, perhaps with regular periodic exposure pauses as described, an endoscope, or a dedicated small UV-C source with adjusted duty cycle and exposure time, is connected to the outside of the remaining optical "window to the organs". After a cancerous tumor is removed such as by being dissolved, a surgeon removes the connector and fiber optic segment and reseals the skin. This may be suitable for deep brain UV delivery since there is no copper or other contaminating substances left internally other than glass (silica) transmission members. Stage 4 cancer situation would be an appropriate condition where multiple spots each need several hours of non-harmful to normal tissue radiation, preferably delivered simultaneously and quickly.

The activation or creation of anti-bodies may be a "side-effect" of UV RNA/DNA disruption treatment. A "fluorescing" method for virus or anti-body cells or organ area tissue helps showcase the affected area.

In accordance with an embodiment of the invention, a method for the treatment of a human or animal against viral and/or bacterial pathogens comprises the steps of:
1) Inserting an endoscope with fiber optic light transmission contained therein into a human organ or body part infected with a pathogen,
2) Guiding the endoscope into close proximity to the pathogen,
3) Directing UV light of sufficient intensity and of sufficient duration through the fiber optic light transmission to impinge on the pathogen for the destructive disruption of the replicating DNA thereof, with minimal adverse effect on tissue of the human or animal organ or body part, and
4) Providing sufficient destructive disruption to effectively treat the human or animal.

A system is described whereby the exposure time necessary to wipe out a particularly identified pathogen is determined and then used to effectively control appropriate UV delivery. For example, for the same power level and spectrum of light, if for Corona-virus in the throat and upper trachea would need 35 seconds of treatment time, the flu would need 15 seconds and bacterial infections would need 5 seconds. It is possible to bring UV-C light in direct proximity to a pathogen such as a cold virus for minimal amounts of time with an insertion tube akin to a penlight or otoscope in structure. A penlight or otoscope is a useful implementation example because it has no external wires minimizing power delivery leakage. The use of higher power for shorter exposures is facilitated operationally by the use of high power output UV-C LEDs. Safe wireless, and convenient sourcing of electrical power for them is fortunately also facilitated, by utilizing today's rechargeable battery packs and their high power density technologies. The mouth is another accessible place for insertion and treatment of pathogens such as strep throat and since a common cold is viral, treatment may be effective in ameliorating or even curing the common cold. Even dental treatment can be facilitated since cavities result from bacteria which are readily eliminated by UV light.

If distance measurements are required such as in non visible areas, a distance measuring device such as LIDAR may be included in the fiber bundle with one fiber providing the laser signal and another receiving it to activate echo distance measurements. Ultimately, securing data without relying on distance, may be even better. Bathing the area with UV regardless of distance and killing the virus and not the healthy tissue obviates distance issues. When targeting bacteria or virus the penetration from a distance is miniscule and will hardly affect deeper tissue. Even if it kills a thin layer of it probably will just die off and be replaced. For tumors, in order to get penetration, high power is needed right up against the tumor so again distance will not be an issue. The issue of distance will come into play when trying to achieve penetration with a tumor and inability to get the endoscope right up against it.

A pushbutton/foot switch trigger may be used to precisely emit a calibrated duration (exposure) of light pulse in ways that do not compromise the endoscope user's use of his hands. These controls may be Bluetooth or other wireless link mechanism for convenience.

An optional preliminary step is that of pre-determining pathogen location such as with x-rays, fluorescing or other known location procedures. An optional final step is that of detection of DNA debris to ascertain effectiveness of the UV light treatment and direction of further steps, if necessary.

Fiber optic cables such as available from the Molex Corporation have minimal attenuation even in the deep UV range of 265 nm. In an embodiment of the invention, such low attenuation fiber optic cables are used in place of existing endoscope fiber optics (with a standard endoscope retrofit) in order to bring UV-C light from a UV-C light source, such as the LED arrays described in the co-pending applications, into organs such as the lung, to quickly kill pathogens such as viruses and bacteria within a time frame before the UV-C light adversely affects healthy cells and tissues. The low attenuation fiber optic cables permit the utilization of smaller LED arrays or other sources of UV-C light with lower power in an equivalent manner since attenuation power transmission losses are minimized. Testing has in fact shown that optical fibers commonly used in endoscopes are not amenable to any deep UV transmission.

Prior art has shown, as alluded to above, that a UV-C module took out a tissue culture of Covid-19 in 30 seconds to a 99.9% kill rate with a direct application of light with a UV wavelength of 275 nm. The 30 sec of the 18 mw used is about 600 mJ of energy.

Swapping the special low attenuation fiber optics cables for the original fiber optics in an endoscope necessitates specialized handling and reconditioning of existing endoscopes. Accordingly, in another embodiment the need for modifying existing endoscopes is obviated.

In this embodiment, the device comprises a separate low UV-C attenuation fiber optic cable which is adapted for insertion into an endoscope insertion tube (commonly used for insertion of a biopsy tool) or biopsy/suction channel with a length adapted to the specific type of endoscope. The fiber optic cable is further configured with a UV-C light transmissive end and with the other end coupled with a low attenuation coupling of a collimated or focusing lens or optically bundled UV-C output from an array of UV-C emitting sources such as LEDs or lasers (collectively referred to herein as LEDs) such as directly or with "pig tail" connectors commonly used with white light LEDs. In such embodiment, particularly with a coupled single high powered LED, the LED-fiber coupling may be contained in a manipulation handle for the fiber.

Alternatively, a focusing lens enables the output from a larger diameter fiber optic cable, a laser beam, LEDs, or other collimated light to be completely focused into a smaller fiber optic cable at a focal point area without major loss of light or power.

Though existing 40 mW UV-C LEDs provide a nominally sufficient power for in vivo pathogen treatment higher power LEDs of 75 mW, 95 mW and 360 mW have been developed for this invention. The problem of existing low power UV-C light sources and high attenuation of UV-C, for effective pathogen killing transmission into a human body has been ameliorated with the specific development of high power UV-C LEDs.

Alternatively, extensive arrays (7-50) of 265 nm LEDs which are powered with high input power (with various provisions for heat sinking) provide total output, even with attenuation, sufficient for therapeutic treatment of pathogens within several seconds or even in less than a second per treatment site. LED arrays such as used with white LEDs and even in some UV applications are generally simple spaced placement of LEDs with individual outputs within a source without any concentrated power above individual LED power outputs. These are totally unsuitable for effective transmitted UV-C light. The LED arrays of the co-pending applications and the present application are arranged to have combined transmittable outputs to provide multiple power outputs in an enhanced pathogen death ray. In addition, the combination provides a minimal dimension focused output for full introduction into small diameter fiber optics which are smaller than the dimensions of a single LED.

The output power of the array, as described in the co-pending applications is, in an embodiment herein, in the 265 nm range (260-270 nm) sufficient to kill pathogens within several seconds and ideally within a second, at an emission distance within about 50 mm. The fiber optic cable in the second embodiment may be of a single unitary length or of optically coupled sections. In the first embodiment, the endoscope fiber optic cable is optically coupled to a connector fiber optic cable extending from the light source. In the second embodiment a long fiber optic cable may include the connector section and the insertion section or may be constructed of coupled sections.

At the UV-C light source, output from the individual LEDs is collimated with a collimating lens to focus on the coupled end of fiber optic cable with no or minimal loss of UV-C light. Alternatively, each of the LEDs is directly coupled with a short (e.g., about seven inches) low attenuation fiber optic cable such as by an LED coupling pig tail connector or with the short fiber optic cable directly abutted to the LED die which emits the light. In this latter embodiment the fibers extend into a pierced protective cover of the LED with an anchored abutted connection. The other ends of the LED connected fibers are gathered in a single cord for direct optical connection (with focusing lens or direct abutment) to the long fiber optic cable which may either be the swapped endoscope cable or the endoscope insertion cable.

In another embodiment, the end of an optical fiber cable is directly "butt coupled" with the light source or with a lens on top of the light source. This is the most direct form of connection but the most difficult to effect correctly. As far as is known, this type of optical connection has not been used with a deep UV light source and has generally been utilized only with visible light sources.

Though butt coupling is not susceptible to losses engendered by transmission through solids such as lenses, various criteria must be followed to maximize UV light collection and transmission. If the fiber is not dimensionally capable of fully covering the light source such as the die of an LED, significant light is lost from the non-optically covered areas. Increasing the diameter of the optical fiber, while effective in increasing UV light uptake, presents problems in carrying light to smaller operational fiber diameters of the cable. Focusing lenses and tapered fiber sections result is major losses of transmitted light and power. Increasing power of the UV light source generally requires increase of dimensions of the light source and concomitant increase of fiber cable diameter and increased losses resulting from down focusing to operational fiber diameters.

Alignment issues arise in situations where a fiber is of insufficient dimension to fully cover the UV light source with small deviations in alignment resulting in major, if not complete loss of transmittable UV light. Devices such as SMA connectors and fiber end ferrules are useful in reducing or minimizing alignment issues.

With all types of UV light transmission fiber bundles, as opposed to single core fibers, present the problem of light lost in the interstitial spacing between the fibers. However, single core fibers present flexibility problems with respect to proper treatment placement. It has been discovered that the ends of fiber bundles can be fused (such as with hexagonal interfitting) with minimization of interstitial spacing for a short distance of the fiber at the light uptake position, with the remainder of the fiber being maintained in the flexible fiber bundle configuration.

Endoscope Carrier:

A flexible endoscope such as a pulmonary bronchoscope has an insertion tube section adapted to be inserted into passageways of an organ such as bronchia of a lung and typically has about a 5 mm diameter for a typical bronchoscope. Diameters of insertion tube sections in other endoscopes vary in accordance with parameters of organ dimensions in which a particular endoscope is to be used. The long fiber optic cable is inserted through the instrument channel ("biopsy channel") and insertion tube where it extends to the distal tip and beyond, as controlled:

A bronchoscope, and other endoscopes are provided with various passageways such as air/water nozzles, water jets, white illumination light and viewing passageways (CCD unit) and a biopsy channel. While the various passageways in the endoscope have fixed-in-place elements or fixed end caps, the biopsy channel or instrument insertion channel, is of necessity a hollow channel through which instruments such as biopsy tools are inserted and removed (a biopsy tool must be removable for retrieval of biopsy samples) and which allow for biopsy tool extension from the endoscope end. To allow for insertion and removal, without binding, and to accommodate mechanically operable tools, the "biopsy channel" is relatively large and is on the order of about 2.2 mm to about 3.7 mm diameter depending on models and types of endoscopes.

In accordance with this embodiment, the relatively long UV-C transmitting, low attenuation fiber optics cable is sized (including cladding) with a diameter less than that of the biopsy channel such that it can be inserted into the biopsy channel in place of the biopsy tool. In an embodiment for a bronchoscope, the length of the fiber optic cable is about two meters with one meter extending between the UV-C light source and the bronchoscope and the other meter of fiber optic cable is contained within the biopsy channel when being used to treat internal pathogen sites. As with biopsy tools the fiber optic may be extendible from the end of the bronchoscope with the smaller thickness of the fiber optic cable (on the order of 1-2 mm) being able to access smaller organ passageways than permitted with the 5 mm endoscope diameter. Control of such extension is effected by similar plunger mechanisms already used for effecting the taking of biopsy samples with distance markings A low attenuation loss UV-C transmission fiber optic cable with dimensions of 1.0 meter by 0.4-0.6 mm diameter (suitable for use in an endoscope biopsy channel), with cladding and optical connectors at both ends is adapted for low attenuation loss coupling to the UV-C light source such as with the "pig tail" connector and insertion into the biopsy channel of the endoscope. Butt coupling of fiber ends to the die of the LED provides another type of optical connection as do various types of lenses as described above. Movement control is that of control of the endoscope with simple extension and retraction control of movement of the fiber optic cable beyond the distal tip and peripheral control of any optical needles on a distal end of the optical cable.

In a further embodiment, a common hand-held instrument known as an otoscope is modified to contain UV-C LEDs instead of, or together with, white LEDs with a short, low attenuation fiber optic cable for use in treating the more easily accessible in vivo sites of the ear, nose, throat and genitalia (e.g., for treatment of HPV) with the speculum carrying the fiber cable for UV-C light application to these sites. For applications such as for treatment of middle ear infections the otoscope like device includes an extendible fiber optic cable extension for introduction into the Eustachian tube leading into the middle ear In embodiments where there is a single path for insertion, where only extent of insertion is needed, the "endoscope" may be rigid (as physiologically permitted) and the definition of "endoscope" as used herein is an in vivo UV-C light introduction device and includes both site viewing and non-viewing capability. No white light is required for the latter application devices.

In an embodiment with an extendible fiber optic cable, the cladding around the end of the fiber optic cable may be made UV-C light transmittable and the corresponding fiber ends may be treated to permit lateral light emission whereby, with cable extension the UV-C light is able to extend in 360 degrees, a circumferential direction similar to that of a lantern, with greater emission impingement of the UV-C light on pathogen sites in an organ such as a lung.

Flush end positioning of the fiber optic cable in the biopsy channel may be effected with any number of means such as position detents and positioned external collars and the like. Different endoscope devices require fiber optic cables with different dimensional parameters and the cable are sized accordingly.

The single length fiber optic cable or even fully abutted length of fiber optic cable serves to minimize the effect of UV-C light attenuation. Accordingly, a 5×5 array (25 LEDSs) of UV-C 265 nm LEDs with a power output of 40 mW per LED provides an aggregate 1 watt of output power (minus any nominal amounts of attenuated power). Similarly, a 7×7 array (49 LEDs) of LEDs provides about 2 watts or nominal output power. Since about 200 mW per square centimeter of output power (200 mJ/cm$^2$ of energy per second) literally deactivates or destroys pathogens of viruses and bacteria in under a second with pathogen destruction being ensured with effectively dialed down power. At that power level, the pathogen removal in under a second provides an effective treatment in a time span less than one that would result in harm to any more resistant and self-healing healthy cells and tissues in the vicinity of pathogen infected sites. Such short exposure times also facilitate the treatment of multiple infection sites in reasonably short therapeutic sessions. LEDs with other power levels reduce or even eliminate the need for arrays and their attendant connection and optical coupling complications.

In otoscope type devices and their more proximate distance between the fiber optic cable and the treatment site, arrays of 3×3 (9 LEDs) or even 2×2 (4 LEDs) are effective and require less power with suitable battery powering.

It is generally understood for all embodiments herein that the number of LEDs are described as being in arrays for symmetry and the number is not limited thereby. Furthermore, it is the output power which is the consideration and not the actual number of LEDs. A single high powered LED is preferred because of lesser complications and greater ease in light collection and transmission and in device servicing.

With the ability to ramp up output power of optimized DNA/RNA disruption specific 265 nm LEDs, more resistant cancer cells are able to be targeted for effective removal. This is an effective procedure against cancerous tumors in conjunction with surgical excision of tumors from tissue walls with the UV-C light being able to treat sites not accessible to surgical treatment such as tissue walls of the cancer site to kill residual cancerous cells or to prevent recurrence. In addition, the "lantern" section of fiber optic cable extending from the endoscope in the second embodiment can actually be dragged into contact directly over the cancer site to maximize cancer cell destruction in a very targeted manner.

To further enhance UV-C light penetration into cancer tissue, the "lantern" section may be integrated with an array of UV light conductive fiber needles in a toggle swivel structure (permitting the structure to be inserted into the 2.2 mm to 3.7 mm biopsy channel and then expanded in a direction normal to the cable after clearing of the "lantern" section from the end of the endoscope). Alternatively, the needles remain around the "lantern section" whereby the needles in both embodiments successively penetrate and treat deeper portions of a cancerous site. To prevent impeding with the biopsy channel walls during cable insertion, the needles are retracted and extended upon proper positioning. A simple push/pull mechanism enables the needles to flatten or extend as appropriate. The term "needles" is general, referring mostly to the overall shape of the dispersing fiber ends. The ends of the needles should not be sharp enough to puncture tissue or organs, except when such puncturing is desired. Hollow E-BUS and similar type of aspiration needles commonly used for biopsy examination of normally not accessible areas (with about 1 mm diameter hollows) can be used as steering carriers for UV carrying fibers if small diameters for direct and close application of pathogen killing UV light directly within tumors. Multiple penetrations can, over the course of treatment, significantly deactivate malignant tumors which are otherwise inaccessible to surgical removal. Brain tumors with highly restricted access may also be effectively treated with the minimally sized UV carrying fibers.

To further facilitate cancer cell penetration, higher power UV-A light LEDs may be incorporated in the LED array and operatively activated after each UV-C application to ablate and remove layers of dead cancer cells. Water jets and suction, from the endoscope may be utilized to further facilitate the removal of dead cancer cells. The white light of the endoscope is properly utilized to illuminate treatment sights. Alternatively, white light LEDs may be incorporated into the LED array and the white light is transmitted along multi-channel fibers. This may be useful for rigid endoscopes, which essentially have one illuminated channel for everything.

Once UV-C treatment has been completed either on a site by site basis or in successive procedural operations, the fiber optic cable may be removed and the biopsy tool may be inserted into the biopsy channel for normal operation. A fiber or lens may include additional treatments such as a AR coating to further enhance light transmission.

The following is a tabular listing of different embodiment fiber assemblies. These are merely illustrative and other assemblies including variations in structures and components are possible:

Table of Assemblies

Fiber Assembly 1:
 LED is butt-coupled to a 1 mm or 2 mm diameter fiber and tapered to 500 um. The taper is further coupled to an external 500 um or 600 um fiber and may include an end-treatment at distal-end of fiber.
Fiber Assembly 2:
 LED is butt-coupled to a (single core or bundle) fiber diameter matching the die/LED size and tapered to a narrower point, ideally 500 um. The taper is further coupled to an external 500 um or 600 um fiber, and may include an end-treatment at distal-end of fiber.
Fiber Assembly 3:
 LED is butt-coupled to a fused core fiber bundle.
  This allows that fiber bundle thickness to achieve a 1 cm bend radius.
  A further benefit to a fused core fiber bundle is a single fiber length with no coupling interruptions.
  The many fibers in bundle allow for additional light uptake opportunity, increasing chance of power-output thru the fiber.
  May include an end-treatment at distal-end of fiber.
Fiber Assembly 4:
 A single length (single core or bundle) 600 um fiber cable is butt-coupled to an LED and may include an end-treatment at distal-end of fiber.
Fiber Assembly 5:
 LED coupled to fiber with an optical lens such as a TIR and further focused into a 500 um taper which is then coupled into a 500 um or 600 um external fiber and may include an end-treatment at distal-end of fiber.
Fiber Assembly 6:
 e LED coupled to fiber with an optical lens such as a TIR and further focused and coupled into a 500 um or 600 um external fiber where the proximal end of the external fiber includes a focusing lens to bring the light beam to a narrower point of 500 um, and may include an end-treatment at distal-end of fiber.
Fiber Assembly 7:
 LED coupled to fiber with an optical lens such as with aspherical lenses and focused 500 um-800 um and further coupled to an external fiber where the proximal end of the external fiber includes a focusing lens to bring the light beam to a narrower point of 500 um, and may include an end-treatment at distal-end of fiber.
Fiber Assembly 8:
 LED coupled to fiber with a 30° lens covering the LED and a secondary optical TIR lens at a focal length such as a pair of aspherical lenses to collimate and further focus light into a single length external fiber cable of 600 um and may include an end-treatment at distal-end of fiber.

Fiber Assembly 9:
 500 um or 600 um fiber is coupled directly to a laser or coherent LED (LED with laser-like focusing qualities), and may include an end-treatment at distal-end of fiber,
Fiber Assembly 10:
 LED is focused into narrow fiber diameter sing mirrors such as off-axis parabolic or ellipsoidal mirrors,
Fiber Assembly 11:
 LED coupled to fiber with an optical lens such as a 4-in-1 lens (for large LED size) with a 30° or angle of fiber acceptance degree, and focused into fiber either with butt-couple or lens with an appropriate focal length. Fiber may be further tapered or include additional optical couplings to bring the beam diameter to an acceptable diameter size per application.
  The 4-in-1 lens allows the individual beams emitted from respective dies to collimate into a single beam.
  This allows the light entering into the fiber to exit mostly intact, thereby avoiding crashing into the walls of the fiber at unacceptable angles.
Fiber Assembly 12:
 LED coupled to fiber with an optical lens, such as with a 30 degree or angle of fiber acceptance degree, and focused into a fiber either with a butt-couple or appropriate focal length lens or series of lenses. The fiber may be further tapered or include additional optical couplings to bring the beam diameter to an acceptable diameter size per application.
  This allows the light entering into the fiber to exit mostly intact avoiding crashing into the walls of the fiber at unacceptable angles.
Fiber Assembly 13:
 One or more LEDs each coupled to an optical fiber or optical fiber end-part of a multiple fiber combining assembly. Coupling method may be with a butt-couple, a lens, or other optical assembly. The output of these assemblies is configured to combine into a singular optical fiber with methods including split pigtail fiber optic combiner/splitter assembly, such that the power of the LEDs is greater than that of a single LED.

The above and other objects, features and advantages of the invention will become more evident from the following discussion and drawings in which:

SHORT DESCRIPTION OF THE DRAWINGS

FIG. 5 shows the prior art endoscope connection end with its outgoing electrical connections to the light source and the fiber optic light guide for the incoming light from the light source;

FIG. 6 shows a prior art extended multi-level light source and controller for the bronchoscope.

FIG. 7 is a right side sectioned view of an endoscope with a biopsy/suction channel accessed by a biopsy valve;

FIGS. 8 and 9 are end and section side end views of the endoscope of FIG. 7;

FIG. 10 is a side sectioned view of an otoscope;

FIG. 10a is an enlarged view of the insertion section of the otoscope of FIG. 10;

FIG. 11 is a schematic depiction of a UV emitting LED with a light collection optically coupled structure embodiment to a liquid light with an air-filled parabolic mirror light collimator;

FIG. 11a is the schematic depiction of FIG. 11 but with a liquid filled parabolic mirror;

Figure 14:
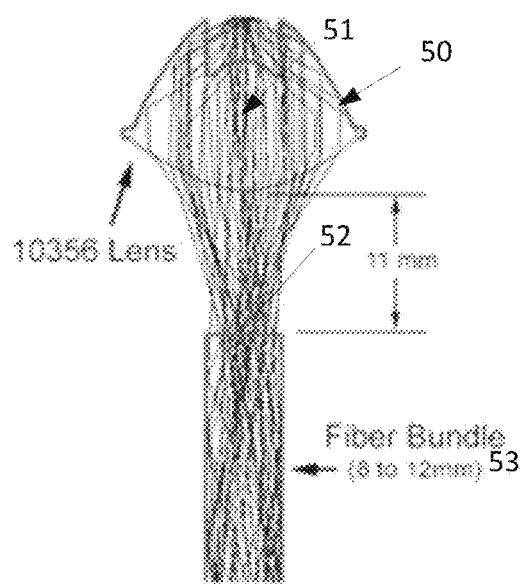
Figure 15:
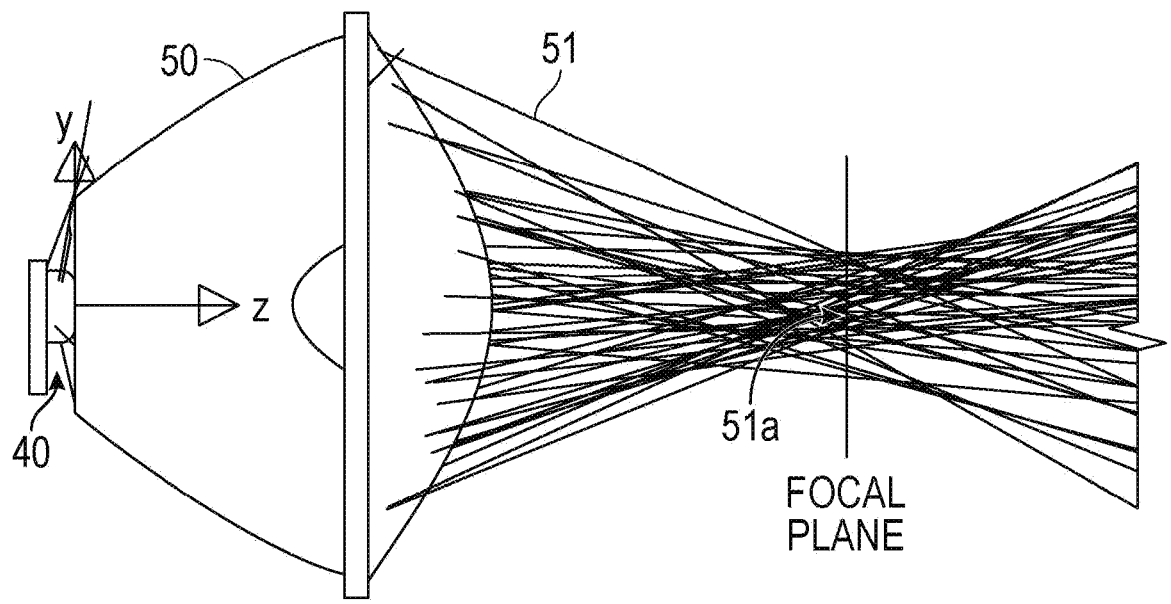
Figure 16:
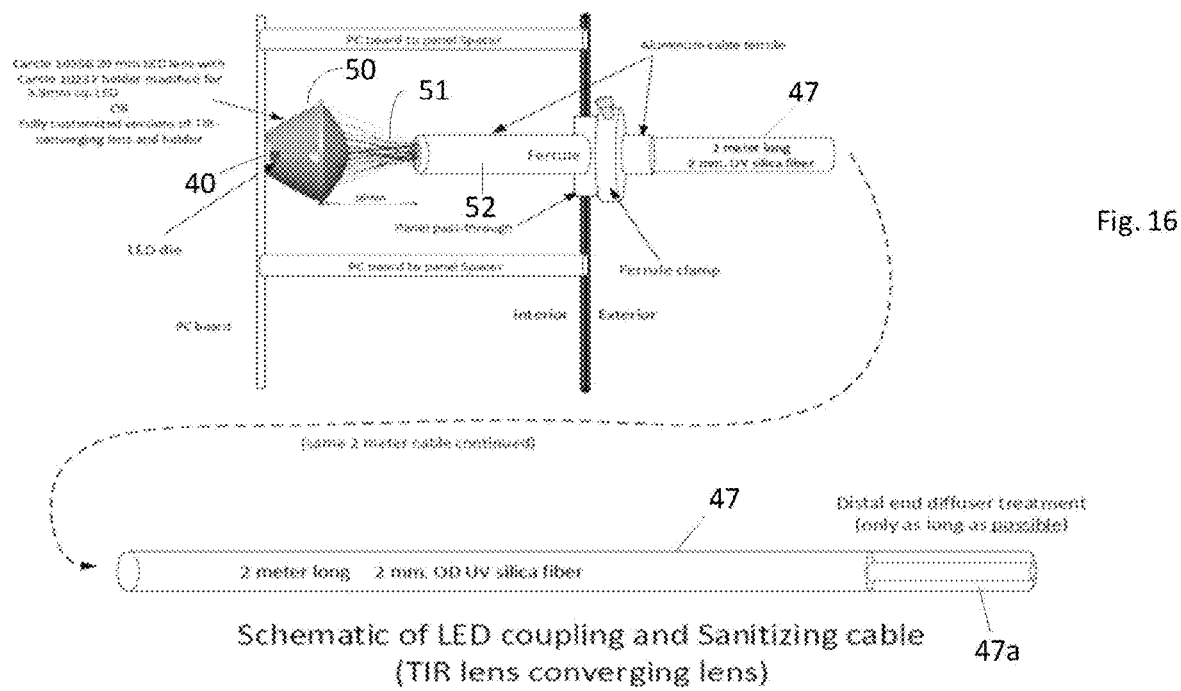
Figure 17:
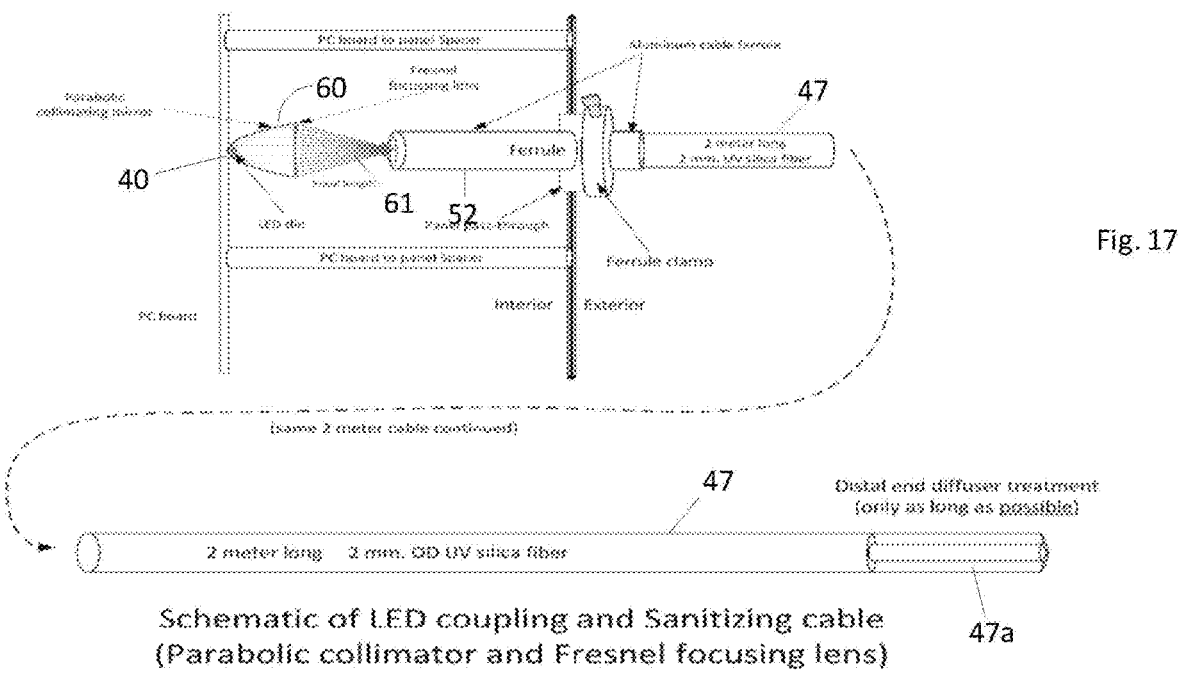
Figure 18:
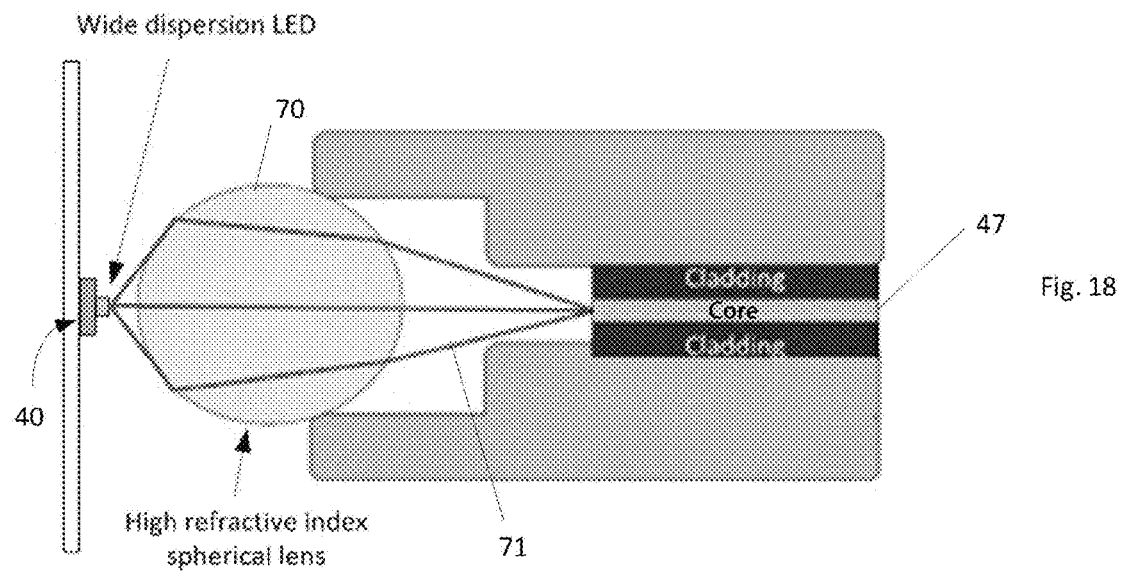
Figure 19:
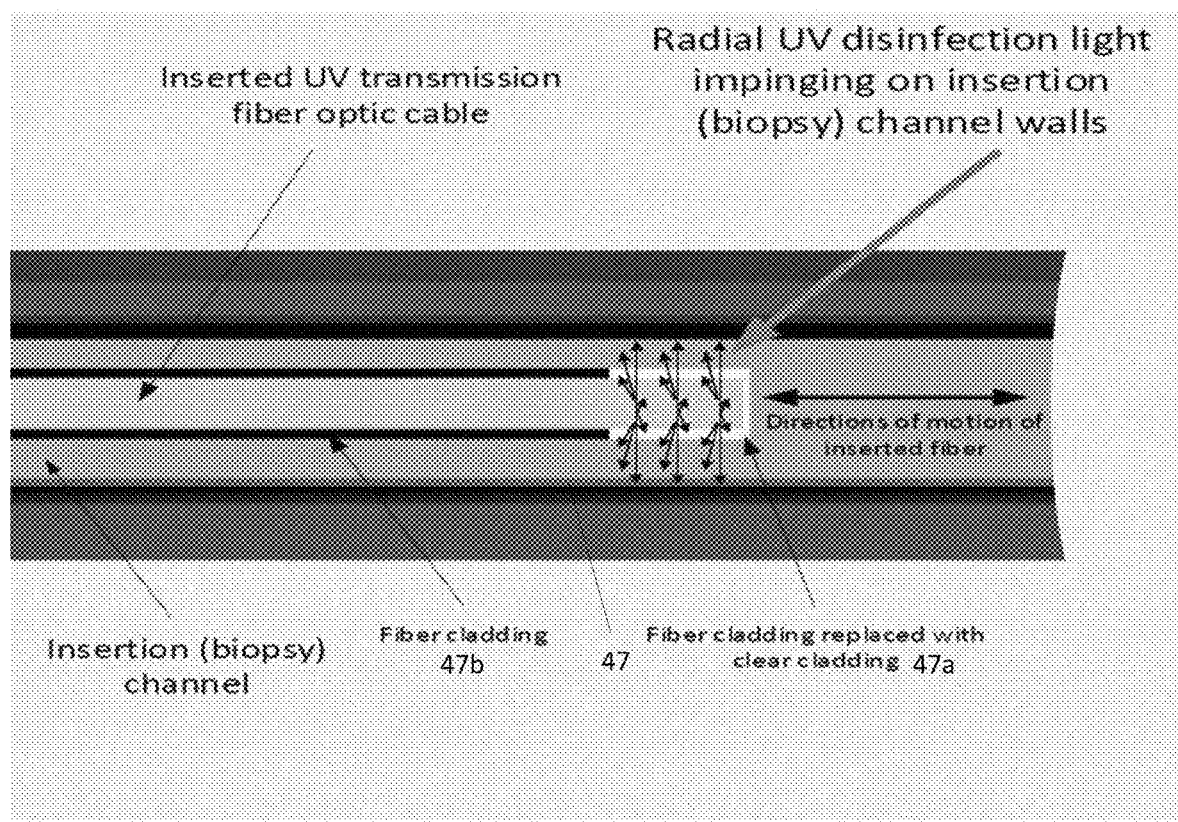
Figure 20:
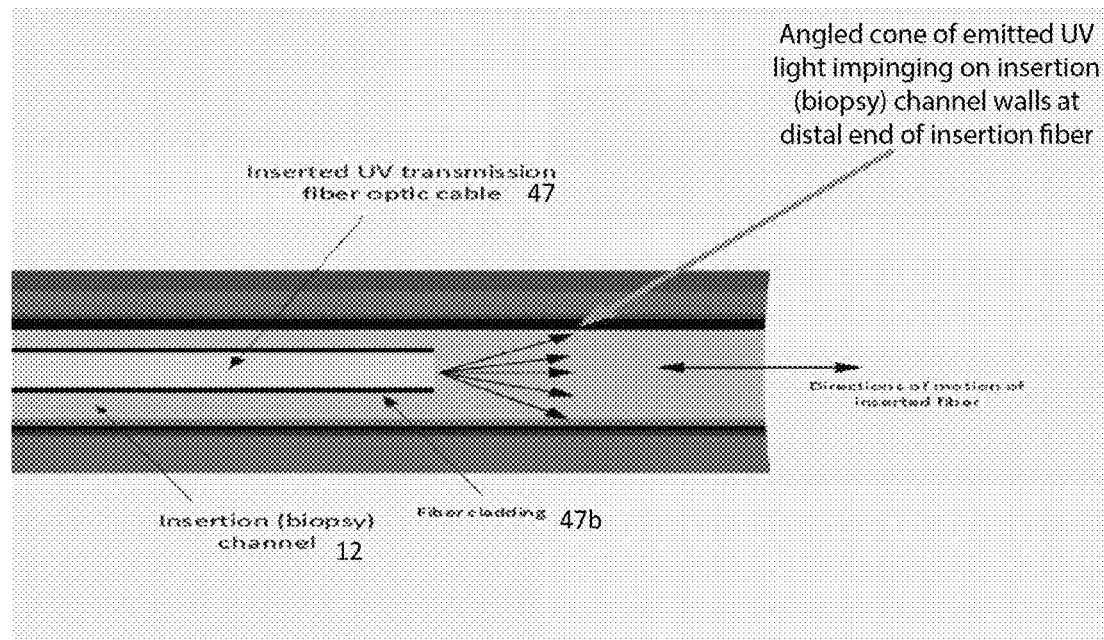
Figure 21:
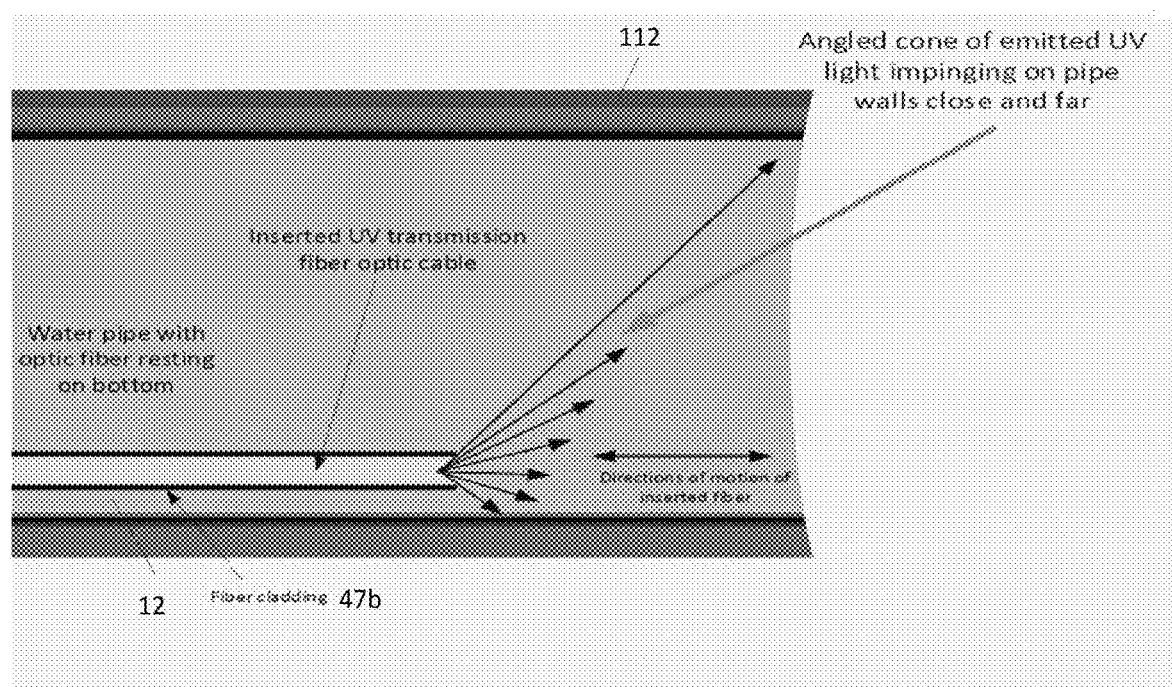
Figure 22:
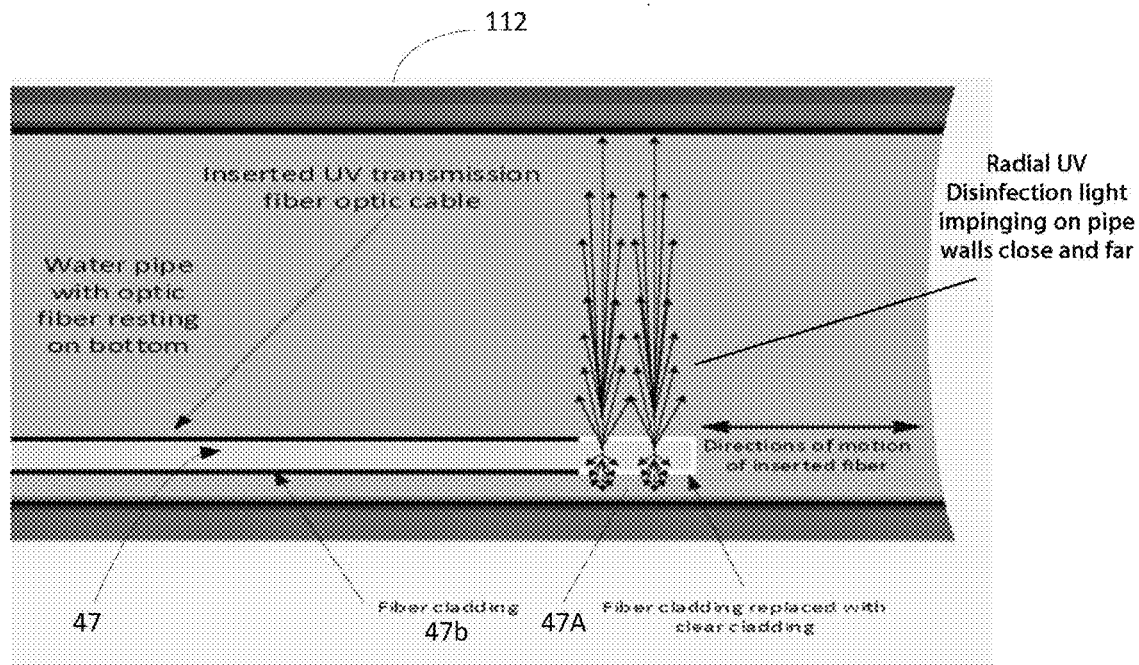
Figure 23:
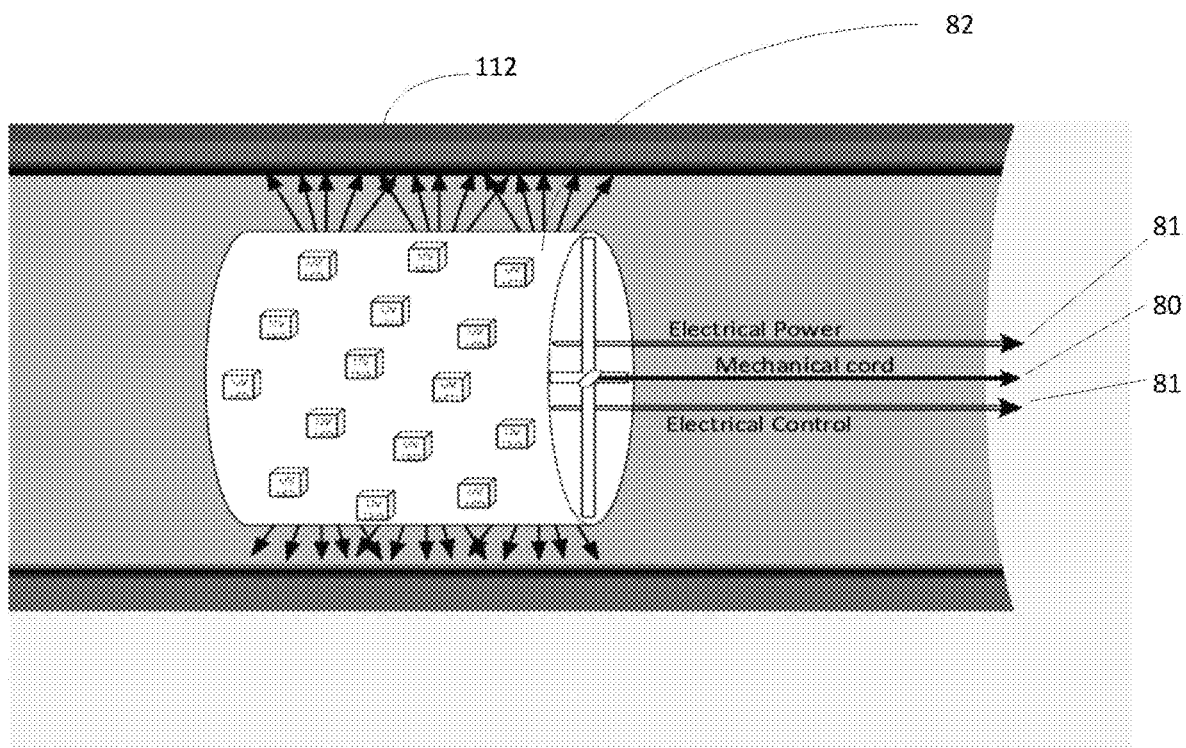
Figure 24:
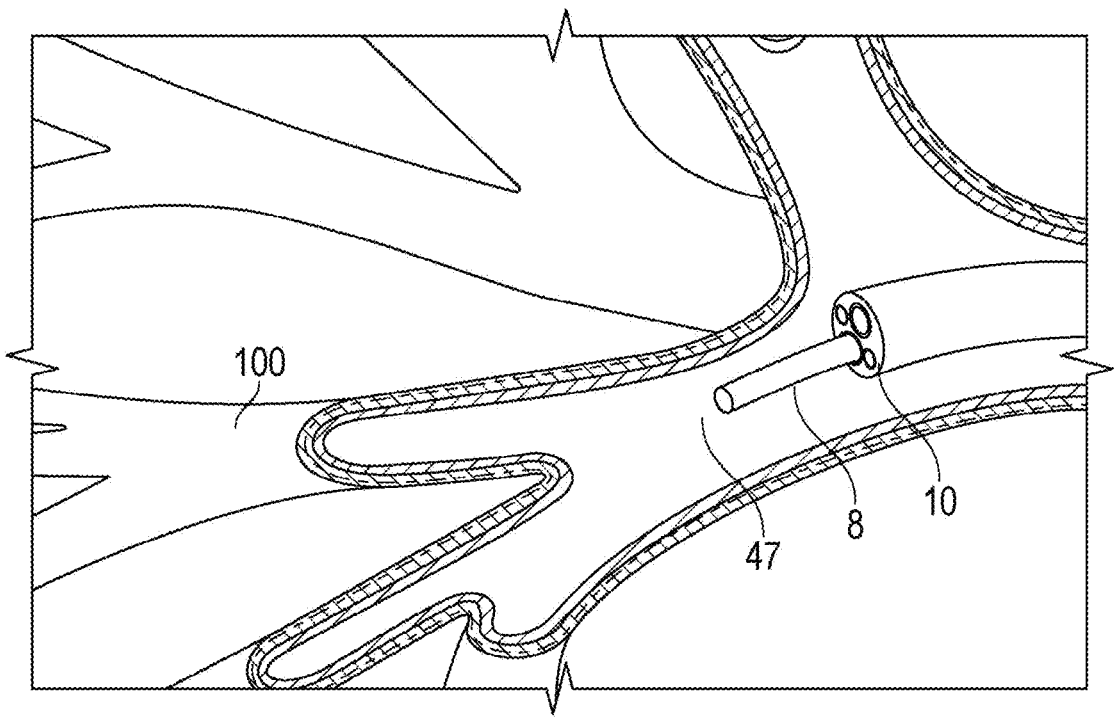
Figure 25:
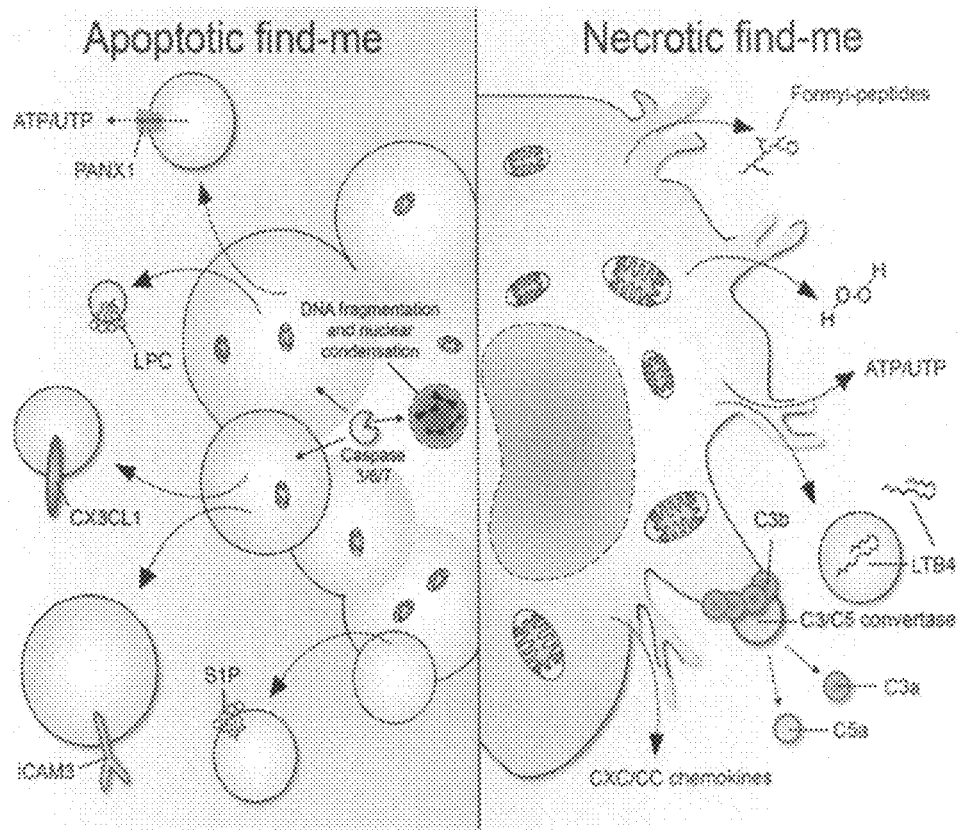

FIG. 14 schematically shows an LED coupled to the TIR lens of FIG. 16 with a focal focus of emitted light;

FIG. 15 schematically shows the collimation of light waves by the TIR lens and focusing direction of the collimated light into a fiber optic cable;

FIG. 16 is a schematic depiction of an embodiment of a UV light collection, transmission and emission structure using the UV light collection structure of FIG. 15 with TIR lens with transmission fibers of various dimensions;

FIG. 17 is a schematic depiction of an embodiment of a UV light collection, transmission and emission structure using the UV light collection structure of a parabolic mirror with a Fresnel lens as collimator and focusing elements in place of a TIR lens of FIG. 16;

FIG. 18 shows a high refractive index spherical lens collimating and focusing light into a fiber;

FIG. 19 shows an elongated UV light transmission fiber optic cable as inserted into a biopsy channel, with the fiber optic cable having a section of cladding removed at a distal end to permit radial UV disinfection light transmission to the interior walls of the biopsy/suction channel, during a withdrawal or insertion movement;

FIG. 20 showing the UV light transmission fiber optic cable with full cladding and with UV disinfection light being distally transmitted to the interior walls of the biopsy/suction channel as a conical impingement thereon, during a withdrawal or insertion movement;

FIGS. 21 and 22 are cross sectional views of a water pipe (about 4" ID) with the UV transmission fiber optic cable of FIGS. 19 and 20 effecting disinfection of the pipe from mildew, mold, fungus growth and pathogens which may have been generated with the greater impingement distance requiring longer dwell times or less than medical grade disinfection;

FIG. 23 shows an electrical transmission cable with an expanded distal end having an array of powered UV LED lights in closer proximity to the inner walls of the pipe;

FIG. 24 shows the end of a bronchoscope inserted into a main bronchial branch of a lung with a fiber optic extension into smaller bronchia;

FIG. 25 depicts DNA fragments resulting from UV deactivation of pathogens.

FIG. 26 shows a 40 mW UV 265 nm LED with 30 degree lens and related property charts.

Figure 30:
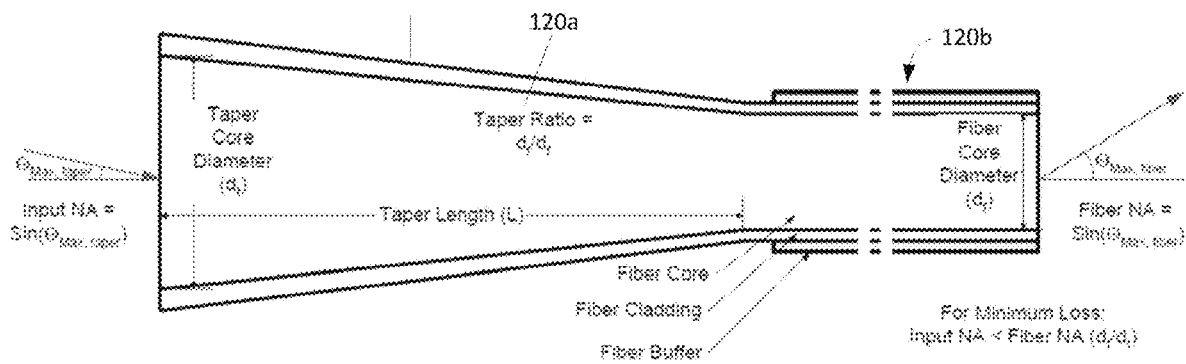
Figure 30A:
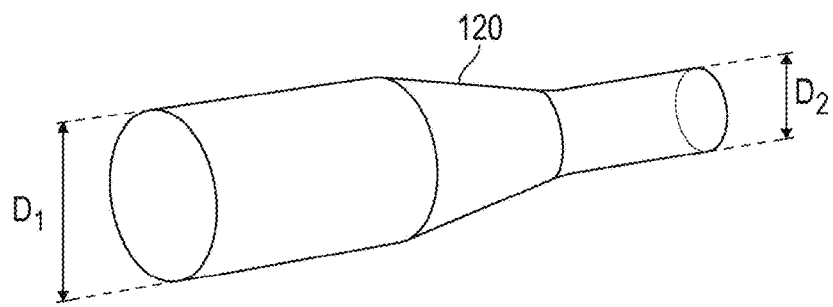
Figure 31:
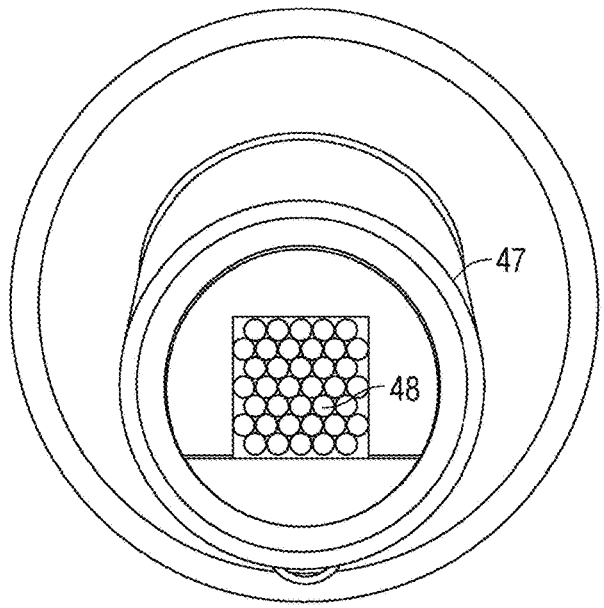
Figure 32A:
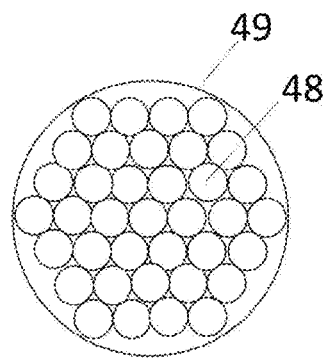
Figure 32B:
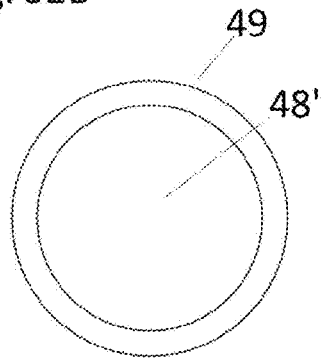
Figure 33A:
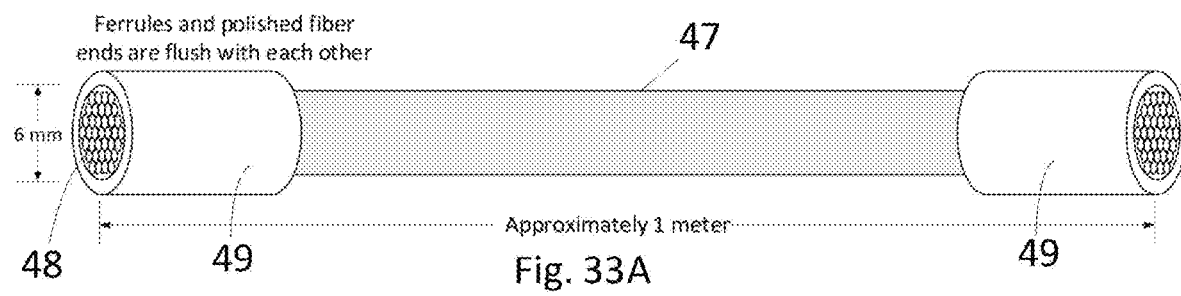
Figure 33B:
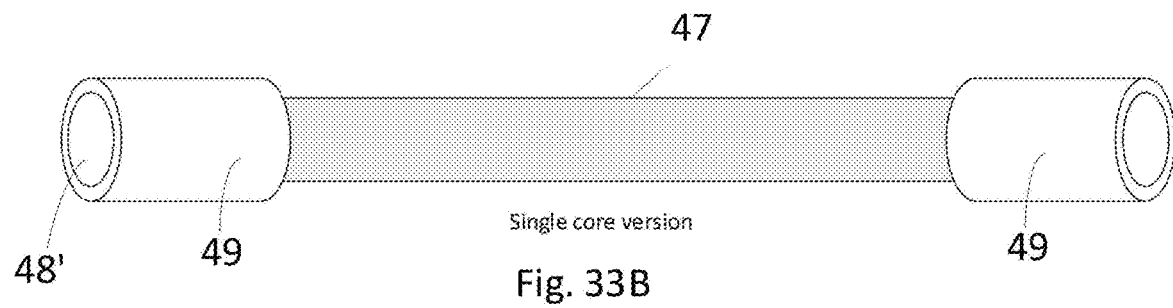
Figure 34:
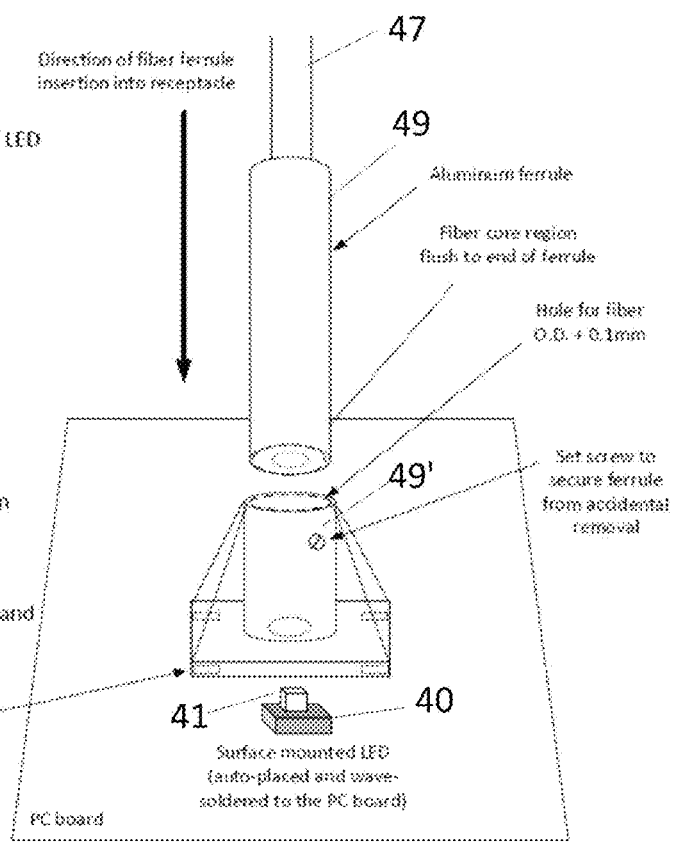
Figure 35:
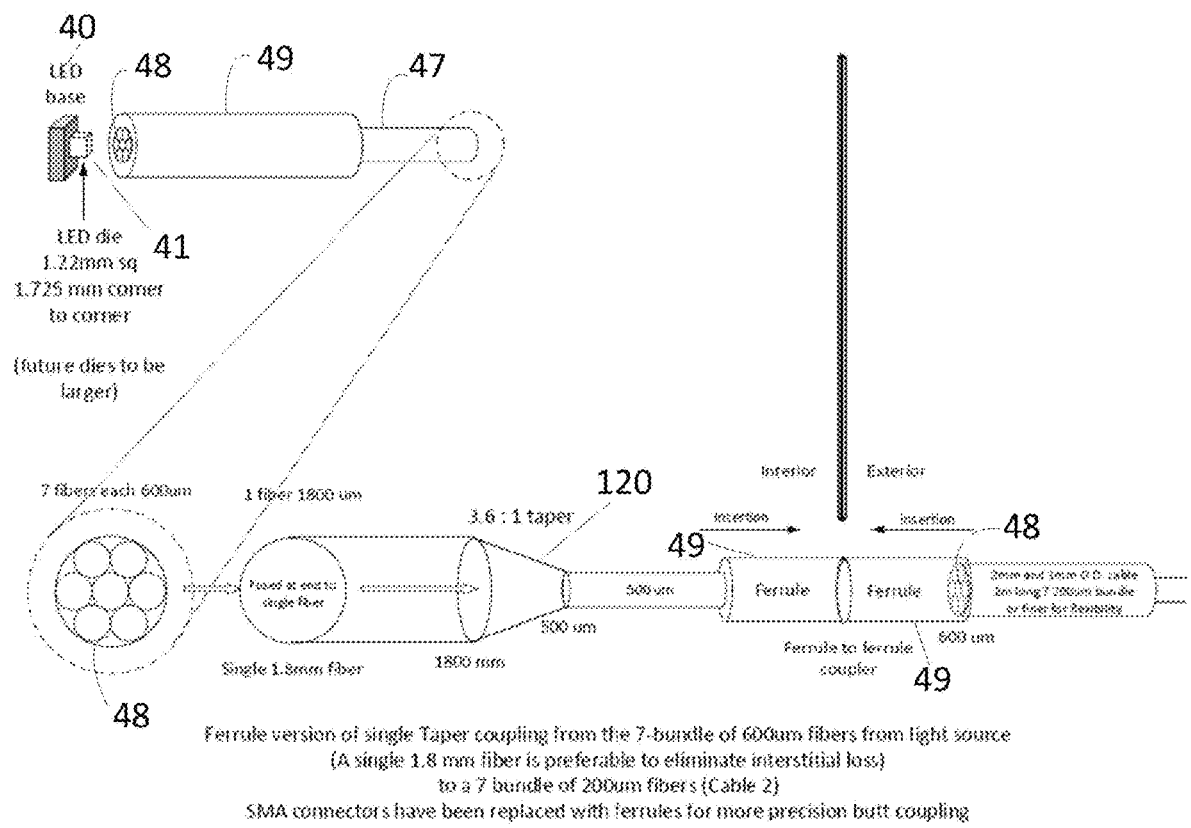
Figure 36:
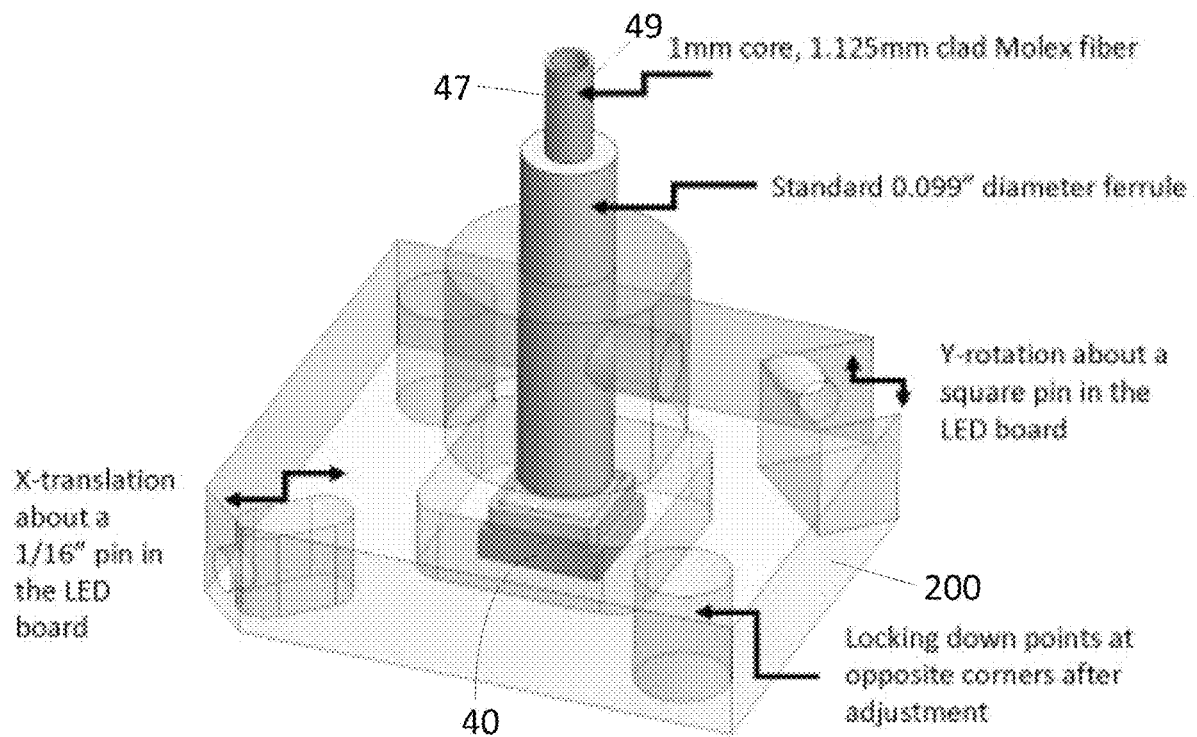
Figure 37:
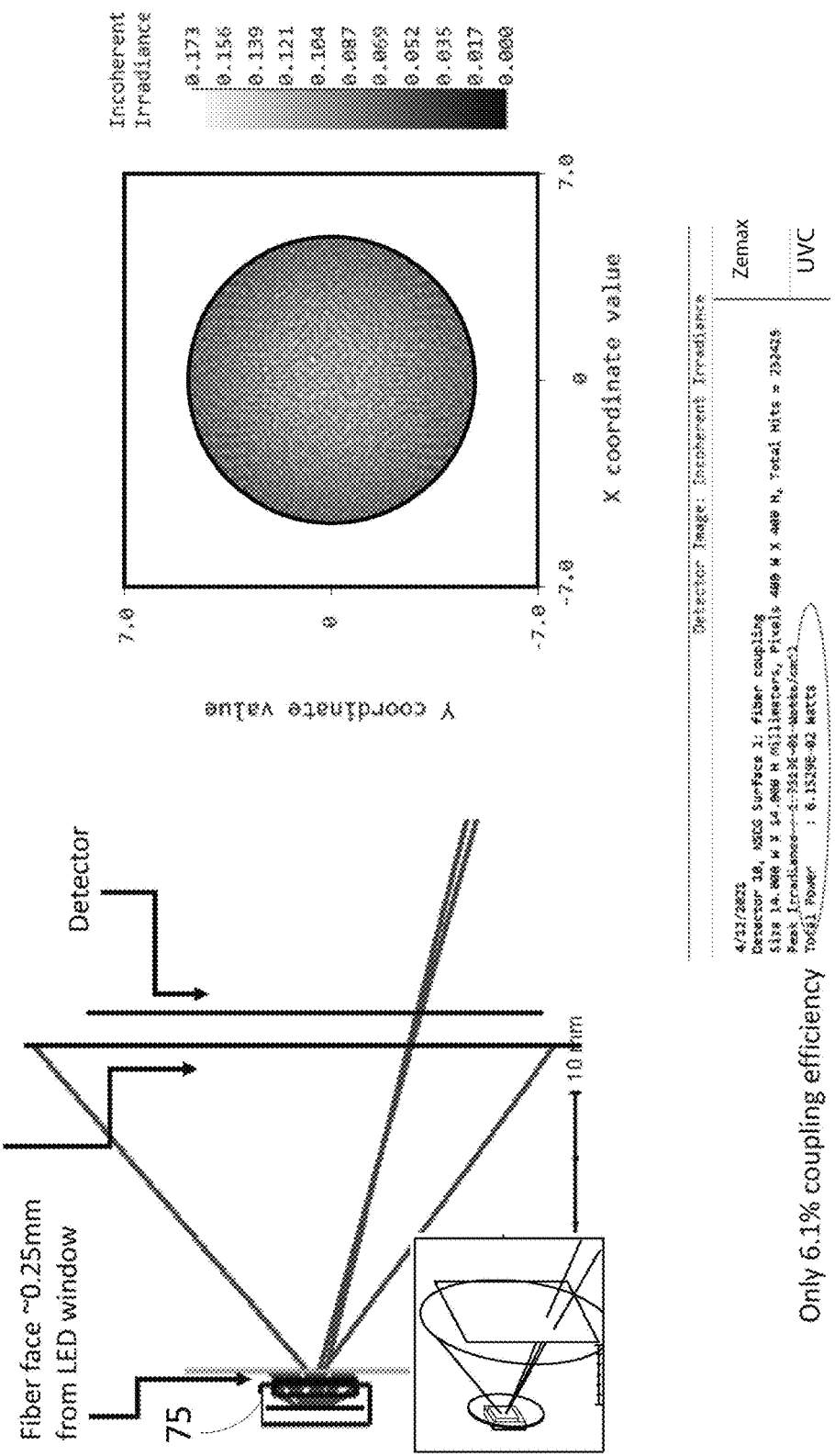

FIGS. 27; 28; and 29; show the 265 nm UV emitting LEDs of 75, 95 and 360 mW made for the method and devices herein with their respective radiation patterns;

FIGS. 30 and 30A shows cross sectioned and solid views of a tapered section of a UV light carrying fiber with light transmission conversion from D1 to D2 and from D2 to D1, depending on the direction of UV light flow;

FIG. 31 depicts a fuse core bundle with hexagonal interfitting shapes;

FIGS. 32A and 32B are illustration of a 37 1000 um core fiber bundle and a single core fiber respectively;

FIGS. 33A and 33B are side views of the fiber bundles of FIGS. 32A and 32B with alignment ferrules at both ends;

FIG. 34 shows a butt coupling of a fiber bundle against an LED with an end ferrule held in an alignment jig;

FIG. 35 is a UV light collection and transmission system using a butt coupling connection to an LED and a fiber taper element to effect transition between different diameter fibers;

FIG. 36 shows a butt coupling of a fiber bundle against an LED with an end ferrule held in an alignment jig with x-y plane adjustability;

FIG. 37 is a virtual simulation output of a 75 mW 265 nm LED butt coupled to a 1 mm fiber;

FIG. 38 shows the efficiency of a 2 mm fiber bundle butt coupled to the 75 mW LED;

FIG. 39 shows the radiation pattern of the LED of FIGS. 35 and 36;

FIG. 40 is a sensitivity graph of a ThorLabs S142C integrating sphere sensor for the Thor PM320E radiometer at 350 nm.

Figure 41:
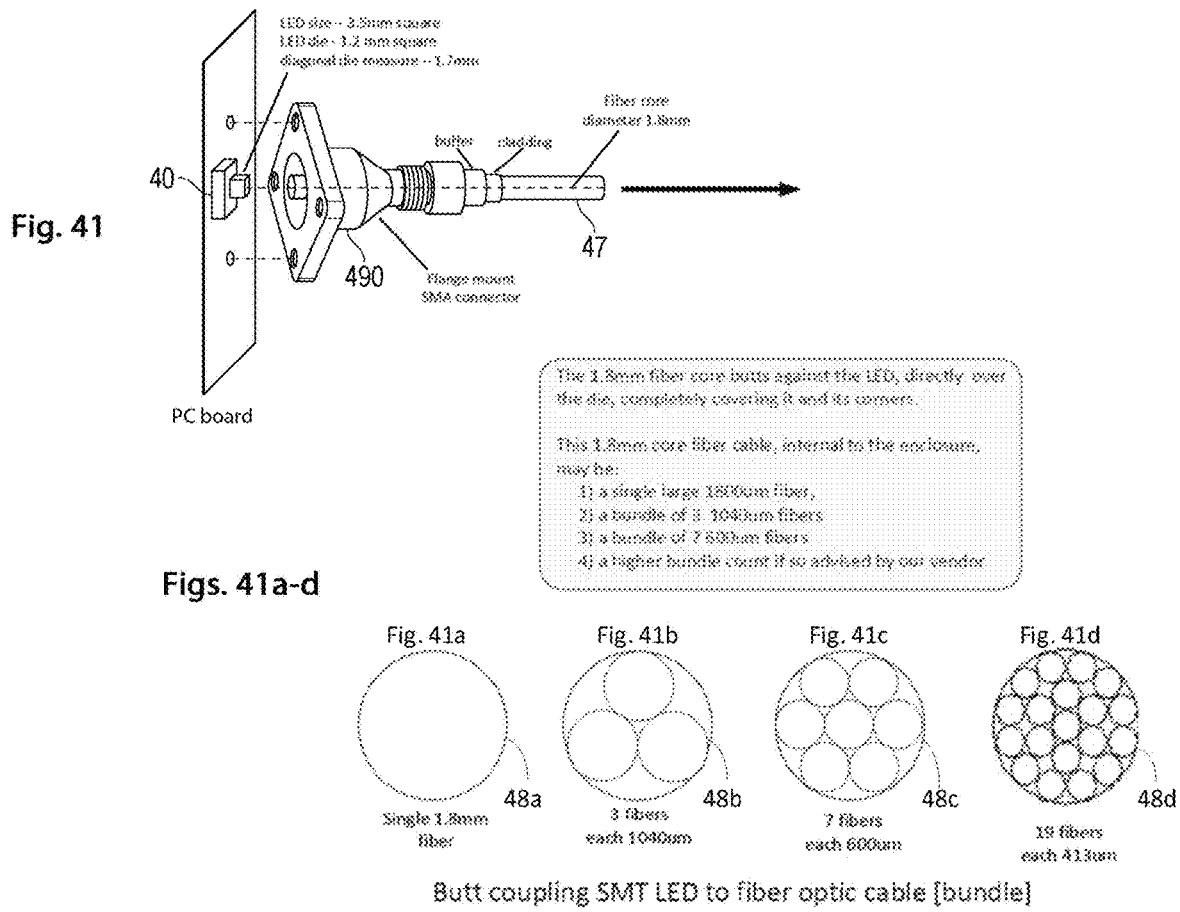
Figure 42:
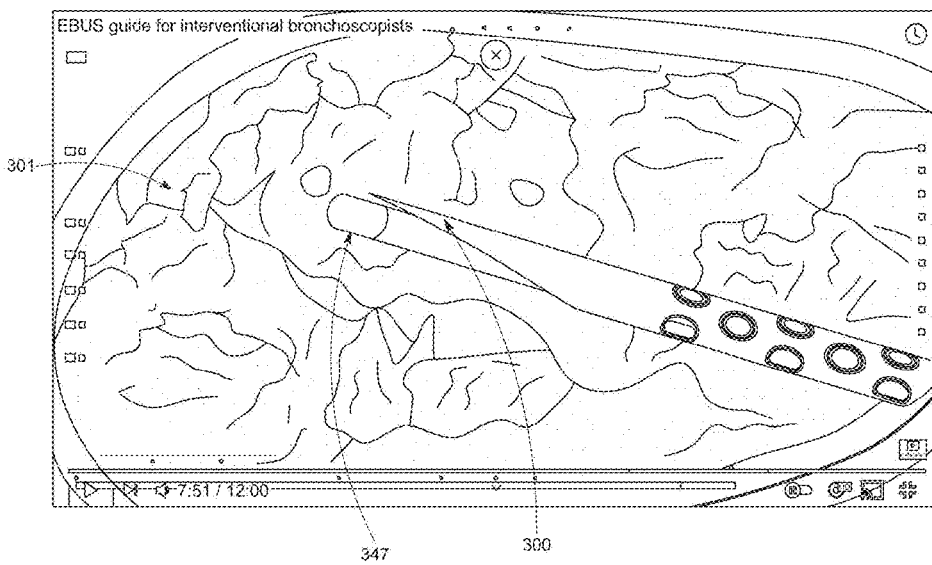
Figure 43:
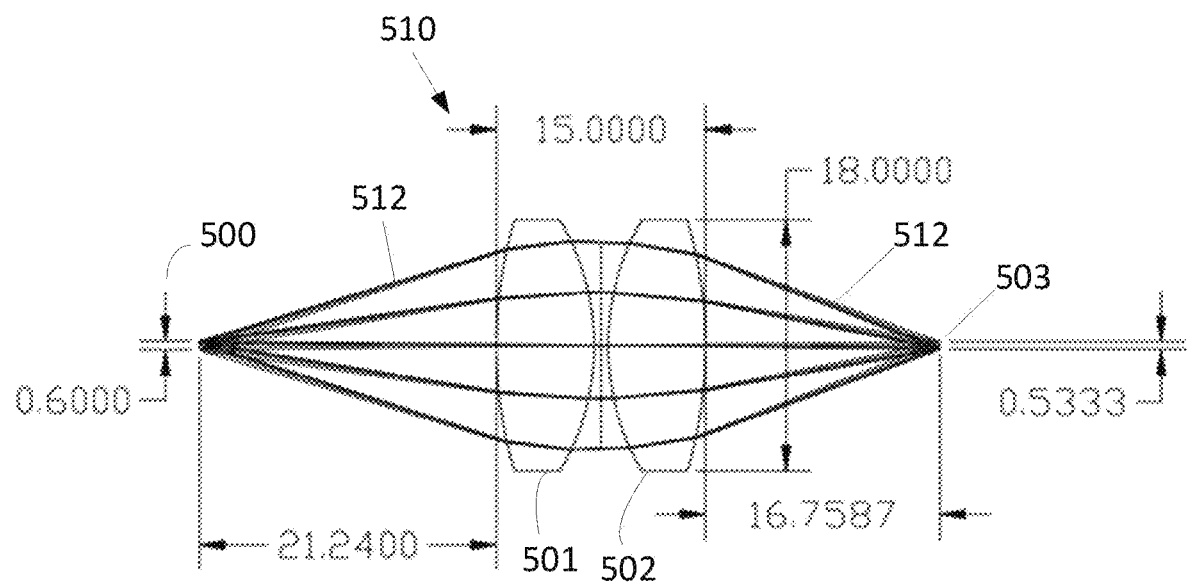
Figure 44:
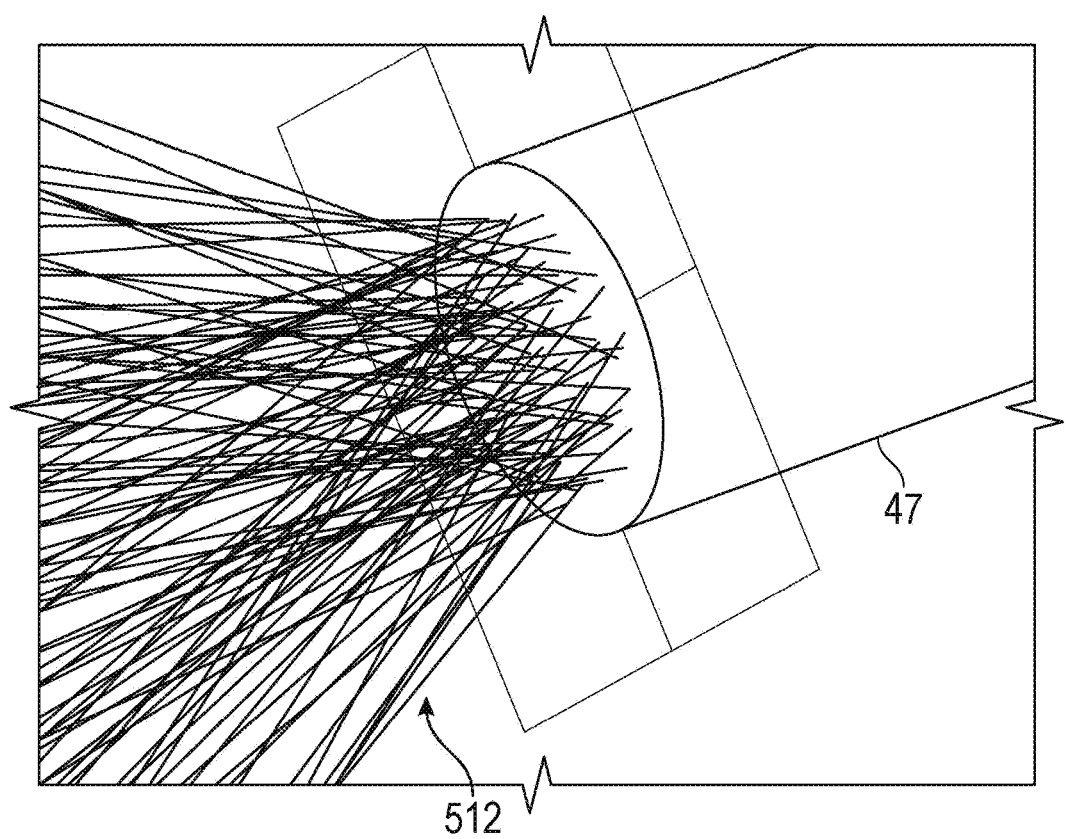
Figure 45:
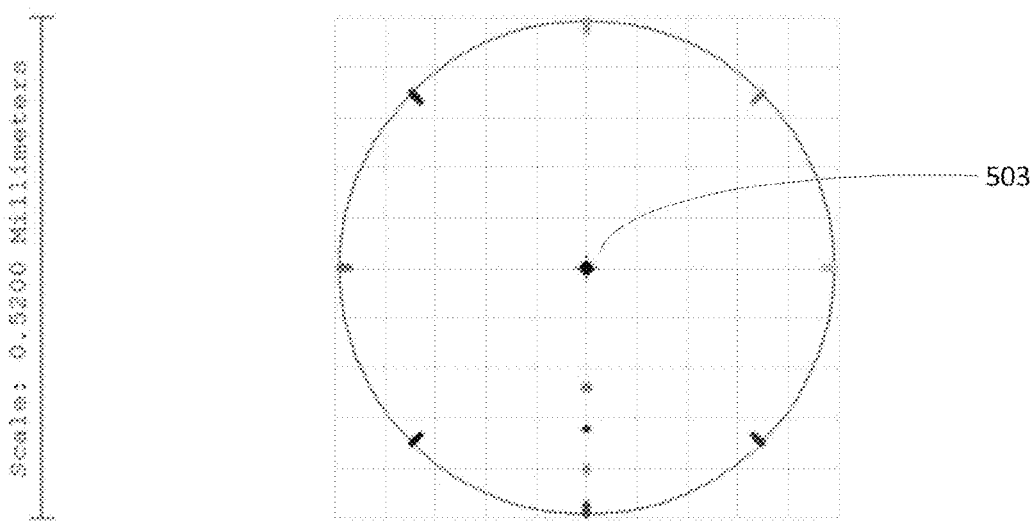
Figure 46:
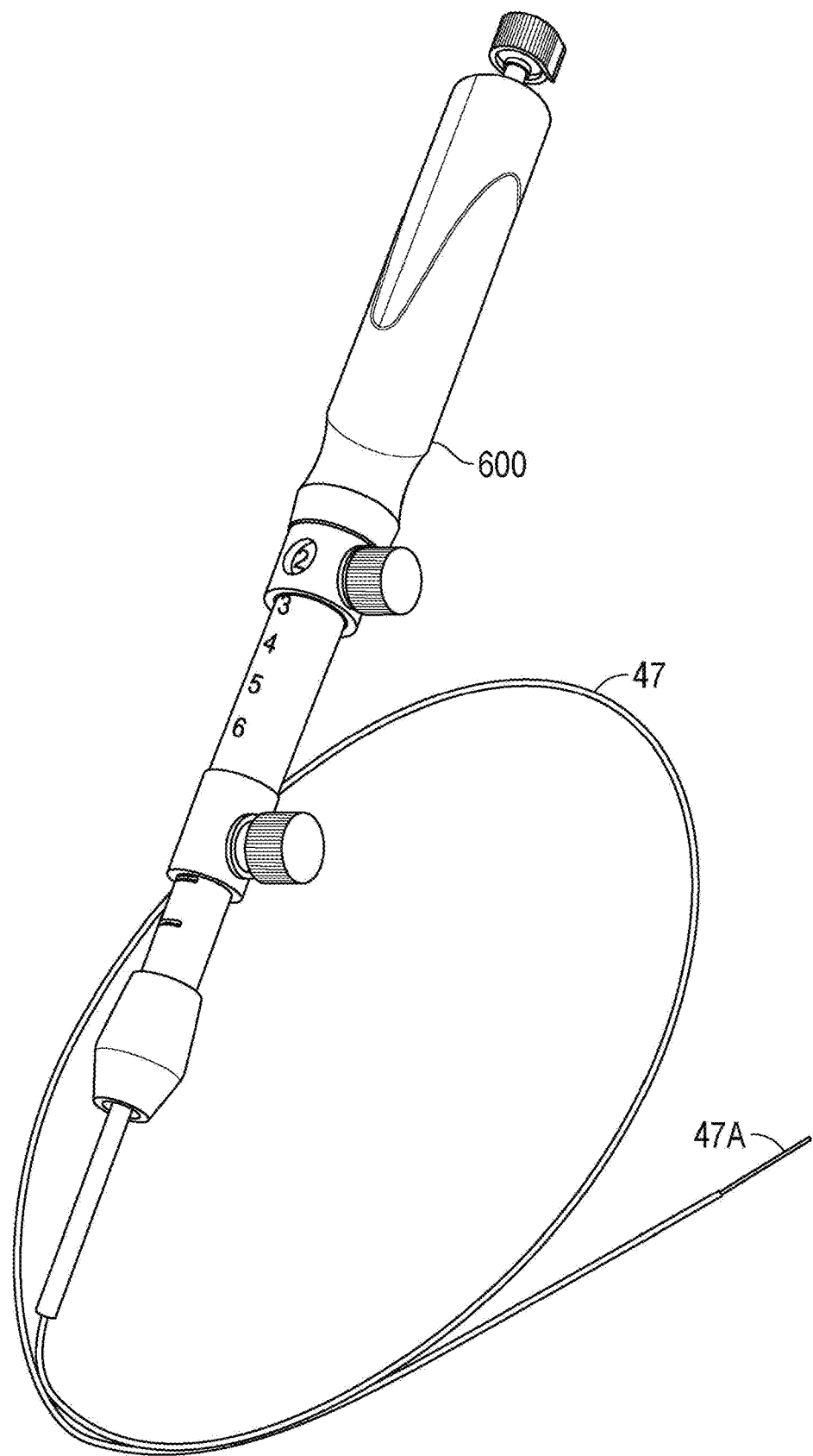
Figure 47:
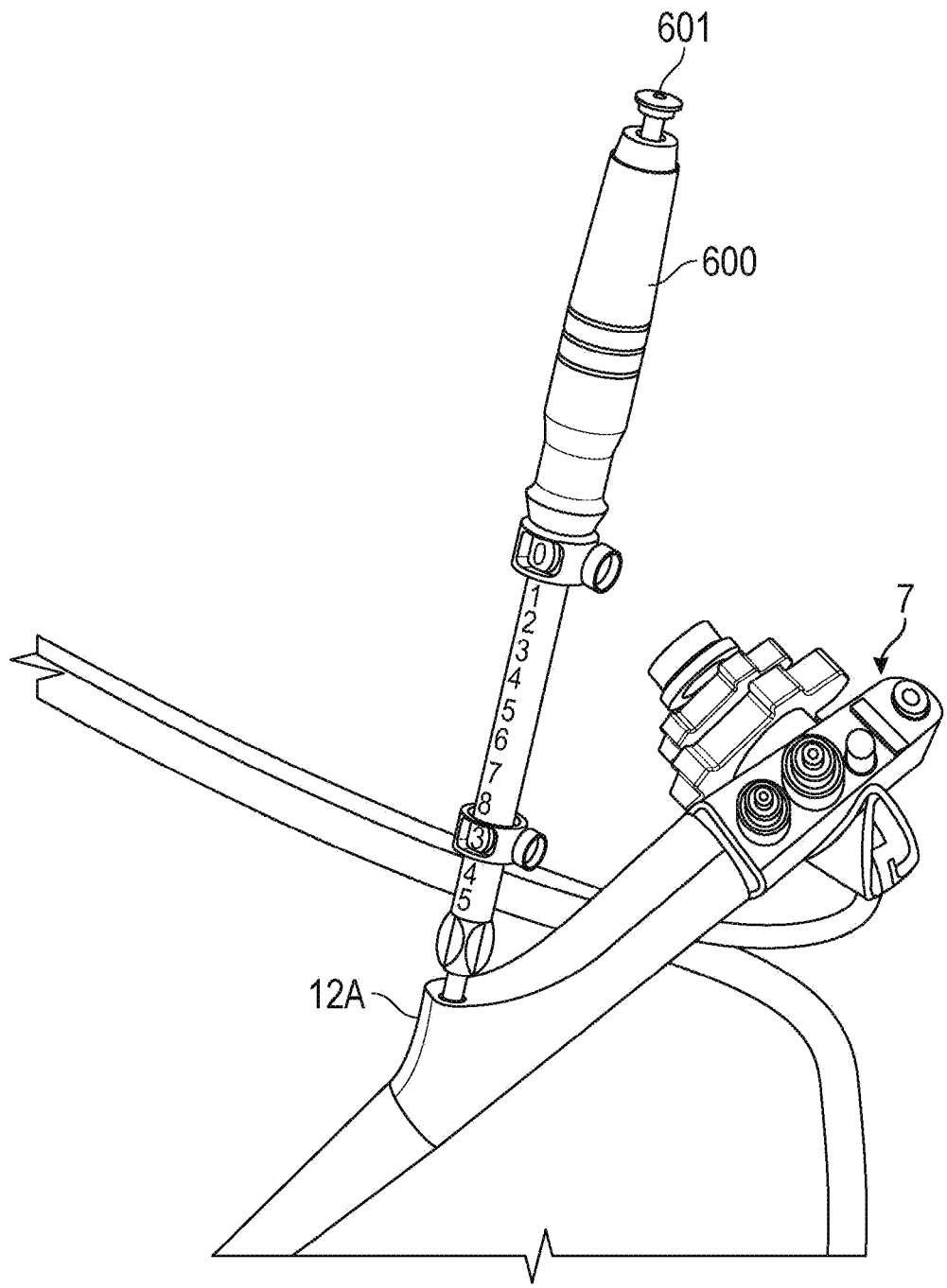

FIG. 41 shows a fiber bundle butt coupled to an LED with an SMA connector;

FIG. 41 a-d show configurations of the fiber bundle of FIG. 41 with single core, three fibers, 7 fibers and 19 fibers respectively;

FIG. 42 depicts an EBUS guide aspiration needle inserted into a tumor and containing a UV transmitting fiber;

FIG. 43 shows a UV light output from an LED with a 30 degree lens into a pair of aspherical lenses with a highly focused spot output;

FIG. 44 shows a ray trace of the light output of FIG. 43 into an optical fiber;

FIG. 45 is the dimensional output of the light in FIGS. 43 and 44;

FIG. 46 shows a manipulation handle with extending fiber optic fiber cable with contained fiber assembly system in the handle; and FIG. 47 shows the fiber of FIG. 46 inserted into the biopsy channel of an endoscope with extending control handle.

DETAILED DESCRIPTION AND DESCRIPTION OF THE DRAWINGS

Figure 1:
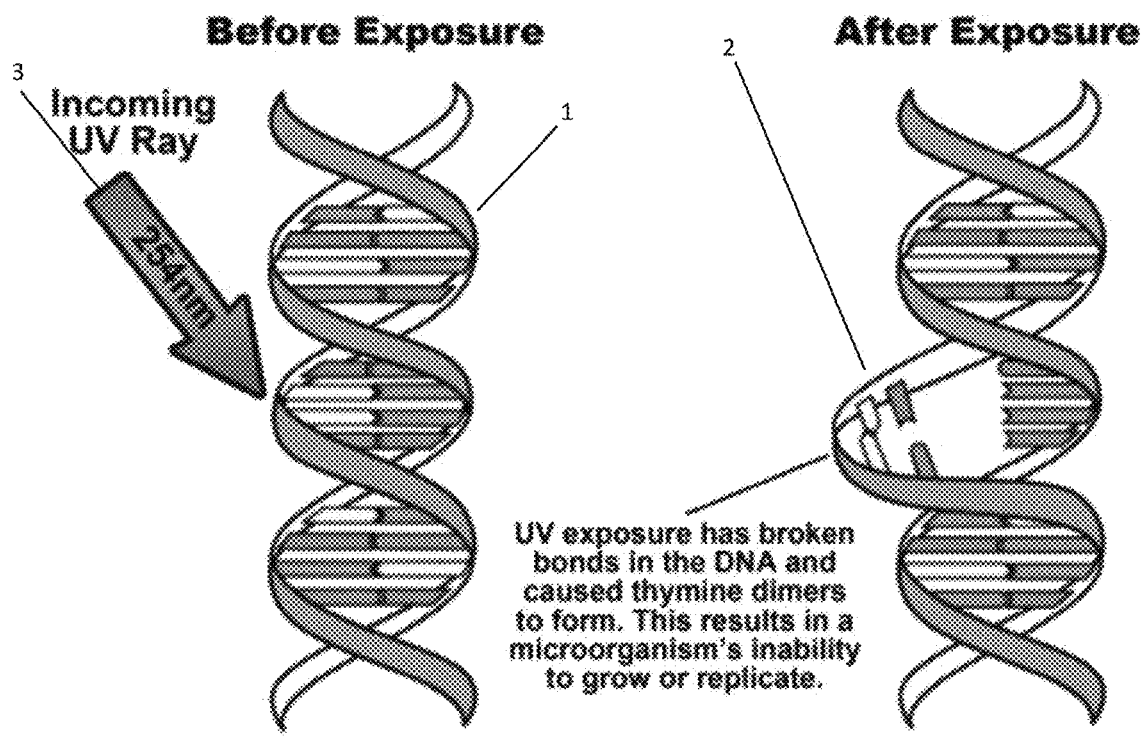
FIG. 1 depicts the effect of UV light on DNA with disruption of spiral supporting bonds.

With reference to the drawings, FIG. 1 schematically indicates the mode in which UV light deactivates and unravels the structure of DNA 1 of pathogens such as viruses. The UV 3 breaks the phosphorous bonding 2 which maintains the spiral structure of DNA (and RNA) thereby effectively killing it or destroying it.

Figure 2:
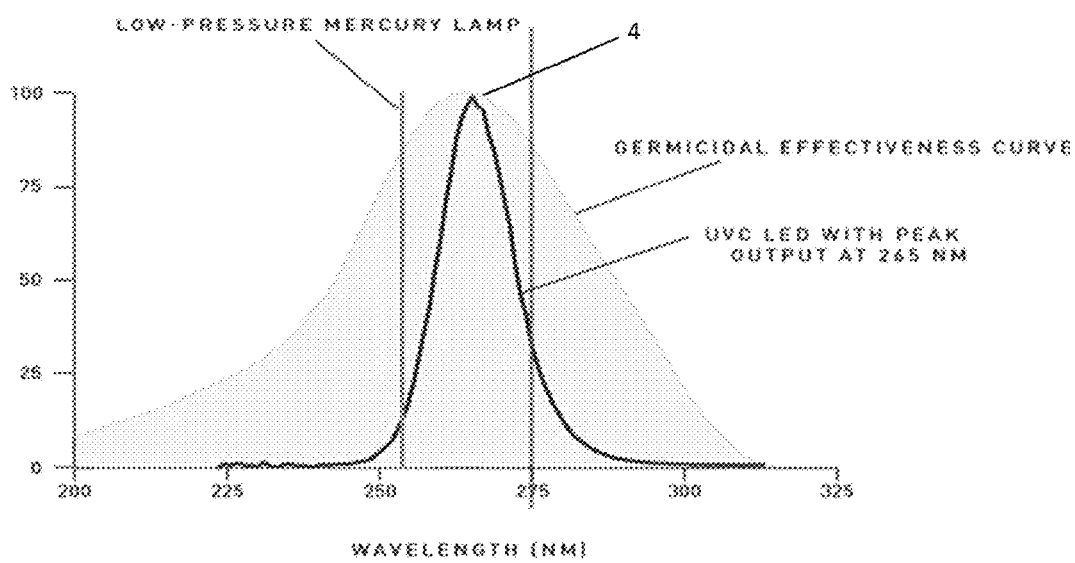
FIG. 2 is a graph showing germicidal effectiveness of UV light aa a function of light wave length.
Figure 3:
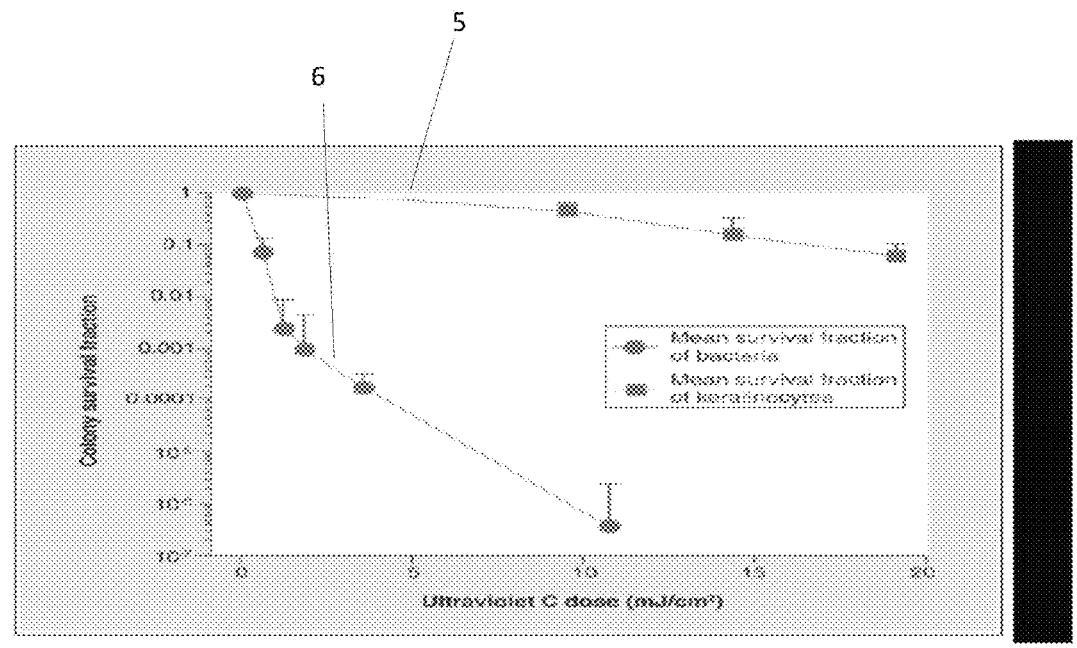
FIG. 3 is a graph showing survival fraction of bacteria and keratinocytes as a function of UV-C power dose at power rates measured in $mJ/cm^2$.

FIG. 2 is a graph showing germicidal effect of UV light at various wavelengths with a peak germicidal effectiveness 4 at the 265 nm wavelength. FIG. 3 taken from Expert Rev Anti Infect Ther. 2012 February; 10(2): 185-195. Ultraviolet C irradiation: an alternative antimicrobial approach to localized infections? By Tianhong Dai,1,2 Mark S Vrahas,3 Clinton K Murray,4 and Michael R Hamblin is a graph illustrating the effect of UV-C dosing of bacteria 6 and keratinocytes (skin) 5 relative to colony survival fraction and the relative safety of UV-C light with respect to pathogen kill and effect on skin cells. Even direct dose of UV-C at 10 mJ/cm$^2$ which kills substantially all of the bacteria has relative minimal effect on skin cells.

A typical bronchoscope endoscope 7 used in embodiments of the invention for carrying light transmitting fibers and which is difficult to sterilize is shown in FIGS. 4-8 having a light input through its insertion tube 10 with light from a light source box 13 shown in FIG. 6 (most typically with a xenon light source). An endoscope connector 15 shown in FIG. 5 is attached to the endoscope 7 shown in FIG. 4 with a light cable connection 11 to the endoscope and connection 14 to the light box 13. In order for the light cable connection to be utilizable for transmission of UV light it must be replaced with a flexible fiber optic cable of low UV attenuation with solarization resistance and optically connected to a light transmission system as described above.

FIG. 7 is a cross sectional view of the endoscope 7 showing water and air channels 16 and 17, a biopsy insertion valve 12 a with biopsy/suction channel 12. The biopsy/suction channel 12 is configured for removable insertion of various instruments such as ultrasound and biopsy sampling tools. FIGS. 8 and 8A are end and side views of the distal end 18 of the insertion tube 7a (generally about 5 mm diameter) with biopsy channel 12 outlet, light guide lens through which light is transmitted for illumination via illumination fibers 25 (which are flexible and usually of flexible polymers or silica not resistant to UV light degradation), an objective lens with ccd image takeup for viewing, and air and water jet channels 16 and 17.

FIGS. 10 and 10a are cross section views of an otoscope 30 with FIG. 10a being the cross-sectional view of the insertion speculum 35. An LED 33, powered by a battery 34 in a handle of the otoscope is coupled to a fiber bundle 31 which extends through the speculum 35 for insertion into a patient's nose, throat or ears. Extension of the fiber, when positioned into a patient's nose enables the fiber to pass the Eustachian tube in the rear of the nose into the inner ear, for UV treatment of inner ear infections. Fiber extension also enable them to be more closely positioned to possible infected areas in the throat and nose.

Figure 12:
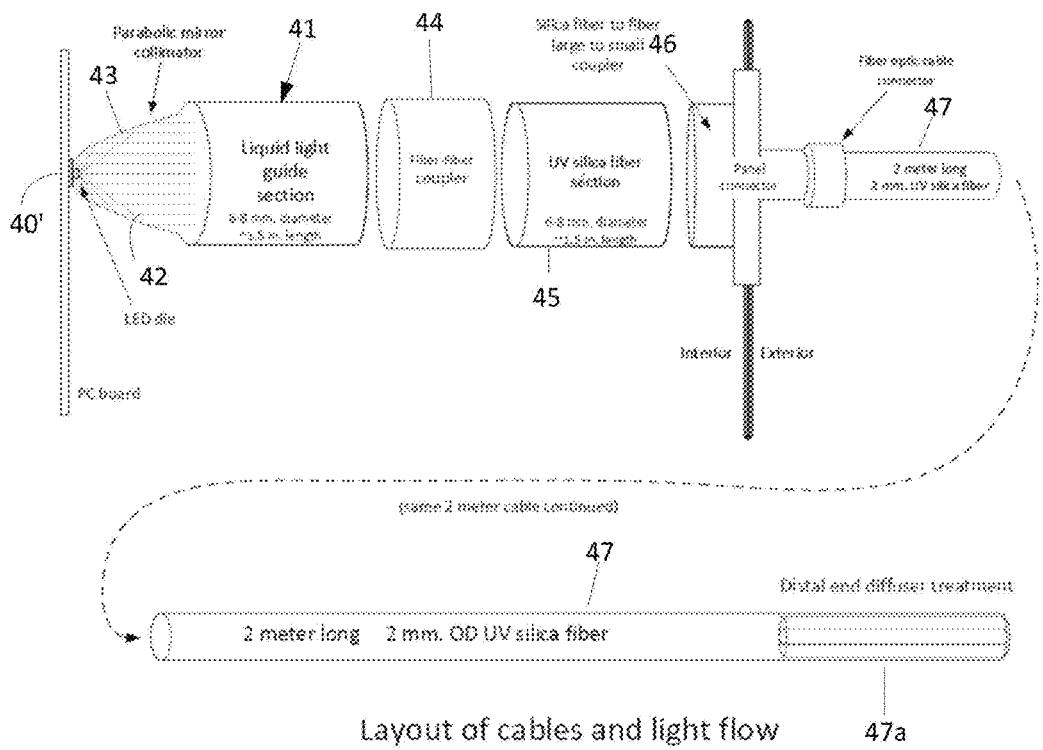
FIG. 12 is a schematic depiction of an embodiment of a UV light collection, transmission and emission structure using the UV light collection structure of FIG. 11 or 11A and transmission fibers of various dimensions.

FIGS. 11 and 12 depict embodiments of collimation of widespread light from the die 40a of UV emitting LED 40 with a collimating parabolic mirror 42 (aluminum) into a liquid light guide 41 for UV light transmission. In FIG. 11, the collimator parabolic mirror 42 is filled with air and the liquid light guide 41 has a closed end. In FIG. 12, the liquid light guide 41' is open ended with the parabolic mirror 42 containing the same liquid 43 as in the liquid light guide 41'. The LED 40 in both embodiments is fitted into a shaped recess 42a in the parabolic mirror 42. With the collimation, nearly all of the emitted light is gathered for increased eventual output.

Figure 13:
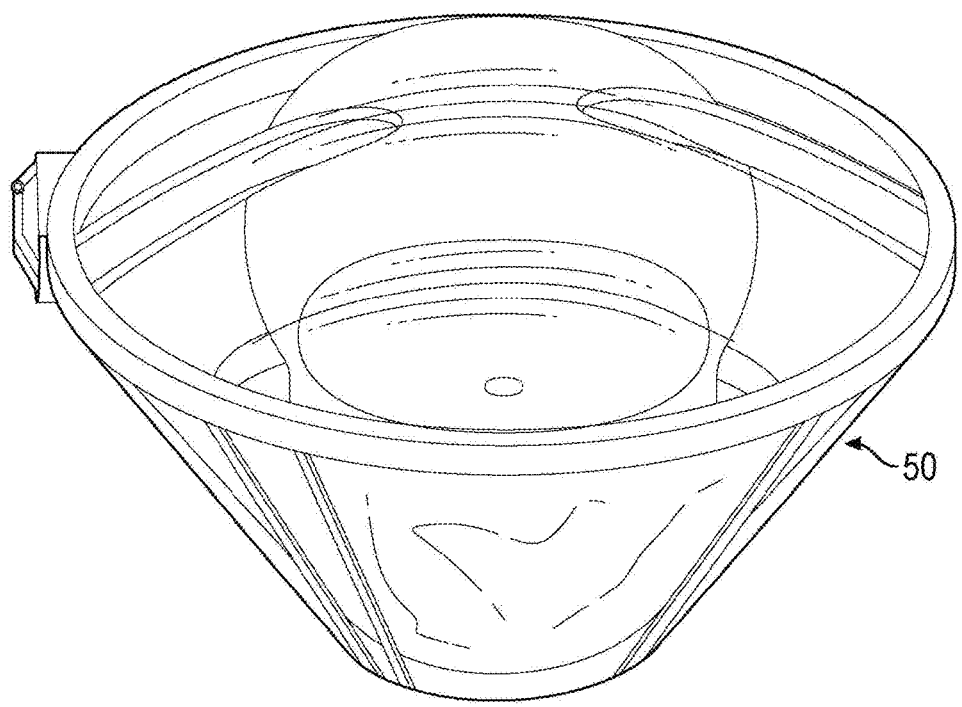
FIG. 13 is a perspective view of a TIR (total internal (illumination) reflection) lens having combined light collimating and focusing elements.

FIG. 13 is an embodiment of a UV light generation and transmission device 200 with the embedded UV LED 40 of FIG. 12, emitting UV light into a liquid light guide section 41 of relatively large diameter (6-8 mm) which is coupled to a UV silica fiber section 45 of low attenuation and of like size (with minimal coupling losses) via fiber coupler 44. The UV silica fiber section 45 is in turn coupled and focused into an elongated fiber optic operation section 47 of low UV attenuation fiber and of smaller diameter (2 mm as shown). This latter section is sized to fit into a biopsy channel of endoscope for either sanitization or disinfection thereof or for use in an endoscopic procedure to kill pathogens in situ within an organ of the body. The distal end of the operation section is shown with a distal end diffusor treatment 47A to facilitate UV generation over a wider and closer area. The operation section 47 may be directly coupled with a focusing element 44 to the liquid light guide. In addition, the operation section 47 may be removably coupled and disposable with considerations of disinfection and loss of flexibility as a function of its UV resistant structure. A wider fiber or light guide provides for greater UV light collection whereas a smaller diameter fiber is needed to enable effective positioning of UV emission at or near size restricted infection sites. In fact, for flexibility considerations, necessary for proper fiber positioning, the fibers should be able to have a 1 cm radius of curvature to match that of the endoscope through which it is inserted. A fiber bundle of 600 microns (0.6 mm) or less provides such flexibility curvature and focusing into a fiber bundle of such diameter is most desirable to avoid further losses of UV light and power.

FIG. 14 depicts a conical shaped TIR lens 50 having an integrated collimating lens shape configuration 50a together with a focusing surface 50b for the combined efficient collection of light directly from a widely scattering light source such as LED 40 of FIGS. 11, 12 and 13 and the subsequent focusing. FIG. 15 schematically depicts the paths of light 51 passing through the TIR lens with the collimating and focusing 52 to a focusing plane 51a into a relatively large fiber bundle 53 (8 to 12 mm). FIG. 16 depicts the TIR lens 50 with aligned UV light emitting diode 40 and emitted light 51 into cable ferrule 52 and then into operation fiber section 47. It is noted that all TIR lenses currently available are of plastic composition and are degradable and unsuitable for use with UV light refraction. Accordingly, effective TIR lenses of similar refractive shape are constructed of UV light resistant polished quartz crystal.

FIGS. 16 and 17 are similar in output structure to that of FIG. 12 but with the LED output collection being collected, collimated and focused by a TIR lens 50 (FIG. 16) and a parabolic mirror 60 with paired Fresnel lens 61 (FIG. 17) into a fiber ferrule 52 which is then focused into the small diameter operation fiber cable section.

FIG. 18 shows an alternative lens structure of a high refractive index spherical lens 70 for collecting, collimating and focusing output UV light 71 from the LED 40 into operation fiber 47.

FIG. 19 schematically depicts the sterilization of a small diameter (2.2 mm to 3.7 mm) biopsy/suction channel 12 of an endoscope which, because of its function, is a highly infectable region of the endoscope and at the same time, because of its difficult to access dimensions (2.2 mm to 3.7 mm ID×400-600 mm length), the most difficult and most time-consuming area to disinfect. The operation fiber section 47 of FIGS. 13, 17 and 18 is shown as inserted into the biopsy/suction channel 12 (the air and water channels are similar but are of even smaller ID dimension) with distance of the fiber 12 from the inner wall of the biopsy channel 12 exaggerated for clarity. The diffusion treated distal end of the fiber 47A (with removed section of cladding 47b) enables UV light to directly impinge on the adjacent channel walls 12 with rapid disinfection of the inner channel circumference, as the fiber 47 is moved in either a removal or insertion direction.

Similar FIG. 20 schematically depicts the sterilization of the biopsy/suction channel 12 with UV light emanating from the distal end of the operation fiber section 47 but without a diffusion treated distal end (with full cladding 47b). Impingement of the UV light on the inner walls of the biopsy/suction channel 12 is with a conical impingement.

FIG. 21 is a schematic equivalent of FIG. 20 with positioning of a UV transmitting fiber cable 47, without diffusion end treatment, inserted into a water pipe 112 for sanitization with the fiber emitting UV light in an angled cone against the inner walls of the pipe 112 with movement of the cable. Since the pipe is larger than an endoscope channel, the fiber 47 rests close to the bottom of the pipe and emits UV light closer to and with more power to the bottom of the pipe 112 and with lesser power to the more distant upper portion of the pipe. Timed movement sanitization is based on the upper portion sanitization rate. It is however noted that gravitational forces tend to direct pathogenic infected sites to the base or bottom of the pipe and that tends to even out the differential in movement time.

FIG. 22 is similar to that of the sanitization of the biopsy/suction channel of an endoscope with a fiber 47 having a diffusion end treatment 47A and a radially directed sanitization UV light impingement as in FIG. 19. Differential considerations of sanitization of upper and lower portion of the pipe interior are similar to those with respect to the sanitization of the pipe in FIG. 21.

Since water pipes are of much larger dimensions than those of biopsy/suction channels, UV emitting LEDs are able to be directly placed in a circular cylindrical structure 82 as shown in FIG. 23 for disinfection of a water pipe 112 with maximum disinfection power, without any attendant problems of biological harm. Electrical power is transmitted to the LEDs 40 via electrical connectors 81 and the structure 82 is moved through the pipe 112 via a controlling rod or pulled by a cord 80.

FIG. 24 illustrates the use of a bronchoscope 7 with a biopsy tool of optical fiber 47 extending out of the biopsy channel 12 and bronchoscope end 8 thereof and into the bronchia 10 of a lung 100. An optical fiber 47 used with a diameter of 1 mm is capable of being extended into bronchioles of 1 mm diameter where the 5 mm bronchoscope 7 is incapable of being positioned. With such proximity even relatively small amounts of UV power are able to effectively kill pathogens in a large portion (about 80%) of a typical lung. Bronchiole of less than 1 mm diameter are capable of having the UV light enter for short distances from extended fiber positioned at the mouth thereof.

FIG. 25 shows the types of DNA fragments of apoptotic and necrotic nature, indicated, as the DNA of a pathogen is unraveled, such as by UV light.

FIG. 26 depicts a 40 mW UV emitting LED at 265 nm 40 with positioned 30 degree lens 420, together with radiation pattern 400 and graphical details of wavelength 401, normalized output power, forward current vs. forward voltage 403, soldering conditions and physical/electrical properties 405

Figure 28:
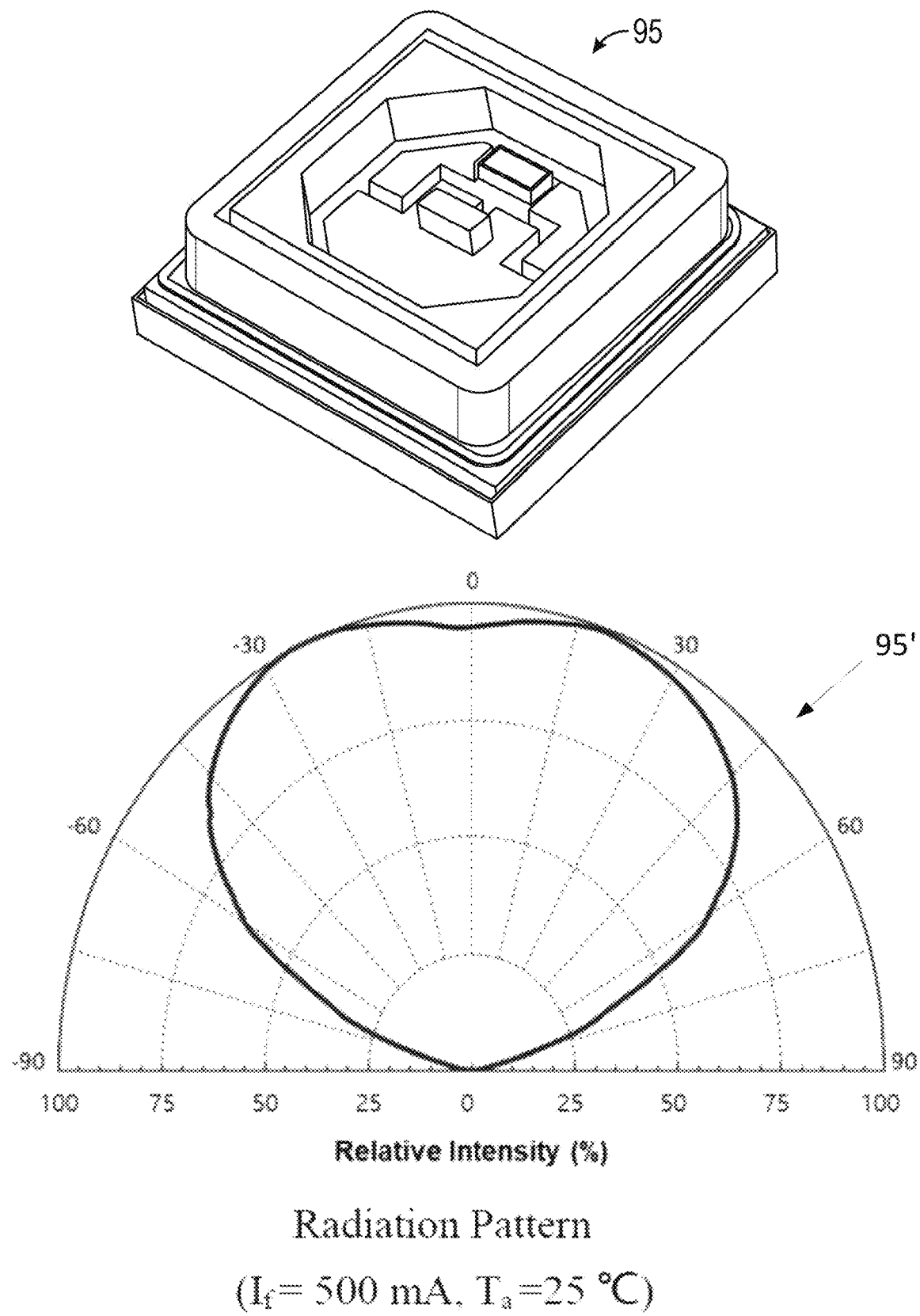
Figure 29:
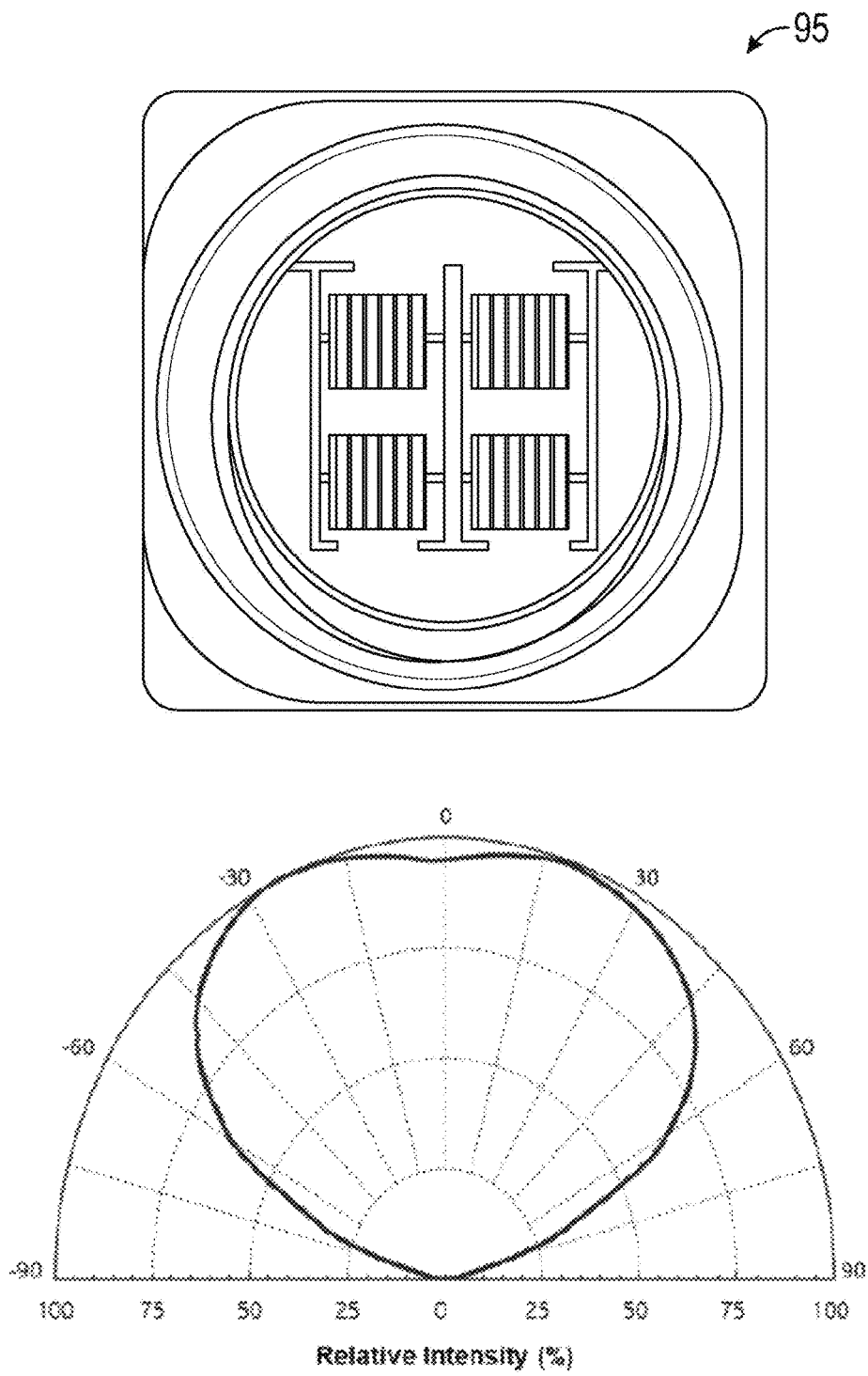

FIGS. 27, 28, and 29 show the 265 nm UV emitting LEDs made for the method and devices herein of 75 mW 75; 95 mW 95 and 360 mW 360, together with their respective radiation patterns 75', 95' and 360'. UV light falling outside an acceptance angle of about 27° in the radiation is not transmitted and is lost from any UV light emission patterns. With the radiation patterns of the respective LEDs being concentrated toward the center, lenses which reduce the angled emissions, such as the 30° lens with the 40 mW LED 40 of FIG. 26, increase the amount of light capable of being taken for transmission below the uptake angle limit of the transmission fiber. Despite estimated 20% losses with use of the lenses there is a net increase of transmittable UV light.

FIGS. 30 through 33B relate to embodiments of the structures and configurations of optical fibers used in the UV light transmission device.

FIGS. 30 and 30A show cross section and outside views of a tapered section 120 of a UV light carrying fiber with light transmission conversion from D1 to D2 and from D2 to D1 depending on the direction of UV light flow. Light striking the tapered section 120a which exceeds the acceptance angle is lost but the taper is effective in transmitting light which falls within the acceptance angle through smaller diameter 120b. The tapered section is utilized to transmit light gathered in a larger diameter fiber or fiber section to a smaller diameter fiber or fiber section for emission in restricted areas. However, light loss can be considerable.

FIG. 31 depicts a fiber cable 47 with fused core fiber bundle 48 with hexagonal ends of individual fibers which minimizes light loss resulting from interstitial spacing in FIG. 32 of about 30% by reducing such spacing. Only a short section needs the fused core for facilitated light input and the remainder of the fiber bundle should not be fused to enable the fiber bundles to retain required flexibility.

FIG. 32A depicts an end view of a 37 1000 um core fiber bundle 48 with an overall 6000 um diameter of the bundle with cladding 49 and FIG. 32B is a view of a single core fiber 48' of the same dimensions with cladding 49 and a relatively higher degree of rigidity but with a greater light uptake.

FIGS. 33A and 33B depict side views of the fiber cables 47 of FIGS. 32A and 32B with fiber bundles 48 and 48' respectively with alignment ferrules 490 at both ends of each of the fibers.

FIG. 34 shows a butt coupling of a fiber bundle 47 against the die 41 of an LED 40 with an end ferrule 490 held in an alignment jig 49'. Alignment is important to insure initial maximum UV light gathering from the LED. For greater effectiveness in light gathering the fiber core 48 should have a diameter or dimension to completely cover the LED die 41. Light that does not reach the fiber core is not collected and lost. However, even light that reaches the core, if it exceeds the acceptance angle of the core, it too will be lost from actual transmission.

FIG. 35 shows a transmission system with UV light from the die 41 from LED 40 through fused fiber bundle 48 of fiber cable 47 and a cable diameter of 1800 um with the light being focused through taper section 120 with a 3.6 to 1 taper to a light beam of 500 um diameter and into a ferrule 49 connection to fiber bundle 48 of a fiber cable 47 of 2 mm or 1 mm diameter with a 600 um diameter.

FIG. 36 is an alignment butt coupling jig 200 for aligning and butt coupling fiber cable 47 with ferrule 49 to LED 40 with adjustable alignment precision in an x-y plane via adjustment pins

EXAMPLES

Example 1

Figure 4:
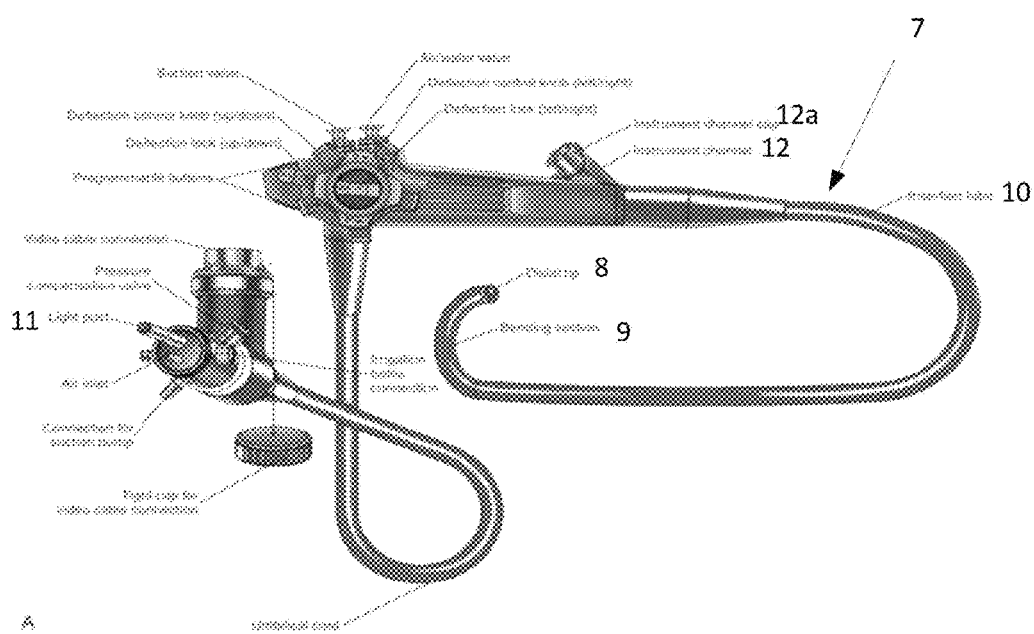
FIG. 4 depicts a prior art bronchoscope endoscope with parts labeled, showing internal insertion end and the external endoscope connection end.

The 75 mW 265 nm LED of FIG. 28 was butt coupled to an Olympus BF40 bronchoscope endoscope, similar to the ones shown in FIGS. 4 and 7, through its light connector and light was transmitted through the endoscope fiber. Total transmitted UV light output from the distal end of the endoscope, as measured by a 265 nm measuring radiometer was 0.0000 watts. The same LED was butt-coupled to a 600 um diameter low UV attenuation fiber of 1 meter length as a calibration. This resulted in an output of about 14.4 mW or 0.014 watts.

Example 2

As shown in a virtual simulation in FIG. 37, the 75 mW 265 nm LED was butt coupled to a 1 mm fiber with NA (attenuation) of 0.37 and a 21.5 degree half angle of acceptance, with a 6.1% coupling efficiency and with a UV output power of 6.1529D-02 watts. (0.0615 Watts or 6.15 mW)

Example 3

Similarly, FIG. 38 shows the efficiency of a 2 mm fiber bundle butt coupled to the 75 mW LED as 13.9% with a UV output power of 1.3922E-01 watts. (13.9 mW)

A ray tracing procedure was effected with respect to the procedure described in Examples 2 and 3 and as illustrated in FIGS. 37 and 38 and with the radiation pattern of FIG. 39:

The ray tracing is a simulation of radiation pattern based on the following and as performed with non sequential Zemax simulation software:
1. With reference to FIG. 39, light is emitted from a virtual 1 Watt LED die that is 1.2 mm by 1.2 mm square positioned vertically on the left part of the diagram and emitting its light to the right.
2. The light emitted has a wavelength of 265 nm and is being emitted from every point on the top surface of the LED in a 120° side to side angle, i.e., from the single direction perpendicular to the die surface, all rays that form an angle of 60° or less in any direction are traced outward light to see which and how many make it through the virtual aperture of the LED, positioned 0.25 mm from the LED window through a vertical aperture 10 mm away from the die surface.
3. That aperture represents the surface of an optical fiber and is set so that it passes through only rays that are within the acceptance angle of the fiber, specifically rays that form an angle with the perpendicular of 21.5° or less.
4. 20 million random rays are started and followed, with a certain granularity from each and every point on the LED die surface and exiting with a certain granularity of every angle in any direction forming less than a 60° angle with the vertical.
5. The rays making it through are totaled within each incremental area of the virtual aperture. Based on the 20 million rays having a power of 1 Watt, the totals of all the incremental areas indicate:
    a. That the area with the most concentrated number of rays has a peak "power per unit area" of 0.173 Watts per square centimeter;

Procedure of Butt Coupling a LED and a Fiber—Analysis, Simulation, and Measurement:

Delivering UV light through a medium, in this case starting from an LED source and transmitting the light into a fiber optic cable, begins with the coupling of a die of an LED and the fiber. A simple and straightforward method of implementing this, though not necessarily the best or most efficient is by using the method of "butt coupling". In this procedure a proximal end of the fiber is brought into close contact with the die of the LED as closely as possible since actual touching is detrimental to the integrity of the die (which is normally protectively covered in any event). Since LED light spreads out widely from the die component inside the LED, typically at a 120° to 130° angle, it is efficacious to allow as little of angular expansion to occur as possible by starting the coupling close to the die before the light has a chance to spread. Emissions and effectiveness of the coupling are evaluated herein in three ways, which are in close agreement with each other:
1. Ray tracing simulation—involving the simulation of the light source as a source of typically millions of rays coming out in all possible directions and flowing them to see how and if they enter the simulated fiber aperture.
2. Actual measurements of known LEDs and fiber configurations—The LED dies have a variety of sizes (square) and power (emitted) and the fiber optic cables have a variety of core sizes. The fibers used are short and have low attenuation for the UV light used. The power out of the raw LED as well as the out of the fiber(s) coupled to the LED were measured with an "integrating sphere" type of radiometer, which is similar to how the power of LEDs is specified by their manufacturer. This produces the highest values, but takes into account all the radiated output, regardless of direction. The conclusions derived from these tests are used only for relative coupling efficiency percent (100× Power Out/Power In). Since difficult to obtain special UV versions of such a radiometer was not available, a much less sensitive visible light version was used on a correlative basis since, regardless of the absolute power reported, the efficiency (a ratio, or relative calculation) is regarded as correct.

As support for this, the sensitivity graph of the ThorLabs S142C integrating sphere sensor for the Thor PM320E radiometer used is shown as FIG. 40. At 350 nm, and presumably also at the lower 265 nm, the sensitivity is 0.75/0.05 or 15 times lower sensitivity. Ratios of power measurements are considered valid.

3. Simple calculations based on the proportion of die area covered by the abutting fiber cable end and its area can be taken into account. Thus, a fiber that covers only ½ of the 2D area of LED die will have about, or at least, ½ of the total power coupled, since the central portion covered has equal or greater radiant strength.

The following are analyses and comparisons of the LEDs and cables as Examples 4-10:

Example 4

A Ray tracing simulation of a 1 Watt 120° LED into a 1 mm fiber with large aperture was used to determine coupling efficiency LED Power out/Fiber Power in.

Example 5

A Ray tracing simulation of a 1 Watt 120° LED into a 2 mm fiber with large aperture was used to determine coupling efficiency LED Power out/Fiber Power in.

Example 6

2000 um, 3000 um and 4000 um fibers, of two different Numeric Apertures were measured, butt coupled to a UV-C LED, with methods sufficient for measuring relative efficiency (ratio of Power out/Power in), as previously mentioned.

Example 7

A 360 mW LED die that is 4 mm×4 mm butt coupled to a 1 mm fiber is analyzed using area covering ratios to determine additional losses due to non-covered light.

Example 8

A 360 mW LED die that is 3 mm×3 mm butt coupled to a 1 mm fiber is analyzed using area covering ratios to determine additional losses due to non-covered light.

Example 9

A 75 mW LED die that is 1.2 mm×1.2 mm butt coupled to a 1 mm fiber is analyzed using area covering ratios to determine additional losses due to non-covered light.

Example 10

A 90 mW LED die that is 1.38 mm×1.38 mm butt coupled to a 1 mm fiber is analyzed using area covering ratios to determine additional losses due to non-covered light.
Results:
Example 4—This ray tracing, FIG. 37, showed an efficiency of LED to 1 mm fiber coupling of 6.15%.
Example 5—This ray tracing, FIG. 38, showed an efficiency of LED to 2 mm fiber coupling of 13.9%.
Example 6—A 3000 um NA 0.28 cable had a measured efficiency of 23%.
A 4000 um NA 0.22 cable had a measured efficiency of 32%. (the largest diam. cable)
A 2000 um NA 0.28 cable had a measured efficiency of 22%.
A 2000 um NA 0.22 cable had a measured efficiency of 24%.
From these measurements, made with an integrating sphere radiometer, the value 22% can be used as a guide for how much of the total LED irradiation comes through a fiber, butt-coupled to an LED.
Example 7—360 mW LED die that is 4 mm×4 mm butt coupled to a 1 mm fiber area ratio analysis: The 4 mm square die has an area of 16 mm2 (square millimeters). The 1 mm fiber, having a radius of 0.5 mm has an area of PI*(0.5)2=0.785 mm2 That area is 4.91% of 16 mm2. 4.91% of 22%=1.1% coupling efficiency.
Example 8—1% of 360 mW is 3.89 mW out.
Relative size of the round 1 mm diameter fiber over a 4 mm square LED die.
Example 9—360 mW LED die that is 3 mm×3 mm butt coupled to a 1 mm fiber area ratio analysis:
The 3 mm square die has an area of 9 mm2 (square millimeters).
The 1 mm fiber, having a radius of 0.5 mm has an area of PI*(0.5)2=0.785 mm2.
That area is 8.72% of 9 mm2.
8.72% of 22%=1.92% coupling efficiency
1.92% of 360 mW is 6.91 mW out.
Relative size of the round 1 mm diameter fiber over a 3 mm square LED die.
Example 10—75 mW LED die that is 1.2 mm×1.2 mm butt coupled to a 1 mm fiber area ratio analysis:
The 1.2 mm square die has an area of 1.44 mm2 (square millimeters).
The 1 mm core fiber, having a radius of 0.5 mm has an area of PI*(0.5)2=0.785 mm2.
That area is 54.5% of the 1.44 mm2.
54.5% of 22%=12.0% coupling efficiency
12.0% of 75 mW is 8.99 mW out of the fiber.
Relative size of the round 1 mm diameter fiber over a 1.2 mm square LED die.
The above cited IEEE study used a single 18 mW 275 nm LED at a distance of 3 cm, releasing 600 mJ max of energy in 30 seconds to reduce Covid virus by 99.9%.
At the distance of 3 cm from the irradiated surface, the 120° wide emitted light covers a circular area of radius 2.6 cm (diameter 5.2 cm), thus having an illuminated area (Pi r2) of 21.2 cm2.

The 75 mW LED is at 265 nm has about 25% more efficacy than 275 nm, thus this LED is to be considered as providing 11.2 mW. At 3 cm distance, 600 mJ of energy would take 600 mJ/(11.2 mJ/sec)=53.6 seconds and able to sanitize a spot 5.2 cm in diameter.
At 2 cm distance, ⅔ times as close, the time would be (⅔)2, 0.44 times shorter=23.6 s and able to sanitize a spot 3.5 cm in diameter.
At 1 cm distance, ⅓ times as close, the time would be (⅓)2, 0.109 times shorter=5.84 s and able to sanitize a spot 1.73 cm in diameter.
At 2 mm distance, 1/15 times as close, the time would be (1/15)2, 0.0044 times shorter=0.238 s and able to sanitize a spot 0.35 cm (3.5 mm) in diameter.
Example 11-90 mW LED die that is 1.38 mm×1.38 mm butt coupled to a 1 mm fiber area analysis:
The 1.38 mm square die has an area of 1.90 mm2 (square millimeters). The 1 mm fiber, having a radius of 0.5 mm has an area of PI*(0.5)2=0.785 mm2 That area is 41.3% of 1.90 mm2.
41.3% of 22%=9.10% coupling efficiency and 9.10% of 90 mW is 8.12 mW out.
Relative size of the round 1 mm diameter fiber over a 1 mm square LED die.
Example 12—75 mW LED die that is 1.2 mm×1.2 mm butt coupled to a 500 um fiber—area ratio analysis: The 1.2 mm square die has an area of 1.44 mm2 (square millimeters). The 500 um core fiber, having a radius of 0.250 mm, has an area of PI*(0.25)2=0.196 mm2. That area is 13.6% of the 1.44 mm2. 13.6% of 22%=3.0% coupling efficiency with 3.0% of 75 mW is 2.25 mW out of the fiber.
Relative size of the round 0.5 mm diameter fiber core over a 1.2 mm square LED die. The 75 mW LED is at 265 nm which has about 25% more efficacy than 275 nm this LED is to be considered as 2.81 mW. At 3 cm distance, 600 mJ of energy would take 600 mJ/(2.81 mJ/sec)=213.5 seconds and is able to sanitize a spot 5.2 cm in diameter. At 2 cm distance, ⅔ times as close, the time would be (⅔)2, 0.44 times shorter=94.0 s and able to sanitize a spot 3.5 cm in diameter. At 1 cm distance, ⅓ times as close, the time would be (⅓)2, 0.109 times shorter=40.6 s and able to sanitize a spot 1.73 cm in diameter. At 2 mm distance, 1/15 times as close, the time would be (1/15)2, 0.00444 times shorter=0.949 s and able to sanitize a spot 3.5 mm in diameter.

Calculation for Disinfection of a 2 mm Diameter Biopsy Channel 660 mm Long Using a 1 mm O.D. Version of the Sanitizing Cable From the IEEE study, a 275 nm, 120° emitting, 20 mW LED, used for 30 sec at a distance of 3 cm, deactivated a culture of Covid 19 Sars virus by 99.9%.
A distance of 3 cm from a 120° spreading light produces a circular irradiation area of 21.2 cm². The radius at that distance is 2.6 cm. The area, Pi R squared, is 2,123 square mm.
(Note—Units are in parenthesis and a mW of power is the same as a mJ/second)

$$\text{Energy(mJ)} = \text{Intensity(mW/cm}^2\text{ or mJ/sec/cm}^2) \times (\text{Time (sec)} \times \text{Area(cm}^2))$$

I) For the IEEE study, to find the Intensity used, we solve for Intensity and use:

$$\text{Intensity} = \text{Energy}/(\text{Time} \times \text{Area}), \text{which in the study is:}$$

$$\text{Intensity} = 600\text{mJ}/(30\text{ sec} \times 21.2\text{ cm}^2) = 0.94\text{ mW/cm}^2 \text{ or about} 1\text{ mW/cm}^2$$

The IEEE study used about 1 mW per square centimeter for 30 seconds.

II) The invention's UV light through a fiber into a biopsy channel.

Calculating the surface area inside the 2 mm diameter biopsy channel is done as follows:

For calculations of area, a cylindrical tube surface is "cut" along a longitudinal dotted line and unrolled into a flat rectangle like a label of a can. That rectangle's length and width are, respectively, the length of the tube and the circumference of the tube, illustrated below.

That rectangle has a length of 660 mm (26 inches) and a width which is the biopsy channel circumference.

The radius of the channel is 1 mm, so the circumference, (2 Pi r), is 6.3 mm.

That rectangle area is therefore 660×6.3=4,158 mm$^2$, or 41.58 cm$^2$.

Measurements were made of the light from a 1.2 mm square 75 mW LED emitter, butt-coupled into a 600 um core fiber optic cable, which showed an emerging intensity of 14.4 mW/cm$^2$. Accounting for the 265 nm 25% benefit over 275 nm, that is an effective 18.0 mW/cm$^2$.

If the same amount of Covid 19 virus in the study were inside the biopsy channel, 99.9% reduction would take 0.8 seconds by the following calculation:

Definition of Intensity, Converted to Energy: (Units in Parenthesis)

$$\text{Energy(mJ)}=\text{Intensity}(\text{mJ/sec/cm}^2))\times\text{Time(sec)}\times\text{Area}(\text{cm}^2)$$

Solving for time, $$\text{Time(sec)}=\text{Energy}/(\text{Intensity}\times\text{Area})$$

In our case, the specifics are:

$$\text{Time}=600\text{mJ}/(18\ \text{mW/cm}^2\times 41.58\ \text{cm2})=0.80\ \text{seconds}$$

At these levels and especially with higher power LEDs, at similar close range, delivery of sufficient UV-C light in reasonable time to kill a malignant lymph node becomes possible. These nodes are already discovered, categorized, and repeatably located, using mature EBUS (EndoBronchial UltraSound) technology and UV-C delivery fiber cables inserted inside the 1 mm I.D. aspirating needles, which themselves have been inserted through an endoscope biopsy channel and guided precisely via ultrasound to where UV-C delivery is needed, right inside a malignant lymph node, accessed from within pulmonary bronchi.

An additional butt coupling assembly is shown in FIG. 41 wherein an SMA 490 hold and retains a fiber bunder 47 for butt engagement with aligned LED die 41. FIGS. 41A-D show the fiber cable 47 as respectively alternatively having a single core 48*a*, 3 fibers 48*b*, 7 fibers 48*c* and 19 fibers 48*d*. Fiber cable with greater number of fibers have lesser amounts of interstitial gaps and with greater light pick up.

FIG. 42 is illustrative of a structure capable of focused cancer treatment even in normally non accessible areas of the body. An EBUS aspiration needle 300 normally utilized for biopsy sample taking of cancerous tissue (EBUS is specific to lung biopsy but equivalent EUS aspiration needles are utilizable in other parts of the body and even in normally inaccessible sites such as the pancreas). The aspiration needle 300 generally has about a 1 mm OD and an 0.97 mm ID for biopsy sample extraction without any significant damage. The UV light transmitting fiber 347 is of a diameter under 1 mm and capable of being inserted into the aspiration needle as shown and extensible therefrom. With this structure, the optical fiber 347 is carried and steered into parts of the body normally inaccessible even by endoscopes and is carried within cancerous lesions, tumors and tissue where it is able to emit UV light within cancerous sites to effect DNA deconstruction of the cancer directly from within the cancer. This provides a much less radical radiation type treatment specifically directed only at a cancer site with enhanced safety and increased efficacy. The short range and limited penetration of UV-C enhances its safe utilization though it may necessitate continued penetration and positioning of the UV-C carrying into different parts of the cancerous site for maximum effect.

FIG. 43 illustrates an efficacious fiber optic assembly wherein a UV emitting LED 500 is provided with a lens such as the 30 degree lens of the 40 mW LED shown in FIG. 26. The lens directs and partially collimates emitted UV light 512 into aspherical lens 501 at or below the acceptance angle for full acceptance. The light is then transmitted into a second reverse positioned aspherical lens 502 where it focuses the light 512 into a very small spot of about 500 um directly into a flexible 600 um fiber. Simulated transmission calculations show an overall 75% emission of the initially emitted light from the LED. This was simulated as being 75 mW from the 95 mW LED of FIG. 28 and is extrapolated to be about 270 mW from the 360 mW LED of FIG. 29 to the fiber at 503. The amount of light going into the angle of acceptance is estimated to be about 10 to 12% of the light of about 27 to 40 mW of final light transmission power. FIG. 44, shows the ray tracing of the light 512 into fiber cable 47 as being 100%. However, a portion of the light rays fall out of the acceptance angle of the fiber. FIG. 45 shows the small focused spot of the light beam 512 of the fiber at about 500 um.

FIG. 46 shows a handle 600 for control of the light fiber cable 47. FIG. 47 shows the fiber cable 47 as inserted into endoscope 7 through biopsy channel valve entry 12A into biopsy channel 12 with extending control handle 600. The handle has a pushbutton 601 which controls extension of the cable 47 out of the end 8 (seen in FIGS. 4, 8 and 9) of the endoscope to expose diffusion section 47A with UV emission therefrom. Scale 602 indicates degree of extension position of the extended fiber cable from endoscope end 8. The LED UV light source and optical connection to the fiber cable 47 are contained within handle 600.

It is understood that the above descriptions, figures, and examples are only illustrative of the invention and that changes in structure, composition and components of the device and steps and requirements of the method are only illustrative and that changes may be made without departing from the scope of the invention as defined in the following claims.

What is claimed is:

1. A method for disinfecting pathogens from pathogen infected areas inaccessible to direct UV light, comprising the steps of:

i) optically combining UV light source, with a power output of at least 2 mW, with a UV light output at a wave length level which provides pathogen deactivation by RNA and/or DNA disruption, with a proximal end of a tangible transmission medium, capable of transmitting UV light emitted from the UV light source and having a proximal and distal end, and fiber having an acceptance angle at the proximal end, for the UV light at the UV wave length level between, the optical combining being effected by means of an optically aligned optical interface between the UV light source and the proximal end of the tangible transmission medium, whereby emitted UV light from the light source is directed within the acceptance angle and transmitted through the fiber optic cable tangible transmission medium and emitted out of the second distal end thereof, ii) providing the tangible transmission medium with a UV light collection structure for collecting the UV light emitted from the light source at the proximal end thereof into the acceptance angle and for emitting collected UV light output at a movable distal end thereof, to which output UV light is transmitted, iii) providing the UV light source and the tangible transmission medium with a jig structure which holds and maintains a fixed relative distance and position, with optical alignment, between the proximal end of the tangible transmission medium and the UV light source in the optical interface, with the distal end being movable, and wherein UV light direction and optical alignment are not disrupted with movement of the distal end of the tangible transmission medium, wherein the jig structure comprises:
  a) a holding element which is fixedly engaged with the proximal end of the tangible transmission medium,
  b) a support element for the UV light source and
  c) a position fixed spacer structure between the UV light source and the proximal end of the tangible transmission medium, iv) configuring and dimensioning at least a portion of the distal end of the tangible transmission medium to be capable of being inserted into or adjacent an otherwise inaccessible pathogen infected or possibly pathogen infected area, to an extent that light transmitted through the tangible transmission medium and emitted out of the distal end is able to effectively reach pathogens of the pathogen infected or possibly infected area;

v) providing the emitted UV light from the distal end with a power intensity sufficient to disinfect the pathogen infected or possibly infected area from pathogens at a desired proximate distance and within a desired reasonable time period; and vi) inserting the distal end of the tangible transmission medium into or directly adjacent to the pathogen infected or possibly infected area and providing UV light thereto with the sufficient power level intensity at the desired proximate distance.

2. The method of claim 1, wherein the pathogen infected area or possibly pathogen infected area is human or animal blood, within the human or animal, and the distal end of the tangible transmission medium is inserted within a blood vessel of the human or animal and wherein blood circulation brings infecting pathogens into proximity to UV light emitted from the distal end of the tangible transmission medium.

3. The method of claim 1; with the further steps of the distal end of the tangible transmission medium being moved to at least one other pathogen infected or possibly pathogen infected area and transmitting disinfecting UV light through the tangible transmission medium whereby the UV light impinges on the at least one other pathogen infected or possibly pathogen infected area at a desired distance from the distal end and for the desired time sufficient to acceptably disinfect the at least one other pathogen infected or possibly pathogen infected area.

4. The method of claim 1, wherein the pathogen infected or possibly pathogen infected area is at least one of an instrument channel, suction channel, combined instrument and suction channel, water channel and air channel of an endoscope.

5. The method of claim 1, wherein the UV light collection structure is configured to provide the steps of:
  i) collecting and collimating scattered UV light emitted from a widely scattering non-coherent light source LED to a diameter effective to permit capture by the tangible transmission medium which is comprised of a fiber optic cable of a substantial portion of non-coherent light emitted by the LED light source;
  ii) introducing the collimated light into the low UV attenuation light transmitting fiber optic cable of a diameter at least substantially equal to that of the collimated light;
  iii) focusing the collimated light to a focal point into a smaller diameter fiber optic cable of desired size; and
  iv) emitting light from the smaller diameter fiber optic cable for pathogen deactivation.

6. A method of increasing pathogen eradicating distal UV light output in the method of claim 1, comprising the steps of:
  a. collimating a substantial portion of UV light output from the LED by optically integrating the LED with a collimating member having a light output diameter greater than that of a die of the LED;
  b. collecting a substantial portion of the collimated UV light with a light collector and transmitter element having a low UV light attenuation transmission, with the light collector and transmitter having a diameter optically matched to the light output diameter of the collimating member;
  c. and transmitting and focusing the collected collimated light into the proximal end of the fiber optic transmission cable with a distal end light output of UV against a pathogen in proximity thereto.

7. The method of claim 1, wherein the pathogen infected area is infected with mold, fungus or mildew.

8. A method for the remote eradication of pathogens within a human or animal in accordance with the method of claim 1 wherein the tangible transmission medium comprises a fiber optic cable having been provided with an integral treatment for radial UV light diffusion, comprising the steps of:
  i) inserting the fiber optic cable into an endoscope;
  ii) steering the endoscope within the human or animal to a site possibly infected with a pathogen;
  iii) extending the distal end of the fiber optic cable out of a distal end of the endoscope;
  iv) radially emitting the UV light against a proximate pathogen infected or possibly pathogen infected area.

9. The method of claim 1 wherein the tangible transmission medium is comprised of a fiber optic cable with the distal end of the fiber optic cable being provided with an integral treatment for radial UV light diffusion.

10. A device for the remote eradication of pathogens comprising:
  a) a UV light source, comprising a laser, or an LED, each with a power output of at least 2 mW, with a UV light output at a wave length level which provides pathogen deactivation by RNA and/or DNA disruption,
  b) a tangible solid or liquid transmission medium, having a proximal end and a distal end, which tangible transmission medium is capable of transmitting UV light emitted from the UV light source, and the transmission medium having an acceptance angle for the UV light, and an optical interface between the laser or LED UV light source and the tangible transmission medium whereby emitted UV light from the UV light source is directed to the proximal end of the transmission medium within the acceptance angle, whereby the directed UV light is transmitted through the tangible transmission medium, wherein the optical interface provides a fixed, optical alignment for the direction of emitted UV light from the UV light source within the acceptance angle of the transmission medium, and c) the device having a jig structure which holds and maintains a fixed relative distance and position, with optical alignment, between the proximal end of the transmission medium and the UV light source in the optical interface, with the distal end being movable and wherein UV light direction and optical alignment are not disrupted with movement of the distal end of the transmission medium, wherein the jig structure comprises:

i) a holding element which is fixedly engaged with the proximal end of the transmission medium,
ii) a support element for the UV light source and
iii) a position fixed spacer structure between the UV light source and the proximal end of the transmission medium, wherein UV light emitted from the distal end of the tangible transmission medium, which distal end is movable and moved and directed against pathogens in proximity thereto, is at a UV power level sufficient to substantially effectively deactivate RNA and/or DNA of the pathogens within a reasonable period of time.

11. The device of claim 10, wherein the light source for emitting UV light comprises at least one UV light emitting diode (LED) comprising a light emitting die, wherein the tangible transmission medium comprises a low UV attenuation, solarization resistant, fiber optic cable comprised of at least one segment, and wherein the optical interface comprises an acceptance angle aligned optical connection between the UV light emitting die and the fiber optic cable selected from at least one of a direct butt coupling between the fiber optic cable and the light emitting die; and a light collecting and light collimating lens system which collects light from the light emitting die and collimates it for transmission and directs it to the proximal end of the fiber optic cable within the UV light acceptance angle.

12. The device of claim 11, wherein the light emitting diode provides a UV light emission output at a wave length level between 250 nm and 285 nm, with a power output of at least 40 mW and wherein UV light emitted from the fiber optic cable and directed against the pathogen, in proximity thereto, is at a level of at least 2 mW/cm$^2$.

13. The device of claim 11, wherein UV light emitted from the LED is captured, collimated and focused into the proximal end of the light transmission fiber with a TIR lens optically connected with the LED.

14. The device of claim 11, wherein UV light emitted from the distal end of the fiber optic cable, and directed against a pathogen in proximity thereto, is configured to be at a power level of at least 2 mW/cm$^2$.

15. The device for eradication of pathogens of claim 10, wherein the tangible UV light transmission medium is comprised of a UV light transmitting lens.

16. A remote pathogen eradication device in combination with an endoscope, with the device comprising a UV light source optically coupled to a tangible UV light transmission medium capable of transmitting a UV light emitted from the light source, the tangible UV light transmission medium having a proximal and distal end, with the distal end being movable and configured to be carried and steered within a human body or animal to a pathogen infected area or possibly infected area therein by the endoscope having an instrument insertion channel therein and with the tangible UV light transmission medium having sufficient flexibility for steered positioning thereof by the carrying endoscope, wherein the tangible UV light transmission medium is configured to be insertable into the instrument insertion channel and movably retained therein, for positioning emitted UV light emission from the distal end to the pathogen infected area or possibly pathogen infected area within the human or animal for pathogen eradication at the infected site and wherein the tangible UV light transmission medium is extendible and retractable within the insertion channel for closer positioning of UV light emission from the distal end to the infected site, wherein the device comprises:

a) a UV light source, with a UV light output at a wave length level providing pathogen deactivation by RNA and/or DNA disruption,
b) a tangible solid or liquid UV light transmission medium, capable of transmitting UV light emitted from the UV light source, which has an acceptance angle for the UV light at the wave length level, and
c) an optical interface between the UV light source and the proximal end of the tangible UV light transmission medium whereby emitted UV light from the light source is directed to the proximal end within the acceptance angle whereby the directed UV light is transmitted through the tangible UV light transmission medium, wherein the optical interface provides a fixed, optical alignment for the direction of emitted UV light from the UV light source within the acceptance angle of the tangible UV light transmission medium, and
d) the device having a jig structure which holds and maintains a fixed relative distance and position, with optical alignment, between the proximal end of the tangible UV light transmission medium and the UV light source in the optical interface, whereby UV light direction and optical alignment are not disrupted with movement of the distal end of the tangible UV light transmission medium within the instrument insertion channel, wherein the jig structure comprises:
i) a holding element which is fixedly engaged with the proximal end of the tangible UV light transmission medium,
ii) a support element for the UV light source and
iii) a position fixed spacer structure between the UV light source and the proximal end of the tangible UV light transmission medium, wherein UV light emitted from the movable distal end of the tangible UV light transmission medium which is moved into proximity and directed against pathogens is at a UV light power level sufficient to substantially effectively deactivate RNA and/or DNA of the pathogens within a reasonable period of time.

17. The device of claim 16, wherein the light source for emitting UV light comprises at least one light emitting diode (LED) comprising a light emitting die, and wherein the tangible transmission medium comprises a low UV attenuation fiber optic cable comprised of at least one segment.

18. The device of claim 17, wherein the fiber optic cable is configured to be carried and steered within a human or animal to a cancer infected site therein within an aspiration needle having a hollow therein and the needle being configured for positioning and insertion directly into a cancer infected site, wherein a portion of the fiber optic cable is dimensioned to be insertable into the hollow of the needle and movably retained therein, whereby a distal section of the fiber optic cable is extendible and retractable from within the hollow of the needle, with the needle having been inserted into a cancer infected site, whereby the fiber optic cable is positionable, with extension from the needle, for emitting UV light directly into the cancer infected site for inactivation of cancer cells at the cancer infected site.

* * * * *